US010256423B2

(12) United States Patent
Son et al.

(10) Patent No.: US 10,256,423 B2
(45) Date of Patent: Apr. 9, 2019

(54) ORGANIC SOLAR CELL AND METHOD FOR FABRICATING THE SAME

(71) Applicant: KOREA INSTITUTE OF SCIENCE AND TECHNOLOGY, Seoul (KR)

(72) Inventors: Hae Jung Son, Seoul (KR); Min Jae Ko, Seoul (KR); Jai Kyeong Kim, Seoul (KR); Hyo Sang Lee, Seoul (KR); Jea Woong Jo, Seoul (KR); Sungmin Park, Seoul (KR); Jae Hoon Yun, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 69 days.

(21) Appl. No.: 15/378,318

(22) Filed: Dec. 14, 2016

(65) Prior Publication Data

US 2017/0288156 A1   Oct. 5, 2017

(30) Foreign Application Priority Data

Mar. 30, 2016 (KR) .................. 10-2016-0038620
Jul. 19, 2016 (KR) .................. 10-2016-0091463

(51) Int. Cl.
*C07F 7/22* (2006.01)
*C08K 3/04* (2006.01)
*C08G 61/12* (2006.01)
*C08L 65/00* (2006.01)
*H01L 51/00* (2006.01)
*H01L 51/42* (2006.01)

(52) U.S. Cl.
CPC ........ *H01L 51/0094* (2013.01); *C07F 7/2208* (2013.01); *C08G 61/126* (2013.01); *C08L 65/00* (2013.01); *H01L 51/0036* (2013.01); *H01L 51/0047* (2013.01); *H01L 51/0068* (2013.01); *H01L 51/0071* (2013.01); *C08G 2261/124* (2013.01); *C08G 2261/146* (2013.01); *C08G 2261/1412* (2013.01); *C08G 2261/18* (2013.01); *C08G 2261/226* (2013.01); *C08G 2261/228* (2013.01); *C08G 2261/3223* (2013.01); *C08G 2261/3241* (2013.01); *C08G 2261/3246* (2013.01); *C08G 2261/344* (2013.01); *C08G 2261/91* (2013.01); *H01L 51/4253* (2013.01); *Y02E 10/549* (2013.01)

(58) Field of Classification Search
CPC .................................................. H01L 51/0094
See application file for complete search history.

(56) References Cited

FOREIGN PATENT DOCUMENTS

KR   10-2015-0072762 A   6/2015
KR   10-2015-0094562 A   8/2015

OTHER PUBLICATIONS

Lee et al. "Synergistic effects of solvent and polymer additives on solar cell performance and stability of small molecule bulk heterojunction solar cells" Journal of Materials Chemisty A, 2016, vol. 4, pp. 18383-18391.*

Vinay Gupta et al., Barium: An Efficient Cathode Layer for Bulk-heterojunction Solar Cells, Jun. 11, 2013, Scientific Reports, pp. 1-6.

* cited by examiner

*Primary Examiner* — Joseph R Kosack
(74) *Attorney, Agent, or Firm* — Goldilocks Zone IP Law

(57) ABSTRACT

An organic solar cell is provided. The organic solar cell includes a photoactive layer in which a low molecular weight conjugated compound as a first organic semiconductor material is mixed with an appropriate amount of a second organic semiconductor material. The first organic semiconductor material includes both electron donors and electron acceptors. The presence of the electron donors and the electron acceptors in the first organic semiconductor material improves the morphology of the photoactive layer, leading to high efficiency of the organic solar cell.

9 Claims, 22 Drawing Sheets

ORGANIC SOLAR CELL AND METHOD FOR FABRICATING THE SAME

CROSS-REFERENCE TO RELATED APPLICATIONS

This application claims, under 35 U.S.C. § 119, the priority of Korean Patent Application Nos. 10-2016-0038620 and 10-2016-0091463 filed on Mar. 30, 2016 and Jul. 19, 2016, respectively, in the Korean Intellectual Property Office, the disclosure of which is incorporated herein by reference in its entirety.

BACKGROUND OF THE INVENTION

Field of the Invention

The present invention relates to an organic solar cell and a method for fabricating the same. More specifically, the present invention relates to an organic solar cell including a photoactive layer whose morphology is improved due to the presence of both electron donors and electron acceptors and a method for fabricating the organic solar cell.

Description of the Related Art

Fossil fuels are currently used as major energy sources and are faced with various problems, such as limited reserves as well as environmental pollution caused by combustion. Thus, with the increasing interest in inexhaustible and environmentally friendly alternative energy sources to fossil fuels, research has been conducted on various renewable energy sources, such as hydrogen energy, water power, and wind power. Particularly, considerable research efforts have been made to develop solar cells using sunlight.

Solar cells are broadly classified into two types by the kind of material they use: solar cells using inorganic materials, such as silicon, and solar cells using organic materials. In comparison with inorganic solar cells using silicon, thin film solar cells using organic materials can be fabricated on a large area at low cost by coating processes, such as spin coating, screen printing, ink-jet printing, and microcontact printing because organic materials are easy to process. The use of organic materials enables the fabrication of flexible devices by roll-to-roll processing, contributing to cost reduction.

Initially, organic solar cells using polymers have been investigated with much attention. However, the molecular weight (Mn, Mw) and polydispersity index (PDI) of polymers vary with increasing degree of polymerization, resulting in poor reproducibility of the finished devices.

In view of such problems, highly reproducible organic solar cells using low molecular weight compounds are attracting attention as alternatives to organic solar cells using polymers. However, high efficiency is a prerequisite for the commercialization of organic solar cells using low molecular weight compounds.

PRIOR ART DOCUMENTS

Patent Documents

Patent Document 1: Korean Patent Publication No. 10-2015-0072762

SUMMARY OF THE INVENTION

The present invention has been made in view of the above problems, and it is an object of the present invention to provide a highly efficient organic solar cell including a photoactive layer with improved morphology and a method for fabricating the organic solar cell.

One aspect of the present invention provides an organic solar cell including: a lower electrode formed on a substrate; a photoactive layer formed on the lower electrode and including (a) a p-type organic semiconductor material, (b) an n-type organic semiconductor material, and (c) a solvent; and an upper electrode formed on the photoactive layer wherein the p-type organic semiconductor material includes (a-1) a first organic semiconductor material represented by Formula 1:

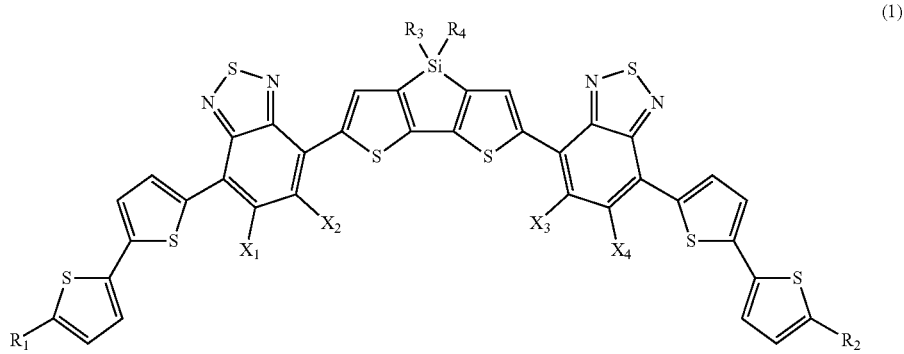

(1)

wherein $X_1$, $X_2$, $X_3$, and $X_4$ may be the same or different and are each independently hydrogen (H) or a halogen and $R_1$, $R_2$, $R_3$, and $R_4$ may be the same or different and are each independently a $C_1$-$C_{22}$ linear or branched alkyl group, and (a-2) a second organic semiconductor material represented by Formula 2:

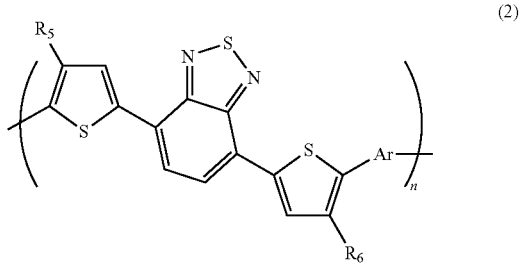

(2)

wherein $R_5$ and $R_6$ may be the same or different and are each independently H or a $C_1$-$C_{22}$ linear or branched alkyl group, n is an integer from 1 to 10,000,000, and Ar is selected from aromatic groups having the following structures 2a:

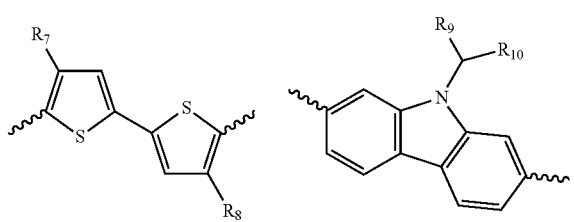

(2a)

wherein $R_7$, $R_8$, $R_9$, and $R_{10}$ may be the same or different and are each independently H or $C_1$-$C_{22}$ linear or branched alkyl group.

In Formula 1, $R_1$ and $R_2$ may be the same or different and are each independently a $C_1$-$C_7$ linear alkyl group and $R_3$ and $R_4$ may be the same or different and are each independently a $C_8$-$C_{22}$ branched alkyl group. In Formula 2, $R_5$ and $R_6$ may be the same or different and are each independently H or a $C_8$-$C_{22}$ branched alkyl group.

When $R_1$ and $R_2$ in Formula 1 are symmetric and have the same structure, $R_3$ and $R_4$ in Formula 1 may be symmetric and have the same structure, $R_5$ and $R_6$ in Formula 2 may be symmetric and have the same structure, $R_7$ and $R_8$ in Formula 2a may be the same or different and are each independently H or a $C_8$-$C_{22}$ linear alkyl group, and $R_9$ and $R_{10}$ in Formula 2a may be the same or different and are each independently H or a $C_8$-$C_{22}$ branched alkyl group.

The first organic semiconductor material (a-1) may be a low molecular weight compound having a molecular weight of 1000 to 2000 g/mol and the second organic semiconductor material (a-2) may be a high molecular weight compound having a molecular weight of 50,000 to 100,000 g/mol.

The first organic semiconductor material (a-1) may be selected from the low molecular weight compounds represented by Formulae 3 to 7:

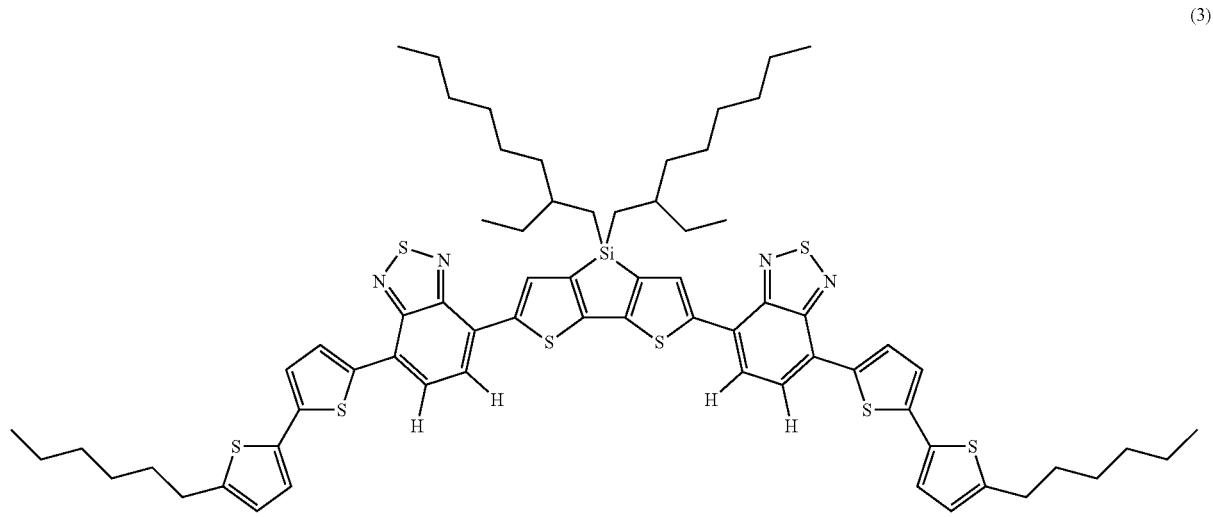

(3)

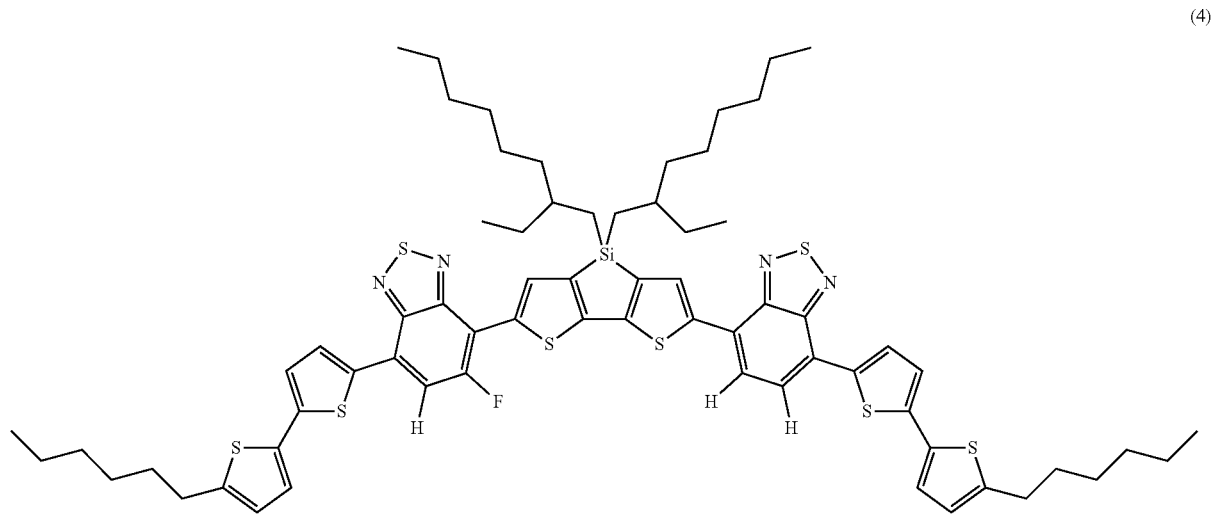

(4)

(5)
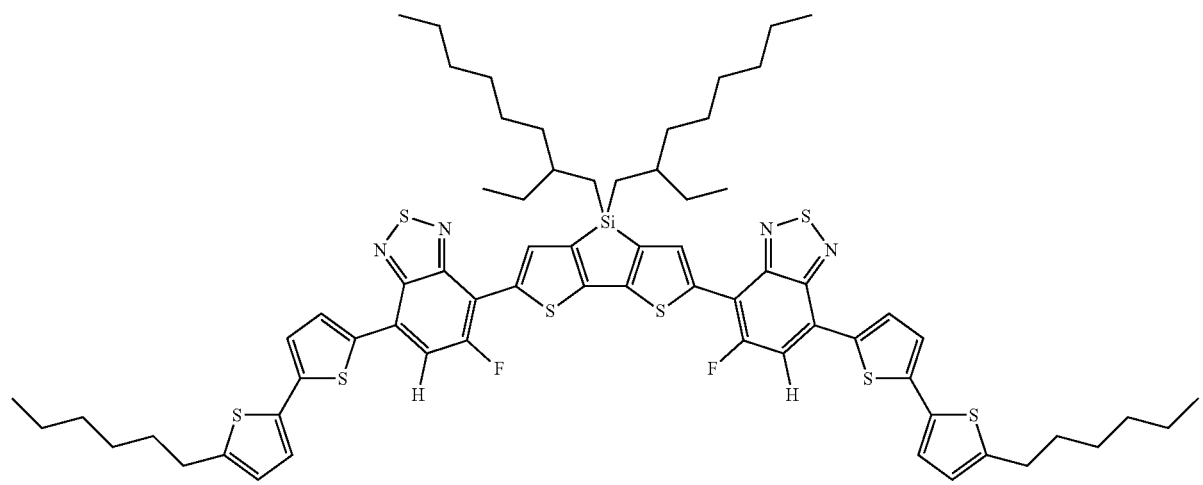
(6)
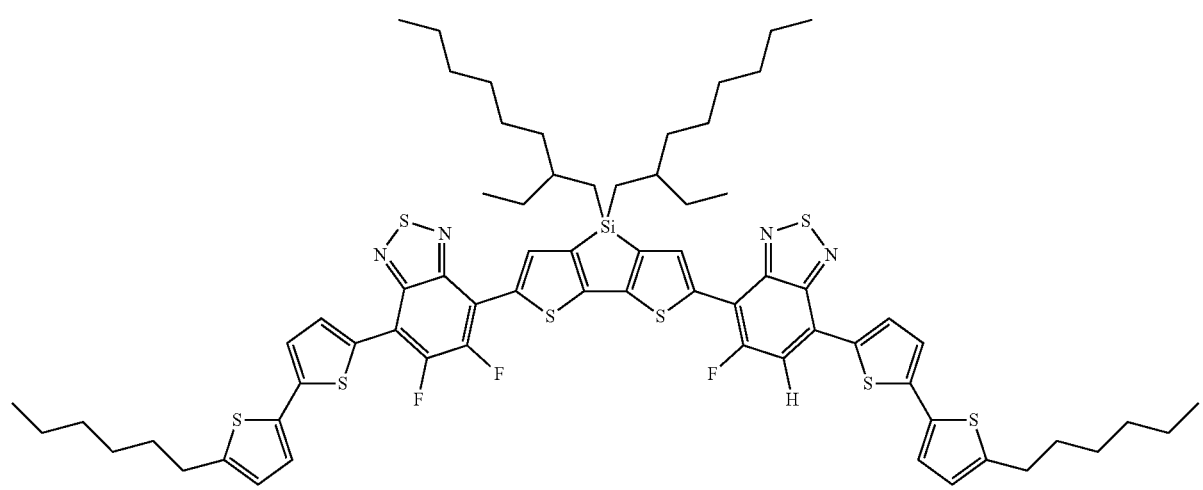
(7)
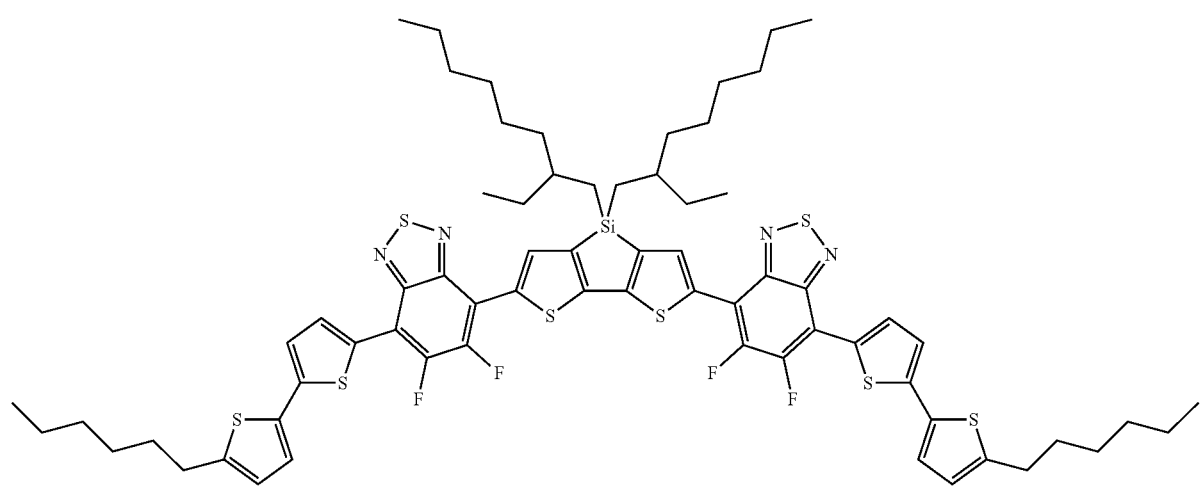

The second organic semiconductor material (a-2) may be a high molecular weight compound represented by Formula 8 or 9:

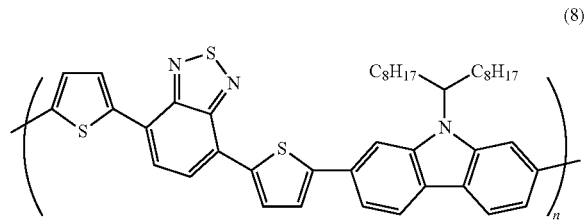

(8)

wherein n is an integer from 1 to 10,000,000,

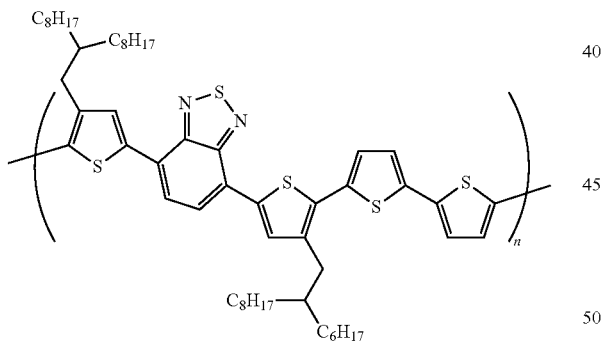

(9)

wherein n is an integer from 1 to 10,000,000.

Preferably, the second organic semiconductor material has a molecular weight of 50000 to 100000 g/mol.

The n-type organic semiconductor material (b) may be selected from the group consisting of methyl (6,6)-phenyl-C61-butyrate ($PC_{60}BM$), (6,6)-phenyl-C61-butyric acid methyl ester ($C_{60}$-PCBM), (6,6)-phenyl-C71-butyric acid methyl ester ($C_{70}$-PCBM), (6,6)-phenyl-C77-butyric acid methyl ester ($C_{76}$-PCBM), (6,6)-phenyl-C79-butyric acid methyl ester ($C_{78}$-PCBM), (6,6)-phenyl-C81-butyric acid methyl ester ($C_{80}$-PCBM), (6,6)-phenyl-C83-butyric acid methyl ester ($C_{82}$-PCBM), (6,6)-phenyl-C85-butyric acid methyl ester ($C_{84}$-PCBM), bis(1-[3-(methoxycarbonyl)propyl]-1-phenyl) (Bis-$C_{60}$-PCBM), 3'-phenyl-3'H-cyclopropa(8,25)(5,6)fullerene-C70-bis-D5h(6)-3'-butyric acid methyl ester (Bis-$C_{70}$-PCBM), indene-C60-bisadduct (ICBA), monoindenyl C60 (ICMA), and combinations thereof.

The first organic semiconductor material (a-1) may be mixed with the second organic semiconductor material (a-2) in a weight ratio of 1:0.01-0.04.

The solvent (c) may be a mixture of chlorobenzene and 1,8-diiodooctane.

The chlorobenzene may be mixed with the 1,8-diiodooctane in a volume ratio of 1:0.002-5.

A further aspect of the present invention provides a method for fabricating an organic solar cell, including:

I) forming a lower electrode on a substrate;

II) mixing (a-1) a first organic semiconductor material represented by Formula 1:

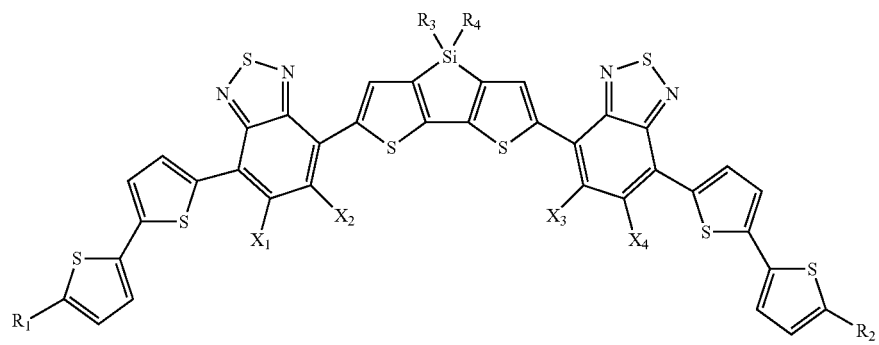

(1)

wherein $X_1$, $X_2$, $X_3$, and $X_4$ may be the same or different and are each independently hydrogen or a halogen and $R_1$, $R_2$, $R_3$, and $R_4$ may be the same or different and are each independently a $C_1$-$C_{22}$ linear or branched alkyl group, (a-2) a second organic semiconductor material represented by Formula 2:

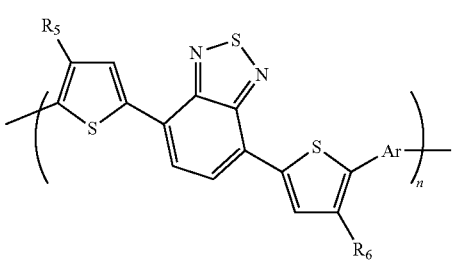

(2)

wherein $R_5$ and $R_6$ may be the same or different and are each independently hydrogen or a $C_1$-$C_{22}$ linear or branched alkyl group, n is an integer from 1 to 10,000,000, and Ar is selected from aromatic groups having the following structures 2a:

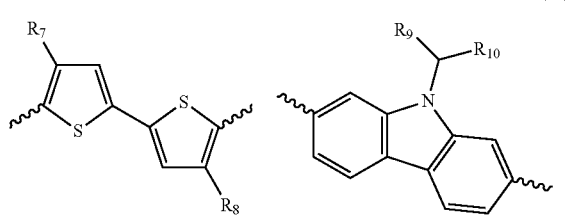

(2a)

wherein $R_7$, $R_8$, $R_9$, and $R_{10}$ may be the same or different and are each independently H or a $C_1$-$C_{22}$ linear or branched alkyl group, (b) an n-type organic semiconductor material, and (c) a solvent to prepare a first solution;

III) coating the first solution on the lower electrode to form a photoactive layer; and IV) forming an upper electrode on the photoactive layer.

The first organic semiconductor material (a-1) may be mixed with the second organic semiconductor material (a-2) in a weight ratio of 1:0.01-0.04.

The solvent (c) may be a mixture of chlorobenzene and 1,8-diiodooctane.

The chlorobenzene may be mixed with the 1,8-diiodooctane in a volume ratio of 1:0.002-5.

Step III) may be carried out by spin coating.

The organic solar cell of the present invention includes a photoactive layer in which a low molecular weight conjugated compound as a first organic semiconductor material is mixed with an appropriate amount of a second organic semiconductor material. The first organic semiconductor material includes both electron donors and electron acceptors. The presence of the electron donors and the electron acceptors in the first organic semiconductor material improves the morphology of the photoactive layer, leading to high efficiency of the organic solar cell.

In addition, the second organic semiconductor material added to the first organic semiconductor material prevents the first organic semiconductor material from aggregating so that the morphology of the photoactive layer can be improved, achieving improved network structural properties of the first organic semiconductor material.

Furthermore, the method of the present invention enables the fabrication of an organic solar cell with high efficiency through room temperature processing without the need for high temperature annealing. Therefore, according to the method of the present invention, the fabrication procedure is simplified, the fabrication cost is reduced, and the choice for heat-labile materials is widened.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
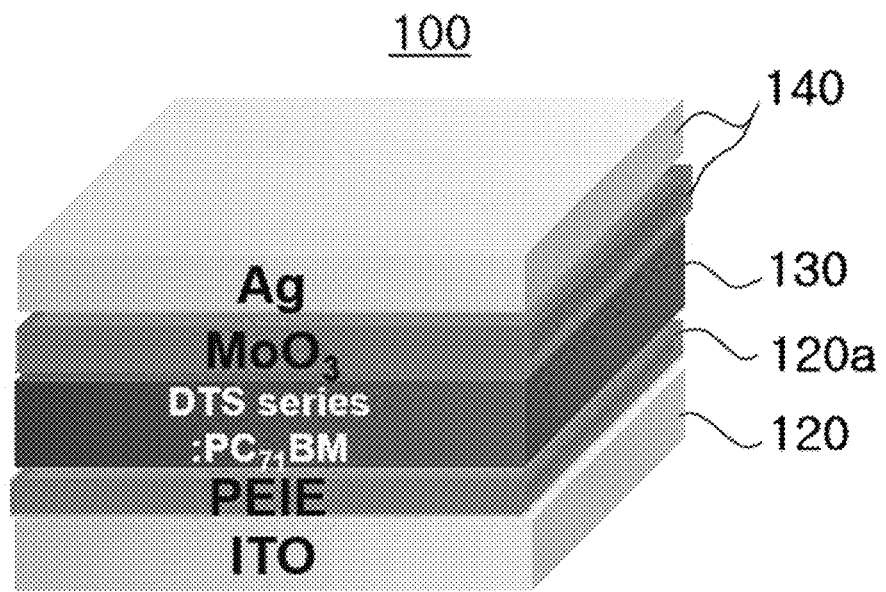
FIG. 1 is a cross-sectional view of an organic solar cell according to the present invention.
Figure 2:
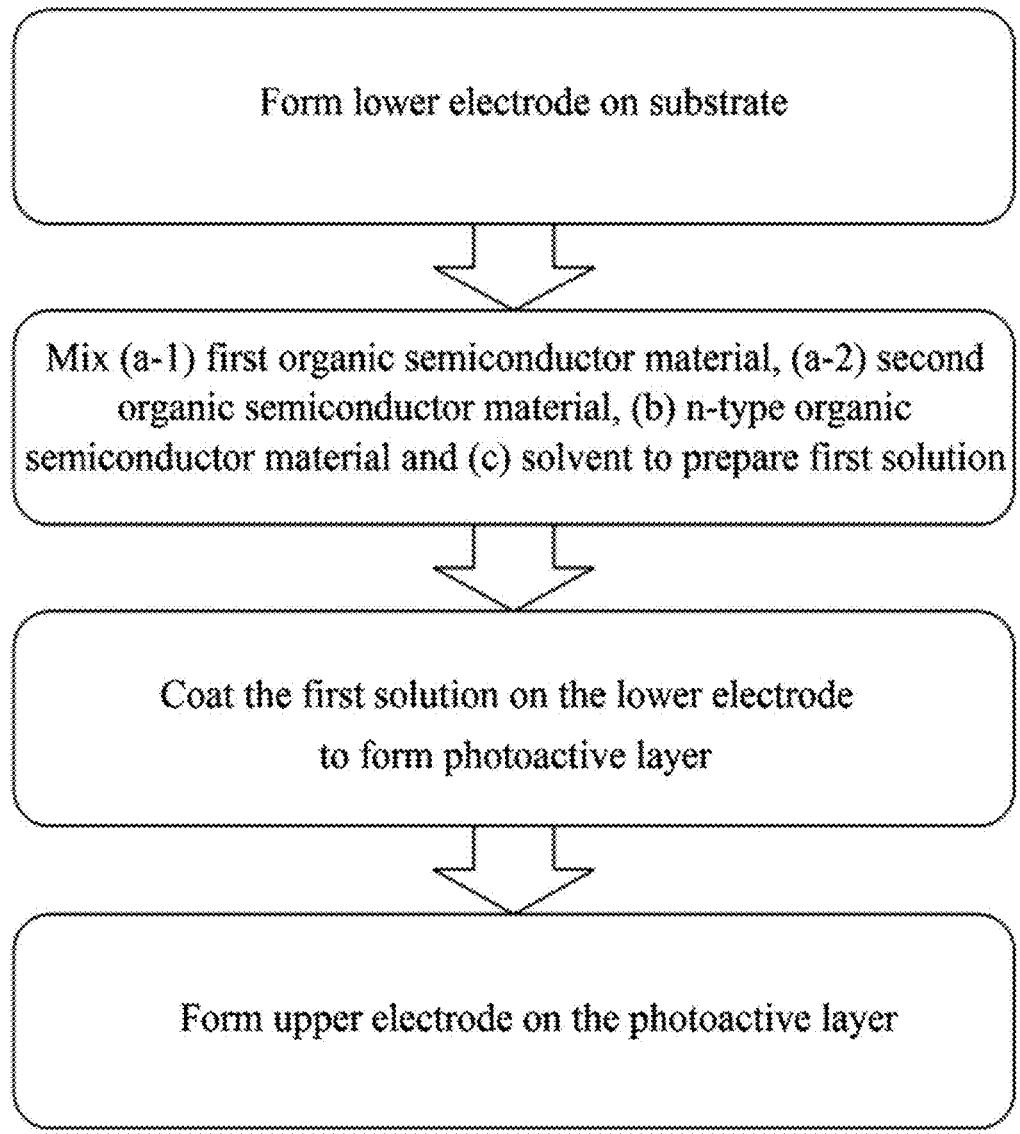
FIG. 2 is a flowchart schematically illustrating a method for fabricating an organic solar cell according to the present invention.

Several aspects and various embodiments of the present invention will now be described in more detail.

Small molecule organic solar cells have drawn a great deal of researcher's interest due to their superior reproducibility over polymer organic solar cells. For such small molecule organic solar cells, p-DTS(FBTTh$_2$)$_2$ was developed as a typical photovoltaic active material. The use of a mixture of p-DTS(FBTTh$_2$)$_2$ and a $C_{71}$ fullerene derivative with high electron affinity for the fabrication of devices having a conventional structure can achieve high efficiencies of ~7%. However, due to the tendency for the low molecular weight compounds to aggregate, the morphology of the photovoltaic active layers is not optimized, and as a result, a further increase in efficiency is no longer achieved.

The present inventors have carried out research to solve the above problems and found that when a low molecular weight compound as a first organic semiconductor material is mixed with an appropriate amount of a second organic semiconductor material to form a photoactive layer of a small molecule organic solar cell, the low molecular weight compound is prevented from aggregating and the morphology of the photoactive layer is optimized, achieving greatly improved photoelectric conversion efficiency of the organic solar cell.

One aspect of the present invention is directed to an organic solar cell including: a lower electrode formed on a substrate; a photoactive layer formed on the lower electrode and including (a) a p-type organic semiconductor material, (b) an n-type organic semiconductor material, and (c) a solvent; and an upper electrode formed on the photoactive layer wherein the p-type organic semiconductor material includes (a-1) a first organic semiconductor material represented by Formula 1:

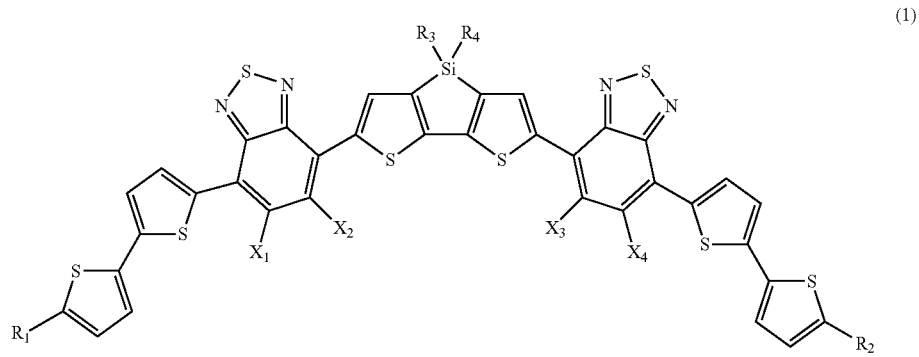

(1)

wherein $X_1$, $X_2$, $X_3$, and $X_4$ may be the same or different and are each independently hydrogen (H) or a halogen and $R_1$, $R_2$, $R_3$, and $R_4$ may be the same or different and are each independently a $C_1$-$C_{22}$ linear or branched alkyl group, and (a-2) a second organic semiconductor material represented by Formula 2:

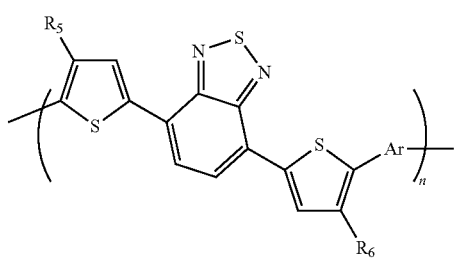

(2)

wherein $R_5$ and $R_6$ may be the same or different and are each independently H, a $C_1$-$C_{22}$ linear or branched alkyl group, n is an integer from 1 to 10,000,000, and Ar is selected from aromatic groups having the following structures 2a:

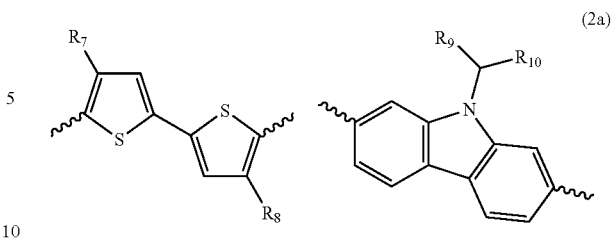

(2a)

wherein $R_7$, $R_8$, $R_9$, and $R_{10}$ may be the same or different and are each independently H or a $C_1$-$C_{22}$ linear or branched alkyl group.

It is preferred that when $R_1$ and $R_2$ in Formula 1 are symmetric and have the same structure, $R_3$ and $R_4$ in Formula 1 are symmetric and have the same structure and $R_5$ and $R_6$ in Formula 2 are symmetric and have the same structure. Such structures of the first and second organic semiconductor materials are advantageous for intermolecular energy transfer.

It is most preferred that $R_1$ and $R_2$ in Formula 1 are the same or different and are each independently a $C_1$-$C_7$ linear alkyl group, $R_3$ and $R_4$ in Formula 1 are the same or different and are each independently a $C_8$-$C_{22}$ branched alkyl group, and $R_5$ and $R_6$ in Formula 2 are the same or different and are each independently H or a $C_8$-$C_{22}$ branched alkyl group. When the first organic semiconductor material is mixed with the second organic semiconductor materials, their side chains provide the most improved intermolecular stacking and supramolecular alignment.

The above-described effects are most profound when $R_1$ and $R_2$ in Formula 1 are symmetric and have the same structure, $R_3$ and $R_4$ in Formula 1 are symmetric and have the same structure, $R_5$ and $R_6$ in Formula 2 are symmetric and have the same structure, $R_7$ and $R_8$ in Formula 2a are the same or different and are each independently H or a $C_8$-$C_{22}$ linear alkyl group, and $R_9$ and $R_{10}$ in Formula 2a are the same or different and are each independently H or a $C_8$-$C_{22}$ branched alkyl group.

In particular, $X_1$, $X_2$, $X_3$, and $X_4$ in Formula 1 are the same or different and are each independently hydrogen or F.

The structure of the organic solar cell according to the present invention will be explained in more detail with reference to FIG. 1.

FIG. 1 is a cross-sectional view illustrating the organic solar cell 100 of the present invention. Referring to FIG. 1, a lower electrode 120, a photoactive layer 130, and an upper electrode 140 are formed in this order on a substrate 110.

The organic solar cell 100 may further include a polyethylenimine ethoxylated (PEIE) surface modified layer 120a between the lower electrode 120 and the photoactive layer 130.

The photoactive layer 130 includes (a) a p-type organic semiconductor material, (b) an n-type organic semiconductor material, and (c) a solvent.

The p-type organic semiconductor material (a) includes (a-1) a first organic semiconductor material represented by Formula 1:

It is preferred that when $R_1$ and $R_2$ in Formula 1 are symmetric and have the same structure, $R_3$ and $R_4$ in Formula 1 are symmetric and have the same structure and $R_5$ and $R_6$ in Formula 2 are symmetric and have the same structure. Such structures of the first and second organic semiconductor materials are advantageous for intermolecular energy transfer.

It is most preferred that $R_1$ and $R_2$ in Formula 1 are the same or different and are each independently a $C_1$-$C_7$ linear alkyl group, $R_3$ and $R_4$ in Formula 1 are the same or different

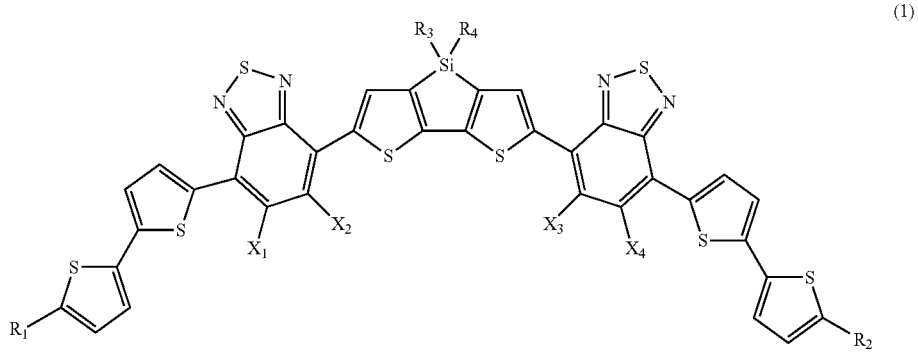

(1)

wherein $X_1$, $X_2$, $X_3$, and $X_4$ may be the same or different and are each independently hydrogen or a halogen and $R_1$, $R_2$, $R_3$, and $R_4$ may be the same or different and are each independently a $C_1$-$C_{22}$ linear or branched alkyl group, and (a-2) a second organic semiconductor material represented by Formula 2:

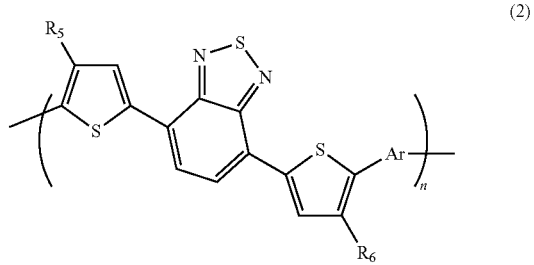

(2)

wherein $R_5$ and $R_6$ may be the same or different and are each independently H or a $C_1$-$C_{22}$ linear or branched alkyl group, n is an integer from 1 to 10,000,000, and Ar is selected from aromatic groups having the following structures 2a:

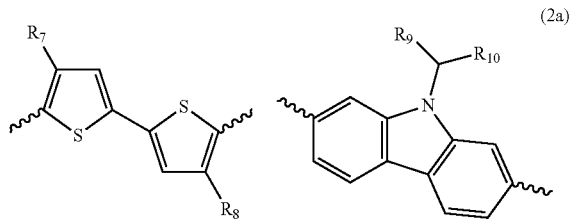

(2a)

wherein $R_7$, $R_8$, $R_9$, and $R_{10}$ may be the same or different and are each independently H or a $C_1$-$C_{22}$ linear or branched alkyl group.

and are each independently a $C_8$-$C_{22}$ branched alkyl group, and $R_5$ and $R_6$ in Formula 2 are the same or different and are each independently H or a $C_8$-$C_{22}$ branched alkyl group. When the first organic semiconductor material is mixed with the second organic semiconductor materials, their side chains provide the most improved intermolecular stacking and supramolecular alignment.

The above-described effects are most profound when $R_1$ and $R_2$ in Formula 1 are symmetric and have the same structure, $R_3$ and $R_4$ in Formula 1 are symmetric and have the same structure, $R_5$ and $R_6$ in Formula 2 are symmetric and have the same structure, $R_7$ and $R_8$ in Formula 2a are the same or different and are each independently H or a $C_8$-$C_{22}$ linear alkyl group, and $R_9$ and $R_{10}$ in Formula 2a are the same or different and are each independently H or a $C_8$-$C_{22}$ branched alkyl group.

In particular, $X_1$, $X_2$, $X_3$, and $X_4$ in Formula 1 are the same or different and are each independently hydrogen or F.

According to one embodiment of the present invention, the substrate 110 may be made of a material selected from the group consisting of glass, polycarbonate (PC), polyethylene terephthalate (PET), polyethylene naphthalate (PEN), and polyether sulfonate (PES). The substrate 110 is preferably a glass substrate.

According to one embodiment of the present invention, the lower electrode 120 may be an anode or a cathode. The lower electrode 120 may be made of a material selected from the group consisting of indium tin oxide (ITO), fluorinated tin oxide (FTO), indium zinc oxide (IZO), Al-doped zinc oxide (AZO), indium zinc tin oxide (IZTO), $SnO_2$, ZnO, carbon nanotubes, graphene, and silver nanowires. The lower electrode 120 is preferably made of indium tin oxide (ITO).

According to one embodiment of the present invention, the surface modified layer 120a made of polyethylenimine ethoxylated (PEIE) is preferably formed to a thickness of 1 to 20 nm on the lower electrode 120.

The PEIE surface modified layer 120a formed on the lower electrode 120 has the effect to lower the work function of the lower electrode 120 due to the surface dipole of the amine ($NH_2$) groups included in the PEIE. The amine groups chemically interact with the photoactive layer 130 formed on the PEIE surface modified layer 120a to improve the adhesion between the lower electrode 120 and the photoactive layer 130.

The formation of the PEIE surface modified layer 120a on the lower electrode 120 can contribute to improvement of the adhesion between the lower electrode 120 and the photoactive layer 130. The PEIE surface modified layer 120a lowers the work function of the lower electrode 120, allowing the use of the lower electrode 120 as a cathode.

The photoactive layer 130 has a bulk heterojunction (BHJ) structure in which an electron donating material and an electron accepting material are mixed together. As described above, the photoactive layer 130 includes (a) a p-type organic semiconductor material, (b) an n-type organic semiconductor material, and (c) a solvent.

The p-type organic semiconductor material (a) includes (a-1) a first organic semiconductor material represented by Formula 1:

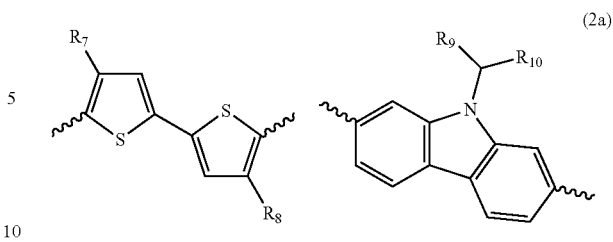

wherein $R_7$, $R_8$, $R_9$, and $R_{10}$ may be the same or different and are each independently H or a $C_1$-$C_{22}$ linear or branched alkyl group.

It is preferred that when $R_1$ and $R_2$ in Formula 1 are symmetric and have the same structure, $R_3$ and $R_4$ in Formula 1 are symmetric and have the same structure and $R_5$ and $R_6$ in Formula 2 are symmetric and have the same structure. Such structures of the first and second organic semiconductor materials are advantageous for intermolecular energy transfer.

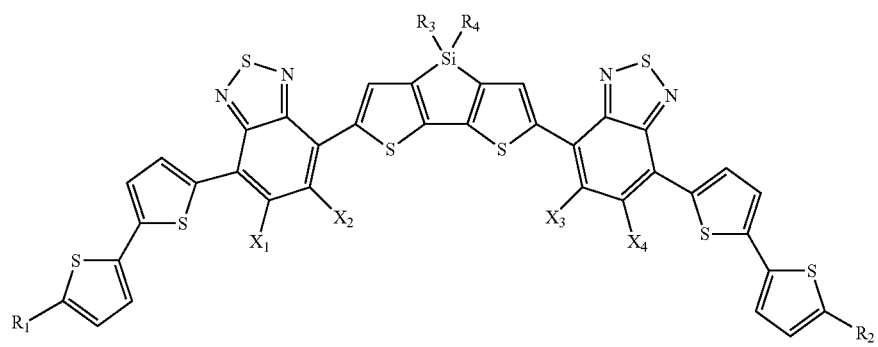

(1)

wherein $X_1$, $X_2$, $X_3$, and $X_4$ may be the same or different and are each independently hydrogen or a halogen and $R_1$, $R_2$, $R_3$, and $R_4$ may be the same or different and are each independently a $C_1$-$C_{22}$ linear or branched alkyl group, and (a-2) a second organic semiconductor material represented by Formula 2:

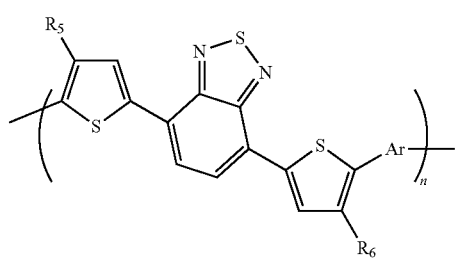

wherein $R_5$ and $R_6$ may be the same or different and are each independently H or a $C_1$-$C_{22}$ linear or branched alkyl group, n is an integer from 1 to 10,000,000, and Ar is selected from aromatic groups having the following structures 2a:

It is most preferred that $R_1$ and $R_2$ in Formula 1 are the same or different and are each independently a $C_1$-$C_7$ linear alkyl group, $R_3$ and $R_4$ in Formula 1 are the same or different and are each independently a $C_8$-$C_{22}$ branched alkyl group, and $R_5$ and $R_6$ in Formula 2 are the same or different and are each independently H or a $C_8$-$C_{22}$ branched alkyl group. When the first organic semiconductor material is mixed with the second organic semiconductor materials, their side chains provide the most improved intermolecular stacking and supramolecular alignment.

The above-described effects are most profound when $R_1$ and $R_2$ in Formula 1 are symmetric and have the same structure, $R_3$ and $R_4$ in Formula 1 are symmetric and have the same structure, $R_5$ and $R_6$ in Formula 2 are symmetric and have the same structure, $R_7$ and $R_8$ in Formula 2a are the same or different and are each independently H or a $C_8$-$C_{22}$ linear alkyl group, and $R_9$ and $R_{10}$ in Formula 2a are the same or different and are each independently H or a $C_8$-$C_{22}$ branched alkyl group.

In particular, $X_1$, $X_2$, $X_3$, and $X_4$ in Formula 1 are the same or different and are each independently hydrogen or F.

In other words, considering that the photoactive layer 130 is formed using a solution of the first organic semiconductor material (a-1) represented by Formula 1, the second organic semiconductor material (a-2) represented by Formula 2, and the n-type organic semiconductor material (b) in the solvent (c), it includes the first organic semiconductor material (a-1) represented by Formula 1, the second organic semiconductor material (a-2) represented by Formula 2, the n-type organic semiconductor material (b), and the solvent (c).

The photoactive layer 130 having a bulk-heterojunction structure is formed by a solution process. The solution process may be selected from the group consisting of spin coating, ink-jet printing, doctor blade coating, electrospray, dip coating, and screen printing. The solution process is preferably spin coating.

The characteristics (such as uniformity and morphology) of the photoactive layer 130 have the greatest influence on the performance of the organic solar cell and are dependent on such factors as the mixing weight ratio between the first organic semiconductor material (a-1) and the second organic semiconductor material (a-2) and the kind and content of the solvent. Accordingly, the numerical limitations and kinds of these components are of great significance in the performance of the organic solar cell.

The first organic semiconductor material (a-1) represented by Formula 1 is a low molecular weight compound having a molecular weight of 1000 to 2000 g/mol and the second organic semiconductor material (a-2) represented by Formula 2 is a high molecular weight compound having a molecular weight 50,000 to 100,000 g/mol.

When an appropriate amount of the second organic semiconductor material (a-2) represented by Formula 2 is mixed with the low molecular weight compound as the first organic semiconductor material (a-1) represented by Formula 1, the first organic semiconductor material is inhibited from aggregating, resulting in improvements in the morphology of the photoactive layer and the network structure of the first organic semiconductor material (a-1) represented by Formula 1. As a result, the photoelectric conversion efficiency of the organic solar cell is improved by at least 1% while maintaining the hole mobility and absorbance of the organic solar cell at high levels.

The organic solar cell may have the most optimized structure of prior art small molecule organic solar cells. Also in this case, the introduction of the photoactive layer can improve the efficiency of the organic solar cell by a maximum of at least 1%, as confirmed in the Experimental Examples section that follows. That is, the use of the photoactive layer including the first organic semiconductor material (a-1) represented by Formula 1 and the second organic semiconductor material (a-2) represented by Formula 2 in a small molecule organic solar cell having an optimized structure is very effective in achieving further improved photoelectric conversion efficiency.

The first organic semiconductor material (a-1) may be selected from the low molecular weight compounds represented by Formulae 3 to 7:

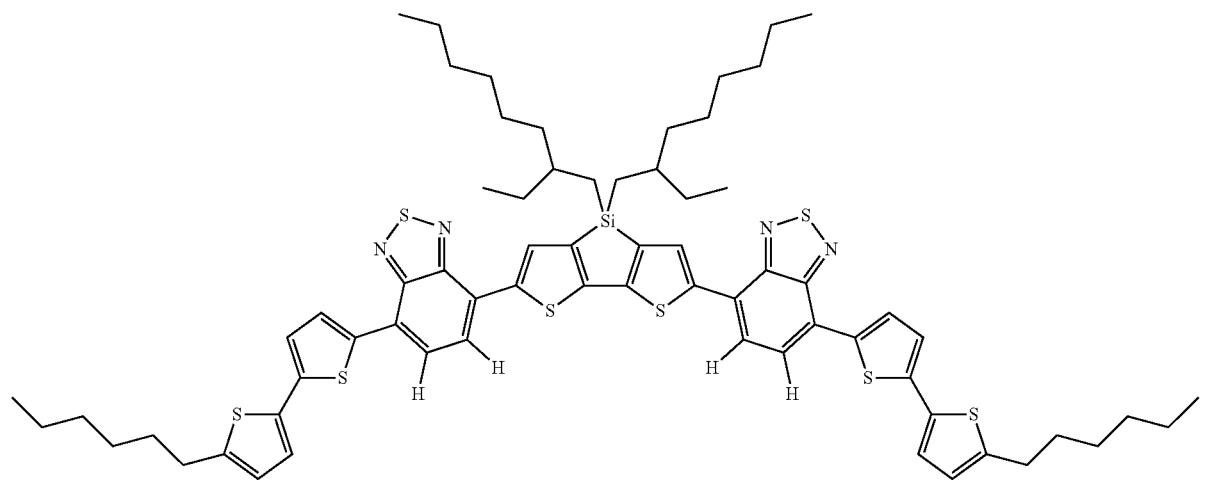

(3)

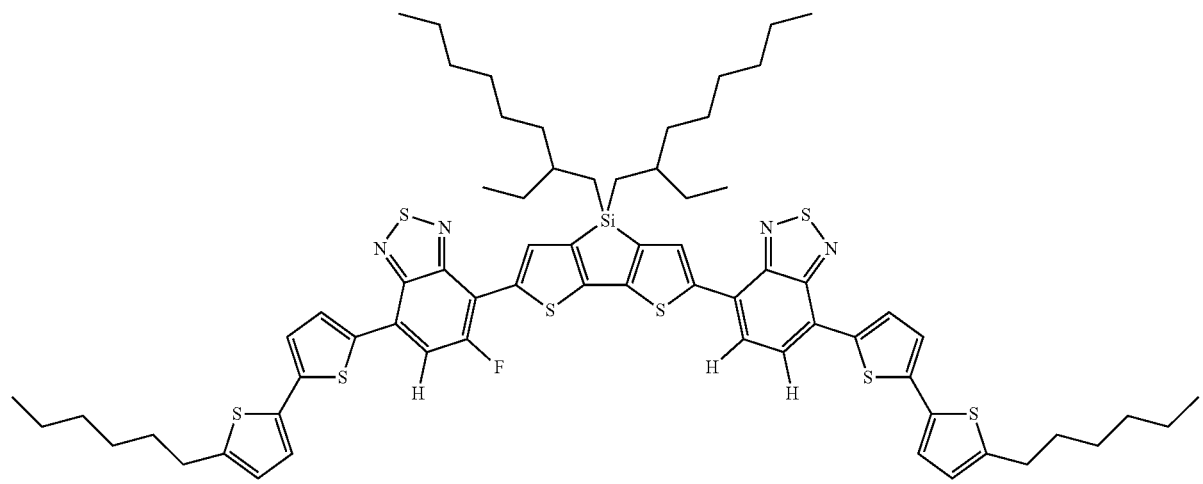

(4)

-continued
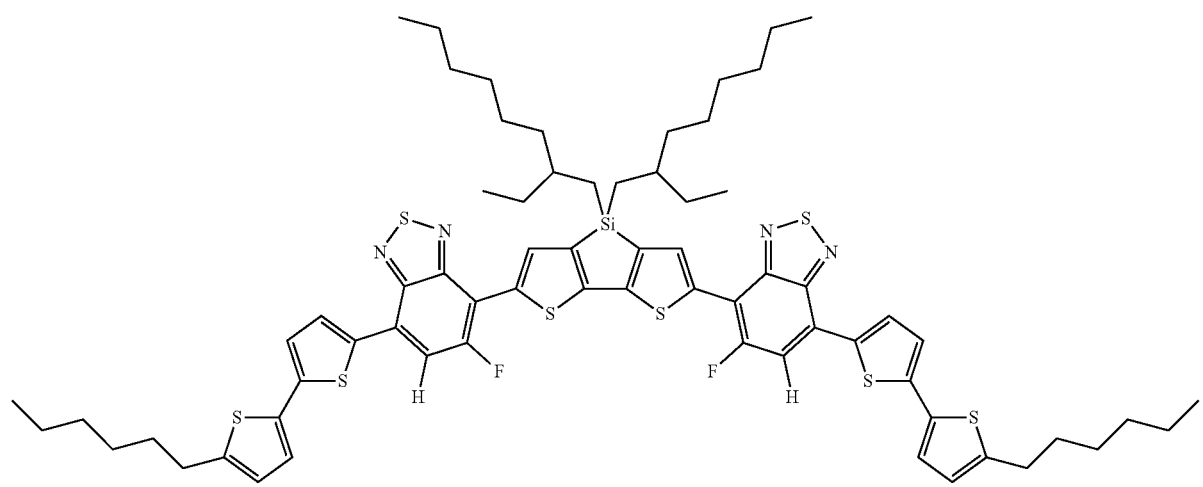
(5)
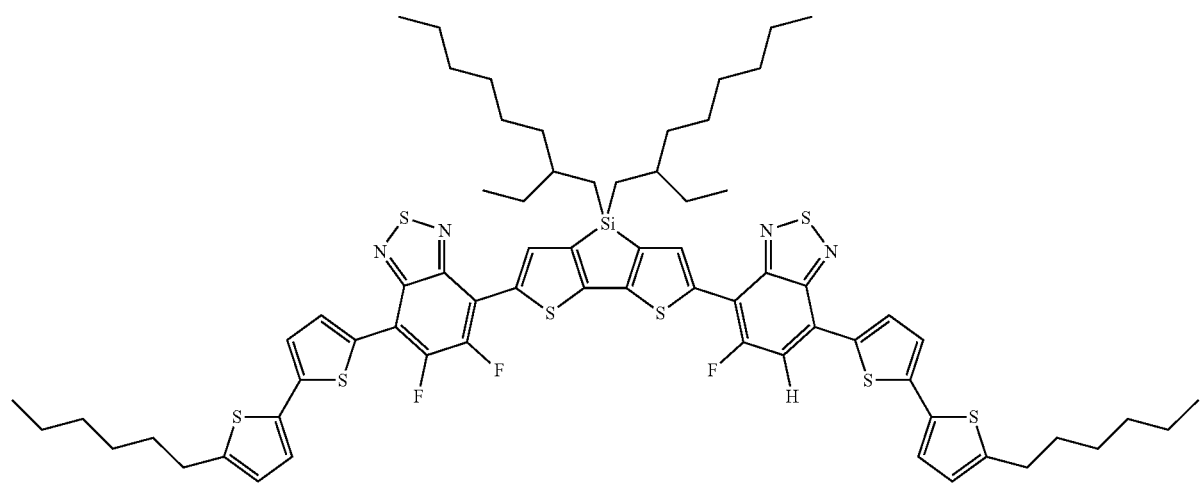
(6)
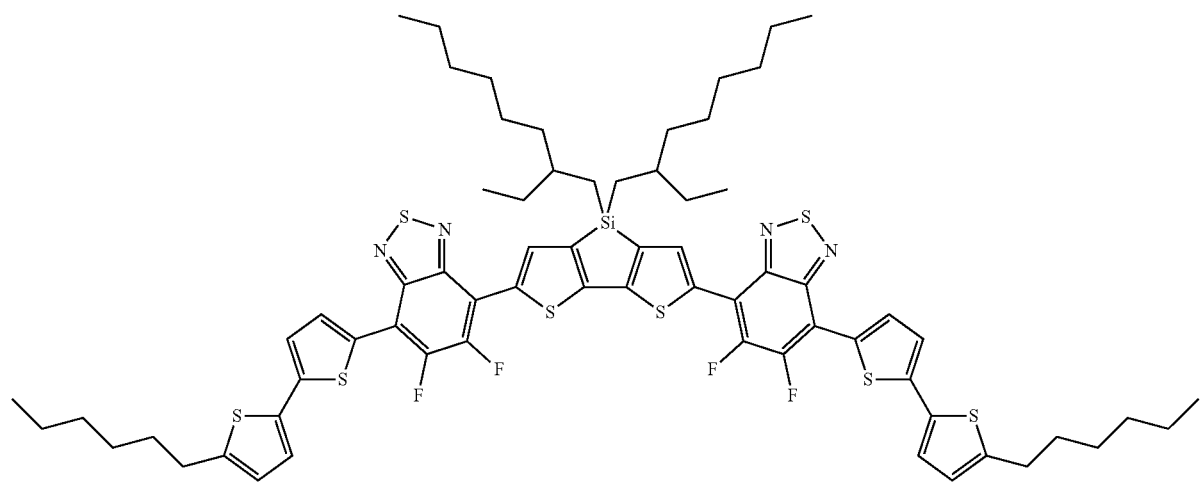
(7)

Preferably, the first organic semiconductor material (a-1) is the low molecular weight compound represented by Formula 5.

The second organic semiconductor material (a-2) may be a high molecular weight compound represented by Formula 8 or 9:

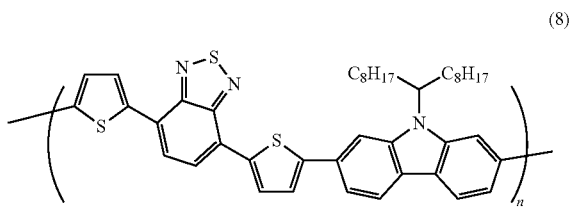

(8)

wherein n is an integer from 1 to 10,000,000,

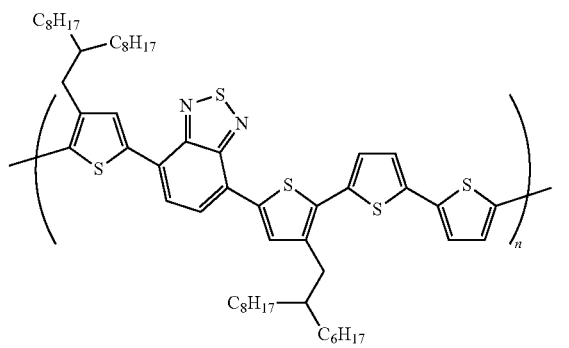

(9)

wherein n is an integer from 1 to 10,000,000.

Preferably, the second organic semiconductor material has a molecular weight of 50000 to 100000 g/mol.

The first organic semiconductor material (a-1) may be mixed with the second organic semiconductor material (a-2) in a weight ratio of 1:0.01-0.04. If the mixing weight ratio of the first organic semiconductor material (a-1) to the second organic semiconductor material is 1:<0.01, the morphology of the photoactive layer cannot be effectively improved, making it impossible to expect an improvement in the photoelectric conversion efficiency of the organic solar cell. Meanwhile, if the mixing weight ratio of the first organic semiconductor material (a-1) to the second organic semiconductor material is 1:≥0.05, the efficiency of the organic solar cell is drastically reduced by at least about 2.5 times. It is thus preferred to limit the mixing weight ratio to the range defined above.

The solvent (c) is preferably a mixture of chlorobenzene and 1,8-diiodooctane. The use of other solvents significantly reduces the photoelectric conversion efficiency to 1% or less, with a maximum of 2% or less, as confirmed in the following Experimental Examples section.

The mixing volume ratio of the chlorobenzene to the 1,8-diiodooctane is preferably 1:0.002-5.

In conclusion, the most preferred composition of the photoactive layer 130 in the organic solar cell of the present invention is obtained when the first organic semiconductor material (a-1) represented by Formula 1 is mixed with the second organic semiconductor material (a-2) represented by Formula 2 in a weight ratio of 1:0.01-0.04 and the solvent (c) is a mixture of chlorobenzene and 1,8-diiodooctane in a volume ratio of 1:0.002-5. If any one of these relations is not satisfied, the photoelectric conversion efficiency is significantly lowered, which was confirmed in the following Experimental Examples section.

The introduction of the photoactive layer 130 satisfying the above relations can further improve the photoelectric conversion efficiency of the organic solar cell by a minimum of 0.1% and by a maximum of 1% or more although the structure of the organic solar cell is already optimized.

The further improved photoelectric conversion efficiency of the optimized organic solar cell is regarded as significant in the art. The significantly (≥1%) improved efficiency demonstrates that the present invention has a noticeable effect.

If the mixing weight ratio between the first organic semiconductor material (a-1) represented by Formula 1 and the second organic semiconductor material (a-2) represented by Formula 2 in the photoactive layer 130 is outside the range defined above, the desired effect of the present invention cannot be achieved and the photoelectric conversion efficiency is lowered, making it meaningless to use the first organic semiconductor material (a-1) represented by Formula 1 in admixture with the second organic semiconductor material (a-2) represented by Formula 2.

The n-type organic semiconductor material (b) may be selected from the group consisting of methyl (6,6)-phenyl-C61-butyrate ($PC_{60}BM$), (6,6)-phenyl-C61-butyric acid methyl ester ($C_{60}$-PCBM), (6,6)-phenyl-C71-butyric acid methyl ester ($C_{70}$-PCBM), (6,6)-phenyl-C77-butyric acid methyl ester ($C_{76}$-PCBM), (6,6)-phenyl-C79-butyric acid methyl ester ($C_{78}$-PCBM), (6,6)-phenyl-C81-butyric acid methyl ester ($C_{80}$-PCBM), (6,6)-phenyl-C83-butyric acid methyl ester ($C_{82}$-PCBM), (6,6)-phenyl-C85-butyric acid methyl ester ($C_{84}$-PCBM), bis(1-[3-(methoxycarbonyl)propyl]-1-phenyl) (Bis-$C_{60}$-PCBM), 3'-phenyl-3'H-cyclopropa(8,25)(5,6)fullerene-C70-bis-D5h(6)-3'-butyric acid methyl ester (Bis-$C_{70}$-PCBM), indene-C60-bisadduct (ICBA), monoindenyl C60 (ICMA), and combinations thereof. The n-type organic semiconductor material (b) is most preferably (6,6)-phenyl-C71-butyric acid methyl ester ($C_{70}$-PCBM).

According to one embodiment of the present invention, the upper electrode may be made of, for example, $MoO_3$/Ag, Au or Pt.

Most preferably, the organic solar cell of the present invention has a typical structure in which the ITO layer and the PEIE surface modified layer are sequentially formed on a substrate, the photoactive layer is formed by coating a solution of the low molecular weight compound and the high molecular weight compound in the solvent on the polymer surface modified layer, and the upper electrode made of $MoO_3$/Ag is formed on the photoactive layer.

A further aspect of the present invention is directed to a method for fabricating an organic solar cell, including:

I) forming a lower electrode on a substrate;

II) mixing (a-1) a first organic semiconductor material represented by Formula 1:

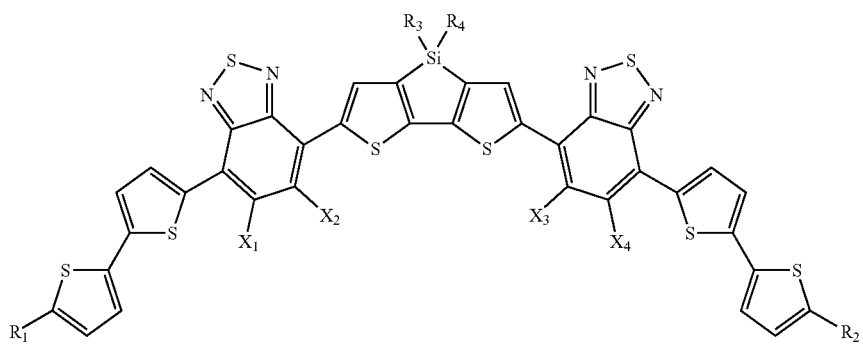

(1)

wherein $X_1$, $X_2$, $X_3$, and $X_4$ may be the same or different and are each independently hydrogen or a halogen and $R_1$, $R_2$, $R_3$, and $R_4$ may be the same or different and are each independently a $C_1$-$C_{22}$ linear or branched alkyl group, (a-2) a second organic semiconductor material represented by Formula 2:

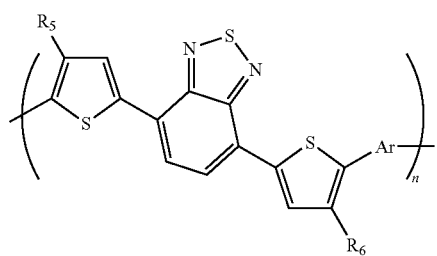

(2)

wherein $R_5$ and $R_6$ may be the same or different and are each independently H or a $C_1$-$C_{22}$ linear or branched alkyl group, n is an integer from 1 to 10,000,000, and Ar is selected from aromatic groups having the following structures 2a:

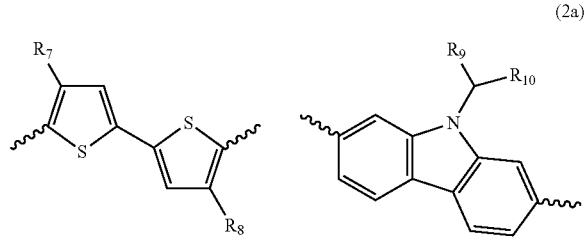

(2a)

wherein $R_7$, $R_8$, $R_9$, and $R_{10}$ may be the same or different and are each independently H or a $C_1$-$C_{22}$ linear or branched alkyl group, (b) an n-type organic semiconductor material, and (c) a solvent to prepare a first solution;

III) coating the first solution on the lower electrode to form a photoactive layer; and IV) forming an upper electrode on the photoactive layer.

Below is a more detailed description of the method according to the present invention.

First, a lower electrode is formed on a substrate (step I)). The lower electrode may be formed by a deposition technique.

The deposition technique is not particularly limited and may be any of those known in the art. The deposition technique is preferably selected from the group consisting of chemical vapor deposition and physical vapor deposition. Particularly preferred is sputtering by which the lower electrode can be rapidly deposited on a large area at relatively low temperature.

For example, the substrate may be made of a material selected from glass, polycarbonate (PC), polyethylene terephthalate (PET), polyethylene naphthalate (PEN), and polyether sulfonate (PES). More preferably, the substrate is a glass substrate.

The lower electrode may be an anode or a cathode. The lower electrode may be made of a material selected from the group consisting of indium tin oxide (ITO), fluorinated tin oxide (FTO), indium zinc oxide (IZO), Al-doped zinc oxide (AZO), indium zinc tin oxide (IZTO), $SnO_2$, ZnO, carbon nanotubes, graphene, and silver nanowires. The lower electrode is preferably made of indium tin oxide (ITO).

The method may further include I-1) forming a polyethylenimine ethoxylated (PEIE) surface modified layer on the lower electrode after step I) and prior to step II).

The PEIE surface modified layer may be formed by spin coating a solution of PEIE on the lower electrode.

The PEIE surface modified layer has the effect to lower the work function of an underlying electrode. This effect enables the use of the lower electrode even when the lower electrode has a high work function. Accordingly, the PEIE surface modified layer can provide a solution to the problem of short lifetime caused by the use of a low work function electrode. That is, the PEIE surface modified layer is effective in improving the lifetime of the organic solar cell.

The PEIE surface modified layer may be formed using polyethylenimine ethoxylated (PEIE) and is preferably from 1 to 20 nm in thickness.

The PEIE surface modified layer formed on the lower electrode has the effect to lower the work function of the lower electrode due to the surface dipole of the amine ($NH_2$) groups included in the PEIE. The amine groups chemically interact with a photoactive layer to be formed on the PEIE surface modified layer to improve the adhesion between the lower electrode and the photoactive layer.

The method may further include I-2) drying the PEIE surface modified layer at 80 to 130° C. for 5 to 15 minutes after step I-1).

Next, (a-1) a first organic semiconductor material represented by Formula 1:

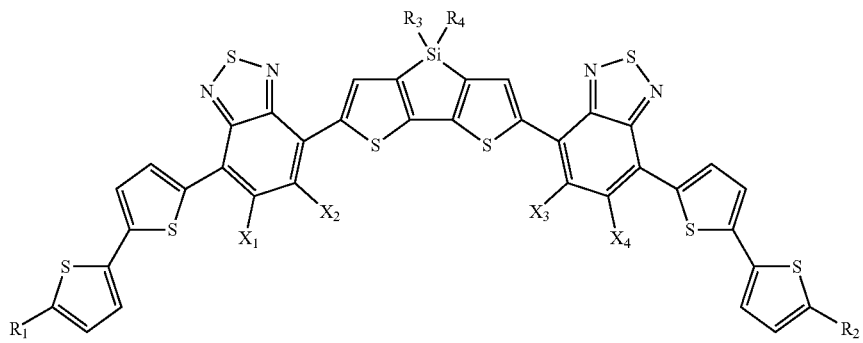

(1)

wherein $X_1$, $X_2$, $X_3$, and $X_4$ may be the same or different and are each independently hydrogen or a halogen and $R_1$, $R_2$, $R_3$, and $R_4$ may be the same or different and are each independently a $C_1$-$C_{22}$ linear or branched alkyl group, (a-2) a second organic semiconductor material represented by Formula 2:

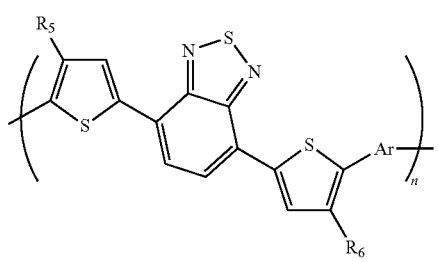

(2)

wherein $R_5$ and $R_6$ may be the same or different and are each independently H or a $C_1$-$C_{22}$ linear or branched alkyl group, n is an integer from 1 to 10,000,000, and Ar is selected from aromatic groups having the following structures 2a:

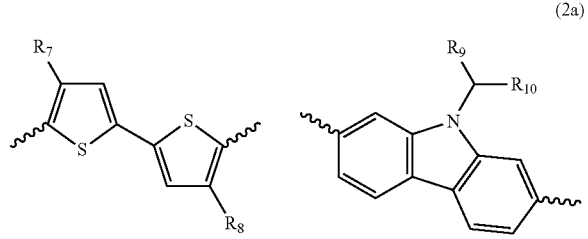

(2a)

wherein $R_7$, $R_8$, $R_9$, and $R_{10}$ may be the same or different and are each independently H or a $C_1$-$C_{22}$ linear or branched alkyl group, (b) an n-type organic semiconductor material, and (c) a solvent are mixed to prepare a first solution (step II)). Thereafter, the first solution is coated on the lower electrode to form a photoactive layer (step III)).

It is preferred that when $R_1$ and $R_2$ in Formula 1 are symmetric and have the same structure, $R_3$ and $R_4$ in Formula 1 are symmetric and have the same structure and $R_5$ and $R_6$ in Formula 2 are symmetric and have the same structure. Such structures of the first and second organic semiconductor materials are advantageous for intermolecular energy transfer.

It is most preferred that $R_1$ and $R_2$ in Formula 1 are the same or different and are each independently a $C_1$-$C_7$ linear alkyl group, $R_3$ and $R_4$ in Formula 1 are the same or different and are each independently a $C_8$-$C_{22}$ branched alkyl group, and $R_5$ and $R_6$ in Formula 2 are the same or different and are each independently H or a $C_8$-$C_{22}$ branched alkyl group. When the first organic semiconductor material is mixed with the second organic semiconductor materials, their side chains provide the most improved intermolecular stacking and supramolecular alignment.

The above-described effects are most profound when $R_1$ and $R_2$ in Formula 1 are symmetric and have the same structure, $R_3$ and $R_4$ in Formula 1 are symmetric and have the same structure, $R_5$ and $R_6$ in Formula 2 are symmetric and have the same structure, $R_7$ and $R_8$ in Formula 2a are the same or different and are each independently H or a $C_8$-$C_{22}$ linear alkyl group, and $R_9$ and $R_{10}$ in Formula 2a are be the same or different and are each independently H or a $C_8$-$C_{22}$ branched alkyl group.

In particular, $X_1$, $X_2$, $X_3$, and $X_4$ in Formula 1 are the same or different and are each independently hydrogen or F.

The characteristics (such as uniformity and morphology) of the photoactive layer have the greatest influence on the performance of the organic solar cell and are dependent on such factors as the mixing weight ratio between the first organic semiconductor material (a-1) and the second organic semiconductor material (a-2) and the kind and content of the solvent. Accordingly, such factors of the photoactive layer are very important in the performance of the organic solar cell.

The first organic semiconductor material (a-1) is a low molecular weight compound having a molecular weight of 1000 to 2000 g/mol and the second organic semiconductor material (a-2) is a high molecular weight compound having a molecular weight of 50,000 to 100,000 g/mol.

When an appropriate amount of the second organic semiconductor material (a-2) represented by Formula 2 is mixed with the low molecular weight compound as the first organic semiconductor material (a-1) represented by Formula 1, the first organic semiconductor material is inhibited from aggregating, resulting in improvements in the morphology of the photoactive layer and the network structure of the first organic semiconductor material (a-1) represented by Formula 1. As a result, the photoelectric conversion efficiency of the organic solar cell is improved by at least 1% while maintaining the hole mobility and absorbance of the organic solar cell at high levels.

The first organic semiconductor material (a-1) may be selected from the low molecular weight compounds represented by Formulae 3 to 7:

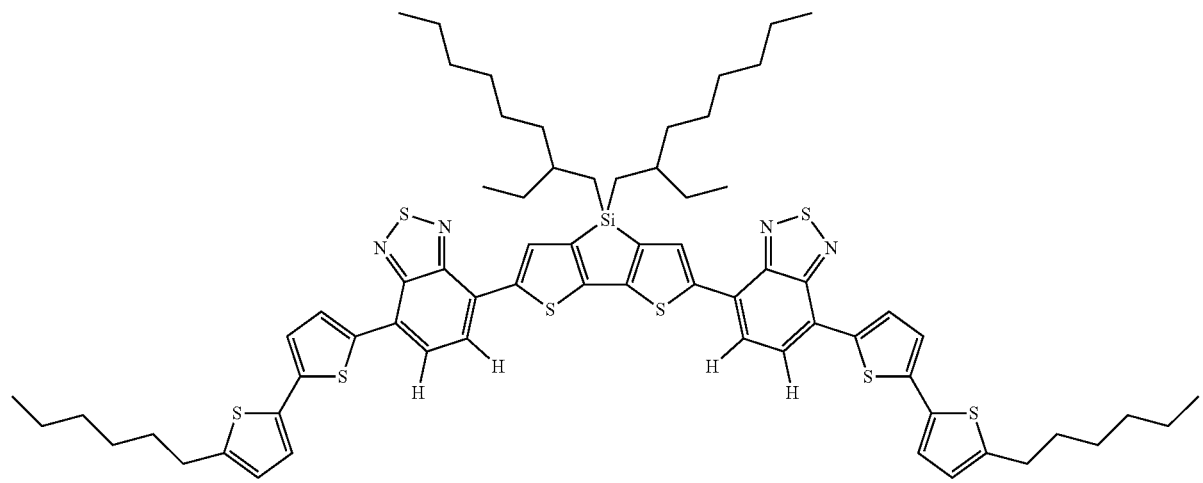
(3)
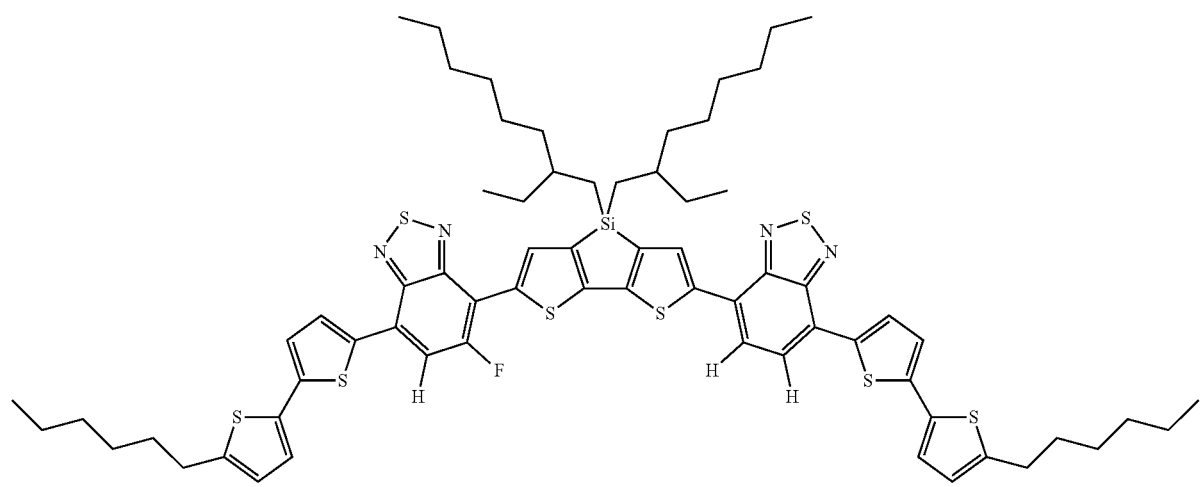
(4)
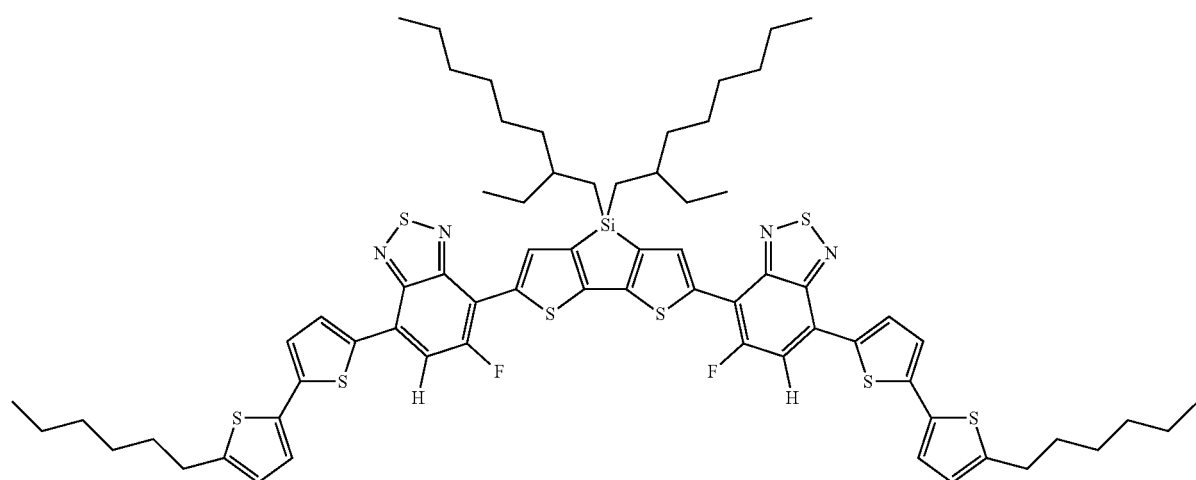
(5)

(6)

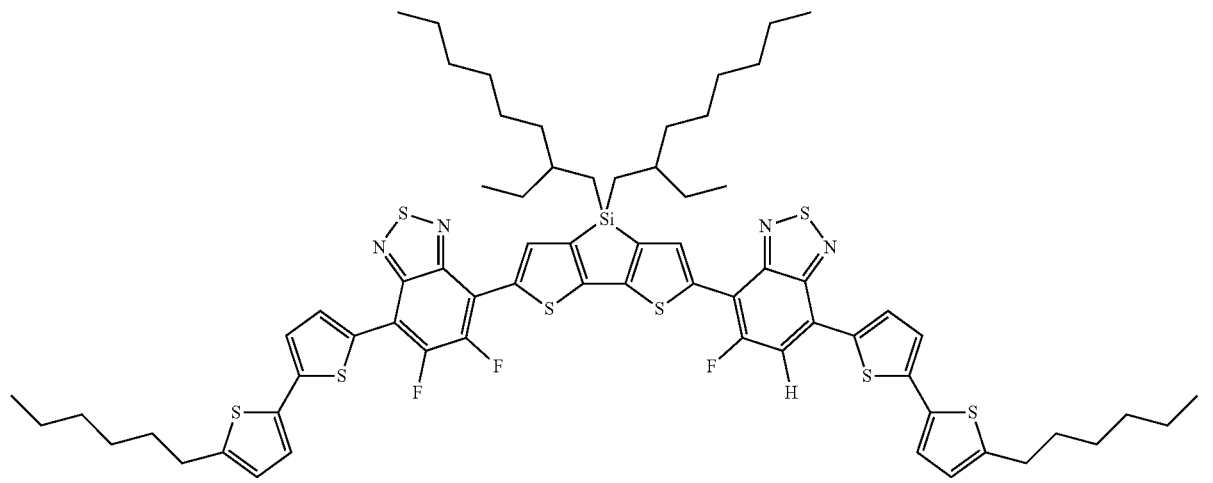

(7)

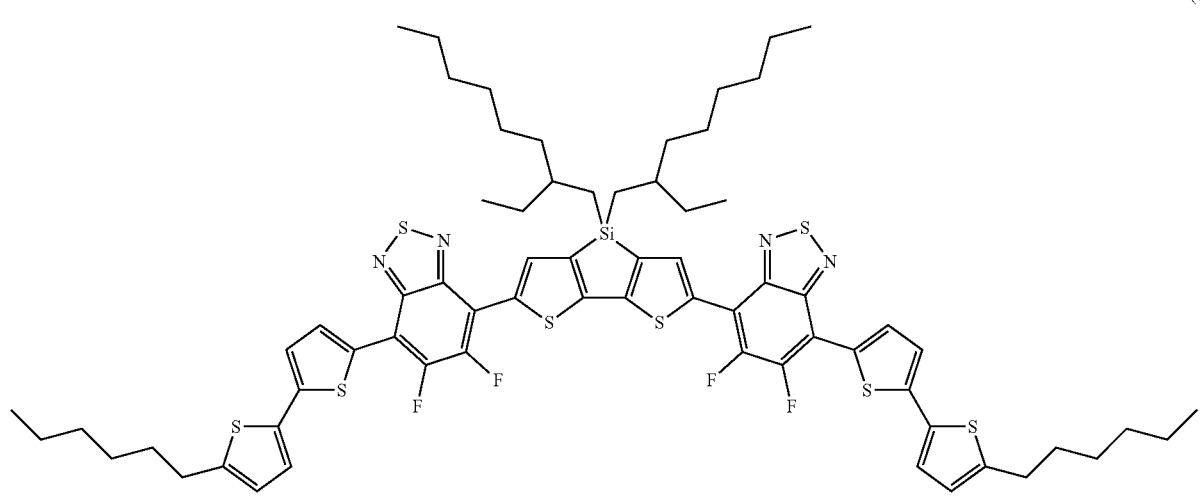

Preferably, the first organic semiconductor material (a-1) is the low molecular weight compound represented by Formula 5.

The second organic semiconductor material (a-2) may be a high molecular weight compound represented by Formula 8 or 9:

(8)

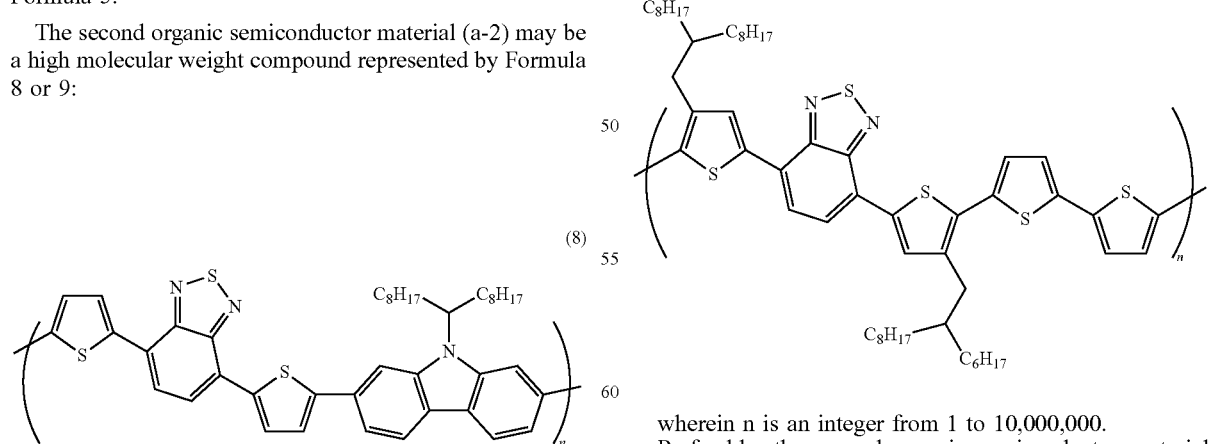

wherein n is an integer from 1 to 10,000,000, wherein n is an integer from 1 to 10,000,000.

Preferably, the second organic semiconductor material has a molecular weight of 50000 to 100000 g/mol.

The first organic semiconductor material (a-1) is preferably mixed the second organic semiconductor material (a-2) in a weight ratio of 1:0.01-0.04. If the mixing weight ratio of the first organic semiconductor material (a-1) to the second organic semiconductor material is 1:<0.01, the morphology of the photoactive layer cannot be effectively improved, making it impossible to expect an improvement in the photoelectric conversion efficiency of the organic solar cell. Meanwhile, if the mixing weight ratio of the first organic semiconductor material (a-1) to the second organic semiconductor material is 1:≥0.05, the efficiency of the organic solar cell is drastically reduced by at least about 2.5 times. It is thus preferred to limit the mixing weight ratio to the range defined above.

The solvent (c) is preferably a mixture of chlorobenzene and 1,8-diiodooctane. The use of other solvents significantly reduces the photoelectric conversion efficiency to 1% or less, with a maximum of 2% or less, as confirmed in the following Experimental Examples section.

The mixing volume ratio of the chlorobenzene to the 1,8-diiodooctane is preferably 1:0.002-5.

In conclusion, the most preferred composition of the first solution for the formation of the photoactive layer in the method of the present invention is obtained when the mixing weight ratio of the first organic semiconductor material (a-1) represented by Formula 1 to the second organic semiconductor material (a-2) represented by Formula 2 in a weight ratio is 1:0.01-0.04 and the solvent (c) is a mixture of chlorobenzene and 1,8-diiodooctane in a volume ratio of 1:0.002-5. If any one of these relations is not satisfied, the performance of the organic solar cell is significantly lowered, which was confirmed in the following Experimental Examples section.

The use of the first solution satisfying the above relations can further improve the photoelectric conversion efficiency of the organic solar cell by a minimum of 0.1% and by a maximum of 1% or more although the structure of the organic solar cell is already optimized.

If the mixing weight ratio between the first organic semiconductor material (a-1) represented by Formula 1 and the second organic semiconductor material (a-2) represented by Formula 2 in the photoactive layer is outside the range defined above, the desired effect of the present invention cannot be achieved and the photoelectric conversion efficiency of the organic solar cell is lowered, making it meaningless to use the first organic semiconductor material (a-1) represented by Formula 1 in admixture with the second organic semiconductor material (a-2) represented by Formula 2.

The n-type organic semiconductor material (b) may be selected from the group consisting of methyl (6,6)-phenyl-C61-butyrate ($PC_{60}BM$), (6,6)-phenyl-C61-butyric acid methyl ester ($C_{60}$-PCBM), (6,6)-phenyl-C71-butyric acid methyl ester ($C_{70}$-PCBM), (6,6)-phenyl-C77-butyric acid methyl ester ($C_{76}$-PCBM), (6,6)-phenyl-C79-butyric acid methyl ester ($C_{78}$-PCBM), (6,6)-phenyl-C81-butyric acid methyl ester ($C_{80}$-PCBM), (6,6)-phenyl-C83-butyric acid methyl ester ($C_{82}$-PCBM), (6,6)-phenyl-C85-butyric acid methyl ester ($C_{84}$-PCBM), bis(1-[3-(methoxycarbonyl)propyl]-1-phenyl) (Bis-$C_{60}$-PCBM), 3'-phenyl-3'H-cyclopropa(8,25)(5,6)fullerene-C70-bis-D5h(6)-3'-butyric acid methyl ester (Bis-$C_{70}$-PCBM), indene-C60-bisadduct (ICBA), monoindenyl C60 (ICMA), and combinations thereof. The n-type organic semiconductor material (b) is most preferably (6,6)-phenyl-C71-butyric acid methyl ester ($C_{70}$-PCBM).

In step III), the photoactive layer may be formed by coating the first solution on the lower electrode or the PEIE surface modified layer.

The coating may be selected from the group consisting of spin coating, nozzle coating, spray coating, inkjet coating, and slit coating. Spin coating is preferred.

Finally, an upper electrode is formed on the photoactive layer (step IV)). The formation of the upper electrode on the photoactive layer may be accomplished by any suitable technique known in the art.

According to one embodiment of the present invention, the upper electrode may be made of, for example, $MoO_3$/Ag, Au or Pt.

The formation of the photoactive layer using the first solution allows the organic solar cell to have high photoelectric conversion efficiency and enables the fabrication of the organic solar cell in a simpler manner.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not presented. It will also be understood that such modifications and variations are intended to come within the scope of the appended claims.

The experimental results presented herein are merely representative results of the following examples and comparative examples and the effects of the exemplary embodiments of the present invention are specifically described in the respective sections although they are not explicitly presented below.

Synthesis Example 1: Compound Represented by Formula 3 (DTS-0F): 7,7'-(4,4-bis-ethylhexyl)-4H-silolo[3,2-b:4,5-b']dithiophene-2,6-diyl)bis(4-(5'-hexyl-[2,2'-bithiophen]-5-yl)benzo[c][1,2,5]thiadiazole)

Reaction Scheme 1

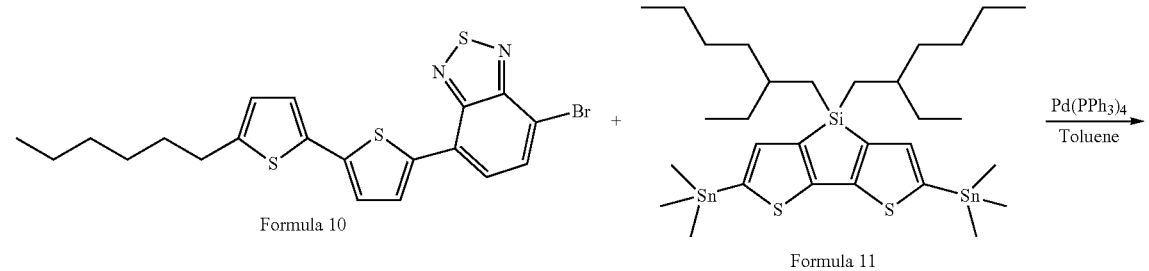

Formula 10

Formula 11

-continued

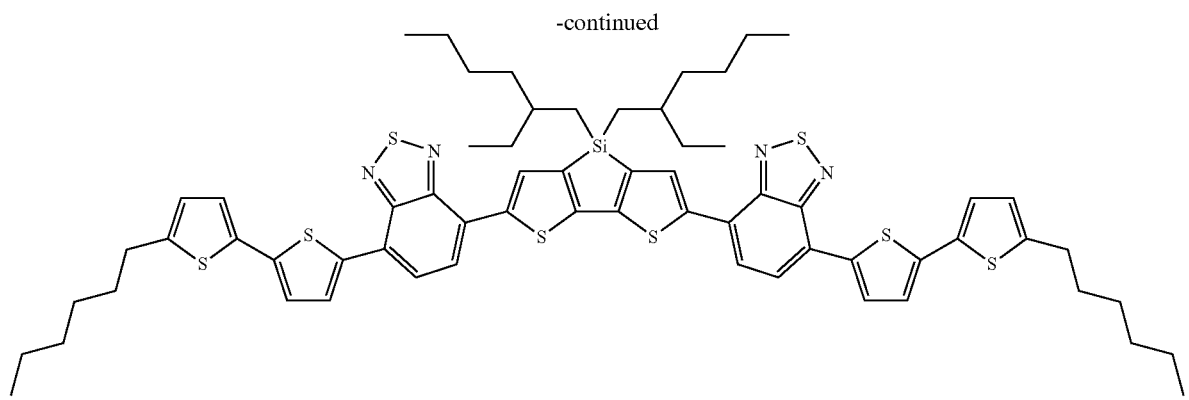

Formula 3

A 15 ml reaction tube was evacuated and flame dried at least 3 times to remove moisture therefrom. After the addition of the compound represented by Formula 10 (0.55 g, 1.18 mmol) and the compound represented by Formula 11 (0.40 g, 0.54 mmol), vacuuming and venting were repeated 3 times to create a nitrogen atmosphere in the reaction tube. Purified toluene (5.4 ml) and Pd(PPh$_3$)$_4$ (0.062 g, 0.05 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 0.504 g (yield 86%) of the compound represented by Formula 3. The above reaction procedure is shown in Reaction Scheme 1.

$^1$H NMR (400 MHz, CDCl$_3$): δ=8.19 (t, 2H), 8.00 (d, 2H), 7.78 (m, 4H), 7.16 (d, 2H), 7.09 (d, 2H), 6.71 (d, 2H), 2.81 (t, 4H), 1.68 (m, 4H), 1.38-1.09 (m, 34H), 0.92-0.81 (m, 18H).

Synthesis Example 2: Compound Represented by Formula 4

2-1) Synthesis of Compound Represented by Formula 14: 4-(4,4-bis(2-ethylhexyl)-4H-silolo[3,2-b:4,5-b']dithiophen-2-yl)-5-fluoro-7-(5'-hexyl-[2,2'-bithiophen]-5-yl)benzo[c][1,2,5]thiadiazole Reaction Scheme 2

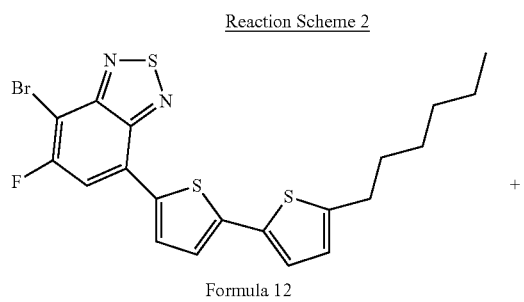

Formula 12

+

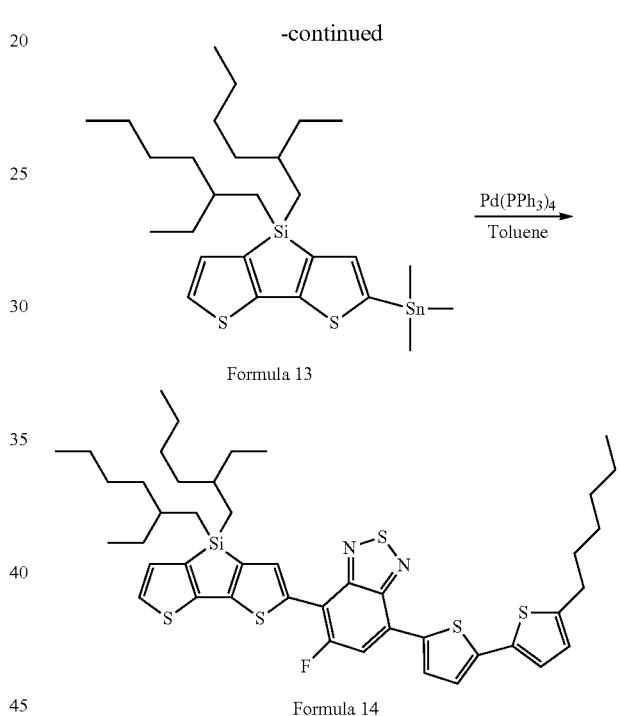

Formula 13

Formula 14

A 15 ml reaction tube was evacuated and flame dried at least 3 times to remove moisture therefrom. After the addition of the compound represented by Formula 12 (0.87 g, 1.51 mmol) and the compound represented by Formula 13 (0.60 g, 1.25 mmol), vacuuming and venting were repeated 3 times to create a nitrogen atmosphere in the reaction tube. Purified toluene (7.4 ml) and Pd(PPh$_3$)$_4$ (0.071 g, 0.06 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 0.85 g (yield 82.6%) of the compound represented by Formula 14. The above reaction procedure is shown in Reaction Scheme 2.

$^1$H NMR (400 MHz, CDCl$_3$): δ=8.28 (t, 1H), 8.03 (d, 1H), 7.73 (d, 1H), 7.27 (d, 1H), 7.19 (d, 1H), 7.12 (d, 1H), 7.08 (d, 1H), 6.73 (d, 1H), 2.82 (t, 2H), 1.70 (m, 2H), 1.47-0.97 (m, 28H) 0.96-0.76 (m, 15H).

2-2) Synthesis of Compound Represented by Formula 14 (DTS-1F): 4-(4,4-bis(2-ethylhexyl)-6-(7-(5'-hexyl-[2,2'-bithiophen]-5-yl)benzo [c][1,2,5]thiadiazol-4-yl)-4H-silolo[3,2-b:4,5-b']dithiophen-2-yl)-5-fluoro-7-(5'-hexyl-[2,2'-bithiophen]-5-yl)benzo[c][1,2,5]thiadiazole)

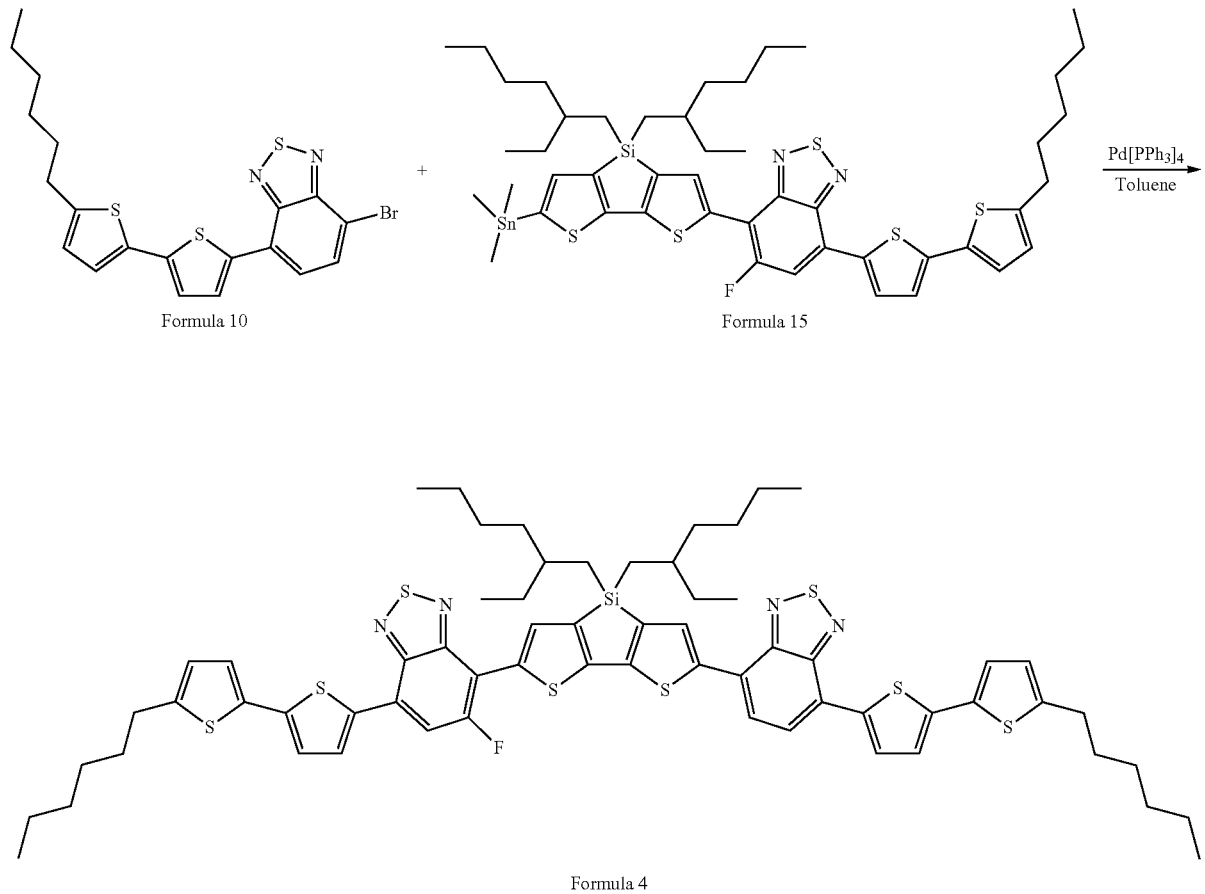

Reaction Scheme 3

Formula 10

Formula 15

Formula 4

A 15 ml reaction tube was evacuated and flame dried at least 3 times to remove moisture therefrom. After the addition of the compound represented by Formula 10 (0.26 g, 0.56 mmol) and the compound represented by Formula 15 (0.53 g, 0.54 mmol), vacuuming and venting were repeated 3 times to create a nitrogen atmosphere in the reaction tube. Purified toluene (7.7 ml) and Pd(PPh$_3$)$_4$ (0.031 g, 0.02 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 0.461 g (yield 71%) of the compound represented by Formula 4 (DTS-1F). The above reaction procedure is shown in Reaction Scheme 3.

$^1$H NMR (400 MHz, CDCl$_3$): δ=8.33 (t, 1H), 8.20 (t, 1H), 8.03-8.01 (m, 2H), 7.82 (m, 2H), 7.70 (d, 1H), 7.18-7.17 (m, 2H), 7.12-7.10 (m, 2H), 6.73-6.71 (m, 2H), 2.84-2.80 (m, 4H), 1.74-1.67 (m, 4H), 1.42-1.05 (m, 34H), 0.92-0.80 (m, 18H).

Synthesis Example 3: Synthesis of Compound Represented by Formula 5

3-1) Synthesis of Compound Represented by Formula 16 (4-(6-bromo-4,4-bis(2-ethylhexyl)-4H-silolo[3,2-b:4,5-b']dithiophen-2-yl)-5-fluoro-7-(5'-hexyl-[2,2'-bithiophen]-5-yl)benzo[c][1,2,5]thiadiazole)

Reaction Scheme 4

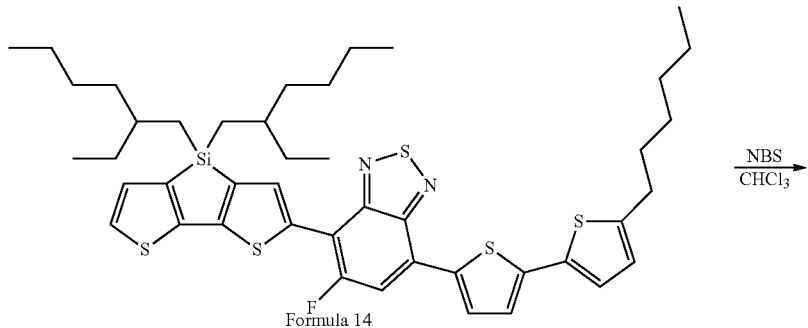

Formula 14

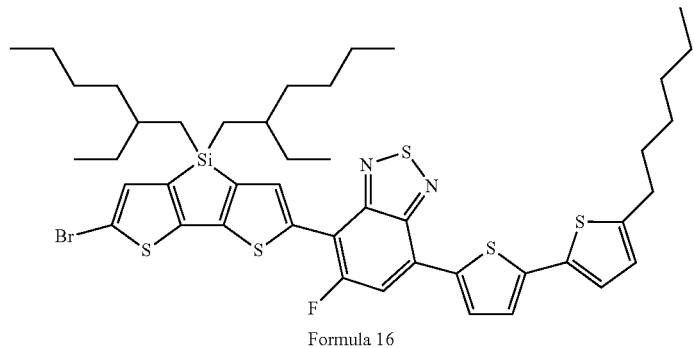

Formula 16

The compound represented by Formula 14 (0.81 g, 0.99 mmol) and chloroform (76 ml) were placed in a 250 ml reaction tube. The mixture was stirred in ice water at 0° C. in the dark. To the mixture was added portionwise N-bromosuccinimide (0.18 g, 1.04 mmol). The reaction was continued at room temperature for 16 h. The reaction mixture was transferred to a separatory funnel and extracted with water and dichloromethane. The solvent was removed from the dichloromethane layer using a rotary evaporator. The crude product was subjected to column chromatography using hexane and chloroform, affording 0.85 (yield 94%) g of the compound represented by Formula 16. The above reaction procedure is shown in Reaction Scheme 4.

$^1$H NMR (400 MHz, CDCl$_3$): δ=8.26 (t, 1H), 8.03 (d, 1H), 7.72 (d, 1H), 7.18 (d, 1H), 7.11 (d, 1H), 7.04 (s, 1H), 6.72 (d, 1H), 2.82 (t, 2H), 1.68 (m, 2H), 1.45-0.98 (m, 28H) 0.92-0.77 (m, 15H).

3-2) Synthesis of Compound Represented by Formula 17 (4-(4,4-bis(2-ethylhexyl)-6-(trimethylstannyl)-4H-silolo[3,2-b:4,5-b']dithiophen-2-yl)-5-fluoro-7-(5'-hexyl-[2,2'-bithiophen]-5-yl)benzo[c][1,2,5]thiadiazole)

Reaction Scheme 5

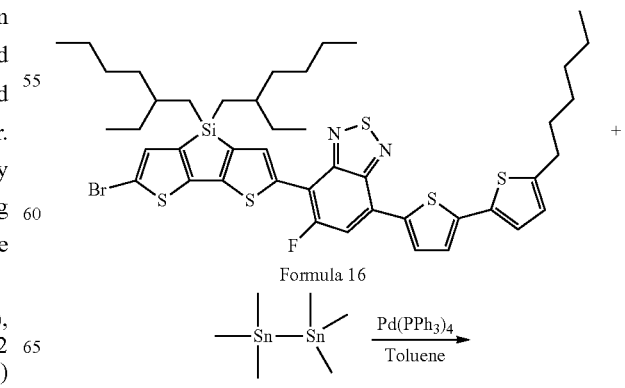

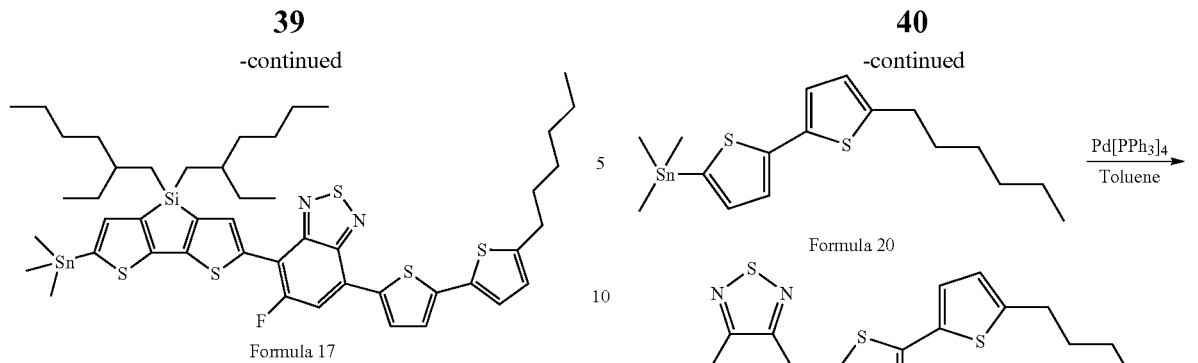

Formula 17

The compound represented by Formula 16 (0.81 g, 0.90 mmol) and hexamethylditin (1.48 g, 4.53 mmol) were placed in a 250 ml reaction tube and vacuuming and venting were repeated 3 times to create a nitrogen atmosphere in the reaction tube. Purified toluene (12.9 ml) and Pd(PPh₃)₄ (0.052 g, 0.04 mmol) were added and stirred under microwave irradiation. After stirring at 160° C. for 1 h, the reaction was stopped. The reaction mixture was transferred to a separatory funnel, extracted with diethyl ether, and washed sufficiently with distilled water. The solvent was removed from the diethyl ether layer using a rotary evaporator. The residue was washed with methanol at 40° C. until the hexamethylditin disappeared, and sufficiently dried, affording 0.83 g (yield 94%) of the compound represented by Formula 17. The above reaction procedure is shown in Reaction Scheme 5.

$^1$H NMR (400 MHz, CDCl$_3$): δ=8.29 (t, 1H), 8.02 (d, 1H), 7.72 (d, 1H), 7.18 (d, 1H), 7.13 (s, 1H), 7.11 (s, 1H), 6.72 (d, 1H), 2.82 (t, 2H), 1.70 (m, 2H), 1.60-1.17 (m, 24H), 1.03-0.77 (m, 19H), 0.46 (s, 9H).

3-3) Synthesis of Compound Represented by Formula 18 (4-bromo-5,6-difluoro-7-(5'-hexyl-[2,2'-bithiophen]-5-yl)benzo[c][1,2,5]thiadiazole)

Reaction Scheme 6

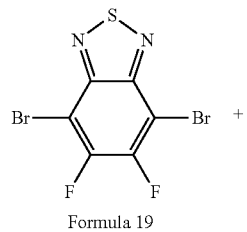

Formula 19

Formula 20

Formula 18

A 15 ml reaction tube was evacuated and flame dried at least 3 times to remove moisture therefrom. After the addition of the compound represented by Formula 19 (0.46 g, 1.26 mmol) and the compound represented by Formula 20 (0.26 g, 0.64 mmol), vacuuming and venting were repeated 3 times to create a nitrogen atmosphere in the reaction tube. Purified toluene (13 ml) and Pd(PPh₃)₄ (0.037 g, 0.03 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 194 mg (yield 61%) of the compound represented by Formula 18. The above reaction procedure is shown in Reaction Scheme 6.

$^1$H NMR (400 MHz, CDCl$_3$): δ=8.17 (d, 1H), 7.21 (d, 1H), 7.14 (d, 1H), 6.73 (d, 1H), 2.82 (t, 2H), 1.74-1.66 (m, 2H), 1.41-1.32 (m, 6H), 0.88 (t, 3H).

3-4) Synthesis of Compound Represented by Formula 6 (DTS-3F: 4-(4,4-bis(2-ethylhexyl)-6-(5-fluoro-7-(5'-hexyl-[2,2'-bithiophen]-5-yl)benzo[c][1,2,5]thiadiazol-4-yl)-4H-silolo[3,2-b:4,5-b']dithiophen-2-yl)-5,6-difluoro-7-(5'-hexyl-[2,2'-bithiophen]-5-yl)benzo[c][1,2,5]thiadiazole)

Reaction Scheme 7

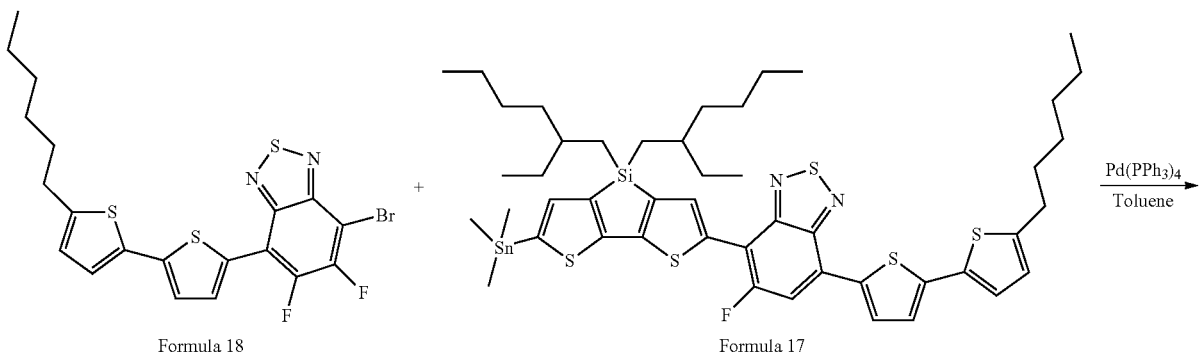

Formula 18          Formula 17

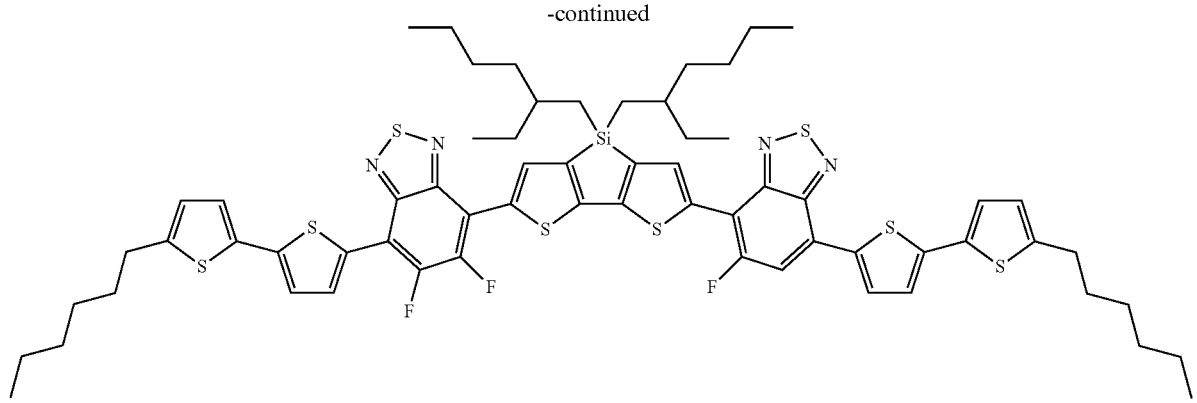

Formula 6

A 15 ml reaction tube was evacuated and flame dried at least 3 times to remove moisture therefrom. After the addition of the compound represented by Formula 18 (0.26 g, 0.56 mmol) and the compound represented by Formula 17 (0.53 g, 0.54 mmol), vacuuming and venting were repeated 3 times to create a nitrogen atmosphere in the reaction tube. Purified toluene (7.7 ml) and Pd(PPh$_3$)$_4$ (0.031 g, 0.02 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 0.461 g (yield 71%) of the compound represented by Formula 6 (DTS-3F). The above reaction procedure is shown in Reaction Scheme 7.

$^1$H NMR (400 MHz, 60° C., C$_2$D$_2$Cl$_4$): δ=8.37 (m, 2H), 8.23 (d, 1H), 8.06 (d, 1H), 7.74 (d, 1H), 7.26 (d, 1H), 7.22 (d, 1H), 7.18 (d, 1H), 7.15 (d, 1H), 6.78-6.77 (m, 2H), 2.88-2.84 (m, 4H), 1.79-1.71 (m, 4H), 1.62-1.03 (m, 34H), 0.97-0.87 (m, 18H).

Synthesis Example 4: Synthesis of Compound Represented by Formula 7 (7,7'-(4,4-bis(2-ethylhexyl)-4H-silolo[3,2-b:4,5-b']dithiophene-2,6-diyl)bis(5,6-difluoro-4-(5'-hexyl-[2,2'-bithiophen]-5-yl)benzo[c][1,2,5]thiadiazole))

Reaction Scheme 8

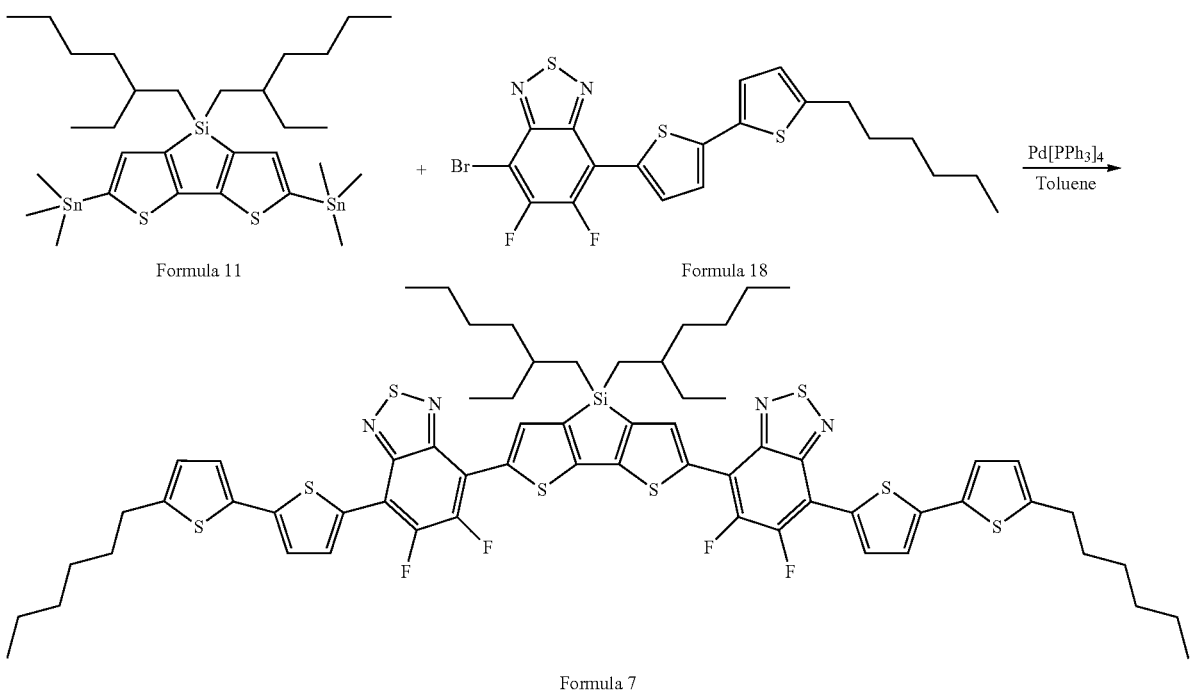

Formula 7

A 15 ml reaction tube was evacuated and flame dried at least 3 times to remove moisture therefrom. After the addition of the compound represented by Formula 11 (0.18 g, 0.37 mmol) and the compound represented by Formula 18 (0.13 g, 0.18 mmol), vacuuming and venting were repeated 3 times to create a nitrogen atmosphere in the reaction tube. Purified toluene (9 ml) and Pd(PPh$_3$)$_4$ (0.024 g, 0.03 mmol) were added and stirred under microwave irradiation. After stirring at 160° C. for 1 h, the reaction was stopped. The solvent was removed from the reaction mixture using a rotary evaporator. The residue was subjected to column chromatography using hexane and chloroform, affording 170 mg (yield 74%) of the compound represented by Formula 7.

$^1$H NMR (400 MHz, CDCl$_3$): δ=8.34 (t, 2H), 8.13 (d, 2H), 7.15 (d, 2H), 7.09 (d, 2H), 6.69 (d, 2H), 2.79 (t, 4H), 1.73-1.65 (m, 4H), 1.41-1.07 (m, 34H), 0.92-0.88 (m, 18H).

Synthesis Example 5: Synthesis of Compound Represented by Formula 9 as Second Organic Semiconductor Material

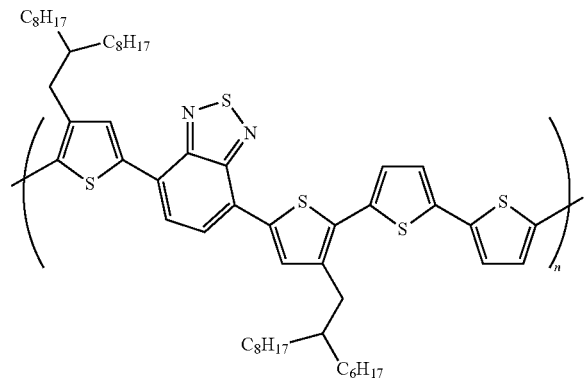

(9)

The compound represented by Formula 9 was used as a second organic semiconductor material. The second organic semiconductor material had a molecular weight of 10,000 to 100,000 g/mol but was not particularly limited thereto. In the following experiments, however, the molecular weight of the second organic semiconductor material was limited to 14,000 g/mol to clearly evaluate the influence of numerous variables.

Unless otherwise indicated in the following experimental examples, the compound of Formula 9 having a molecular weight of 14,000 g/mol was used as the second organic semiconductor material.

4,7-Bis(5-bromo-4-(2-octyldodecyl)thiophen-2-yl)benzo[c][1,2,5]thiadiazole (102 mg, 0.1 mmol), 5,5'-bis(trimethylstannyl)-2,2'-bithiophene (49.2 mg, 0.1 mmol), and tetrakis(triphenylphosphine)palladium(0) (Pd[PPh$_3$]$_4$(0) (2.3 mg, 0.002 mmol) were added all at once to a 20 ml microwave polymerization flask equipped with a magnetic bar under an argon atmosphere and 5 ml of toluene was added thereto. The mixture was sufficiently stirred under microwave irradiation at 18° C. for 40 min. After cooling to room temperature, the reaction mixture was reprecipitated in methanol (100 ml) and an aqueous hydrochloric acid solution (5 ml), followed by stirring at room temperature for 6 h. The resulting precipitate was collected by filtration, washed by Soxhlet extraction using methanol, hexane, and chloroform in this order, and extracted with chlorobenzene. The solvents were removed from the extract using a rotary evaporator. The extract was reprecipitated in methanol (150 ml) and dried under vacuum for 24 h or more, affording 117 mg (yield 94%) of the compound represented by Formula 9.

$^1$H NMR (400 MHz, C$_2$D$_2$Cl$_4$, 80° C.): δ=8.21 (br, 2H), 8.05 (br, 2H), 7.46-7.29 (br, 4H), 2.56 (br, 4H), 1.60 (br, 2H), 1.40-1.00 (br, 48H), 0.95-0.80 (br, 12H).

Synthesis Example 6: Synthesis of Compound Represented by Formula 19 as Second Organic Semiconductor Material (without BT Unit)

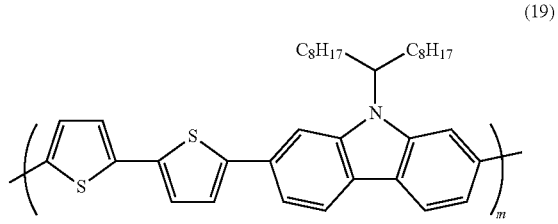

(19)

The compound represented by Formula 19 was used as a second organic semiconductor material. The second organic semiconductor material had a molecular weight of 10,000 to 100,000 g/mol but was not particularly limited thereto. In the following experiments, however, the molecular weight of the second organic semiconductor material was limited to 25,000 g/mol to clearly evaluate the influence of numerous variables.

Unless otherwise indicated in the following experimental examples, the compound of Formula 19 having a molecular weight of 25,000 g/mol was used as the second organic semiconductor material.

2,7-Bis(4',4',5',5'-tetramethyl-1',3',2'-dioxaborolan-2'-yl)-N-9''-heptadecanyl-carbazole (657.6 mg, 1.00 mmol), 5,5'-dibromo-2,2'-bithiophene (324.1 mg, 1.00 mmol), tris(dibenzylidineacetone)dipalladium(0) (Pd$_2$[dba]$_3$) (4.6 mg, 0.005 mmol), and tri(o-tolyl)phosphine (P(o-tol)$_3$) (6.1 mg, 0.002 mmol) were added all at once to a 50 ml flask equipped with a magnetic bar under an argon atmosphere and the mixture was dissolved in a mixture of 10.0 ml of oxygen-free toluene and 3.4 ml of an aqueous 20 wt % tetraethylammonium hydroxide solution. The solution was stirred at 95° C. for 72 h. Thereafter, the solution was added with bromobenzene (11 μl, 0.10 mmol), followed by stirring for 1 h. After the addition of phenylboronic acid (12 mg, 0.10 mmol), the resulting mixture was refluxed for 12 h until end-capping was completed. After the reaction was finished, the reaction mixture was reprecipitated in 150 ml of methanol and water (10:1), filtered through a 0.45 μm nylon filter, washed by Soxhlet extraction using acetone, hexane, and dichloromethane in this order, and extracted with chloroform. The solvents were removed from the extract using a rotary evaporator. The extract was reprecipitated in 150 ml of a mixture of methanol and water (10:1) and dried under vacuum for 24 h or more, affording 402 mg (yield 71%) of the compound represented by Formula 19.

$^1$H NMR (400 MHz, C$_2$D$_2$Cl$_4$, 80° C.): δ=8.15 (br, 2H), 7.81 (br, 2H), 7.59 (br, 2H), 7.45-7.30 (br, 4H) 4.71 (br, 1H), 2.42 (br, 4H), 2.12 (br, 4H), 1.40-1.15 (br, 20H), 0.90 (t, 6H).

Preparative Examples 1-4: Blending Solutions for the Formation of Photoactive Layers A mixture of appropriate amounts of a first organic semiconductor material, a second organic semiconductor material, and a fullerene compound was blended with a solvent. The blending solution was used to form a photoactive layer.

1) Preparation of First Organic Semiconductor Materials

The compounds represented by Formulae 3-7 synthesized in Synthesis Examples 1-4 were used as first organic semiconductor materials.

The first organic semiconductor materials are simply designated by Formulae 3, 4, 5, 6, and 7 to distinguish from each other in the following experiments.

2) Preparation of Second Organic Semiconductor Material

The compound represented by Formula 8 was purchased from Nanoclean Tech. (Lot No. YY7010) and used as a second organic semiconductor material.

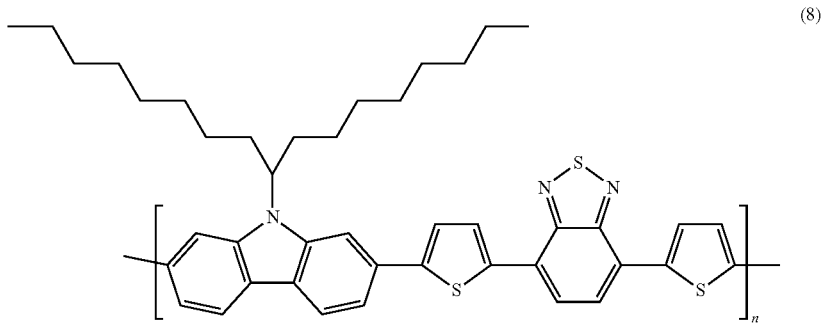

(8)

The second organic semiconductor material had a molecular weight of 50,000 to 100,000 g/mol but was not particularly limited thereto. In the following experiments, however, the molecular weight of the second organic semiconductor material was limited to 93000 g/mol to clarify the influence of numerous variables.

Unless otherwise indicated in the following experimental examples, the compound of Formula 8 having a molecular weight of 93000 g/mol was used as the second organic semiconductor material.

3) Preparation of Blending Solutions

The first organic semiconductor material, the second organic semiconductor material, and a fullerene compound were dissolved in 1 ml of a mixture of chlorobenzene and 1,8-diiodooctane in a ratio of 99.6:0.4 at 90° C. for at least 1 h to prepare a blending solution.

The kinds of the first organic semiconductor material, the second organic semiconductor material, the fullerene compound, and the solvent and mixing ratios thereof are shown in Table 1.

TABLE 1

|  | First organic semiconductor material | Second organic semiconductor material | Fullerene compound | Solvent |
|---|---|---|---|---|
| Preparative Example 1 | Formula 3 (DTS(BTTh$_2$)$_2$) 19.4 mg | Formula 8 0.4 mg | PC$_{71}$BM 13.2 mg | 1 ml |
| Preparative Example 2 | Formula 4 (DTS(FBTTh$_2$)(BTTh$_2$)) 19.4 mg | | | |
| Preparative Example 3 | Formula 5 (p-DTS(FBTTh$_2$)$_2$) 19.4 mg | | | |
| Preparative Example 4 | Formula 6 (DTS(DFBTTh$_2$)(FBTTh$_2$)) 19.4 mg | | | |
| Preparative Example 5 | Formula 7 DTS(DFBTTh$_2$)$_2$ 19.4 mg | | | |

Preparative Examples 6-8: Blending Solutions for the Formation of Photoactive Layers The compound represented by Formula 5 (p-DTS(FBTTh$_2$)$_2$), the compound represented by Formula 8 (PCDTBT), and PC$_{71}$BM as a fullerene compound were mixed in an appropriate ratio and blended with 1 ml of a mixture of chlorobenzene and 1,8-diiodooctane in a ratio of 99.6:0.4 to prepare a blending solution (p-DTS(FBTTh$_2$)$_2$:PCDTBT:PC$_{71}$BM).

The mixing ratios of the low molecular weight compound represented by Formula 5 (p-DTS(FBTTh$_2$)$_2$), the compound represented by Formula 8 (PCDTBT), the fullerene compound (PC$_{71}$BM), and the solvent are shown in Table 2.

TABLE 2

| | First organic semiconductor material | Second organic semiconductor material | Fullerene compound (PC$_{71}$BM) | Solvent |
|---|---|---|---|---|
| Preparative Example 6 | Formula 5 (p-DTS(FBTTh$_2$)$_2$) 19.6 mg | Formula 8 (PCDTBT) 0.2 mg | 13.2 mg | 1 ml |
| Preparative Example 7 | Formula 5 (p-DTS(FBTTh$_2$)$_2$) 19.4 mg | Formula 8 (PCDTBT) 0.4 mg | 13.2 mg | 1 ml |
| Preparative Example 8 | Formula 5 (p-DTS(FBTTh$_2$)$_2$) 18.81 mg | Formula 8 (PCDTBT) 0.99 mg | 13.2 mg | 1 ml |

Preparative Example 9: Blending Solution for the Formation of Photoactive Layer 19.4 mg of the compound represented by Formula 5 (p-DTS(FBTTh$_2$)$_2$), 0.4 mg of the second organic semiconductor material of Formula 9 synthesized in Synthesis Example 5, and 13.2 mg PC$_{71}$BM as a fullerene compound were mixed and blended with 1 ml of a mixture of chlorobenzene and 1,8-diiodooctane in a ratio of 99.6:0.4 to prepare a blending solution (p-DTS(FBTTh$_2$)$_2$:PCDTBT:PC$_{71}$BM).

Preparative Example 10: Blending Solution for the Formation of Photoactive Layer Using the Second Semiconductor Material of Formula 19 without BT Unit 19.4 mg of the compound represented by Formula 5 (p-DTS(FBTTh$_2$)$_2$), 0.4 mg of the second organic semiconductor material of Formula 19 synthesized in Synthesis Example 6, and 13.2 mg PC$_{71}$BM as a fullerene compound were mixed and blended with 1 ml of a mixture of chlorobenzene and 1,8-diiodooctane in a ratio of 99.6:0.4 to prepare a blending solution (p-DTS(FBTTh$_2$)$_2$:PCDTBT:PC$_{71}$BM).

Examples 1-5: Fabrication of Organic Solar Cells

Organic solar cells having the following structure were fabricated: ITO/PEIE/photoactive layer/MoO$_3$/Ag First, ITO was coated on a substrate. The ITO-coated substrate (hereinafter referred to as "ITO lower electrode") was sequentially washed with isopropyl alcohol for 10 min, acetone for 10 min, and isopropyl alcohol for 10 min, and dried before use.

PEIE was diluted with 2-methoxyethanol to prepare a solution of 0.2 wt % PEIE. The polymer solution was spin coated at 6000 rpm on the ITO lower electrode for 60 s and dried at 100° C. for 10 min to form a 5 nm thick PEIE surface modified layer.

Each of the blending solutions prepared in Preparative Examples 1-5 was spin coated to a thickness of 80 nm on the PEIE surface modified layer to form a photoactive layer. The spin coating was performed at 3000 rpm for 60 s.

Subsequently, MoO$_3$ was deposited to a thickness of 4 nm on the photoactive layer and an aluminum electrode was deposited to a thickness of 100 nm on the MoO$_3$ to form an upper electrode.

Examples 6-8: Fabrication of Organic Solar Cells

Organic solar cells were fabricated in the same manner as in Example 1, except that each of the blending solutions prepared in Preparative Examples 6-8 was used to form a photoactive layer instead of the blending solution prepared in Preparative Example 1.

Specifically, the photoactive layer of the organic solar cell of Example 6 was formed using the blending solution prepared in Preparative Example 6 instead of the blending solution prepared in Preparative Example 1. The photoactive layer of the organic solar cell of Example 7 was formed using the blending solution prepared in Preparative Example 7 instead of the blending solution prepared in Preparative Example 1. The photoactive layer of the organic solar cell of Example 8 was formed using the blending solution prepared in Preparative Example 8 instead of the blending solution prepared in Preparative Example 1.

Example 9: Fabrication of Organic Solar Cell

An organic solar cell was fabricated in the same manner as in Example 1. The characteristics of the organic solar cell were measured at 65° C. and 85% relative humidity (RH) in Experimental Example 7.

Example 10: Fabrication of Organic Solar Cell Using the Second Organic Semiconductor Material of Formula 9

An organic solar cell was fabricated in the same manner as in Example 1, except that the blending solution prepared in Preparative Example 9 was used to form a photoactive layer instead of the blending solution prepared in Preparative Example 1.

Comparative Examples 1-5: Fabrication of Organic Solar Cells (without PCDTBT)

Organic solar cells were fabricated in the same manner as in Examples 1-5, except that a photoactive layer was formed using a blending solution of 19.8 mg of each of the low molecular weight compounds (Formulae 3-7) and 13.2 mg of PC$_{71}$BM in 1 ml of a mixture of chlorobenzene and 1,8-diiodooctane (99.6:0.4) as a solvent without mixing with PCDTBT.

Specifically, the low molecular weight compounds represented by Formulae 3-7 were used in Comparative Examples 1-5, respectively.

Comparative Examples 6-20: Fabrication of Organic Solar Cells (with Controlled Factors Such as Kind of Solvent and Mixing Ratio)

Organic solar cells having the following structure were fabricated: ITO/PEIE/photoactive layer/MoO$_3$/Ag First, ITO was coated on a substrate. The ITO-coated substrate (hereinafter referred to as "ITO lower electrode") was sequentially washed with isopropyl alcohol for 10 min, acetone for 10 min, and isopropyl alcohol for 10 min, and dried before use.

PEIE was diluted with 2-methoxyethanol to prepare a solution of 0.2 wt % PEIE. The polymer solution was spin coated at 2500 rpm on the ITO lower electrode for 10 s and dried at 100° C. for 10 min to form a 5 nm thick PEIE surface modified layer.

Blending solutions were prepared to have the compositions shown in Table 3. Each of the blending solutions was spin coated to a thickness of 80 nm on the PEIE surface modified layer to form a photoactive layer. The spin coating was performed at 1000 rpm for 60 s.

Subsequently, $MoO_3$ was deposited to a thickness of 4 nm on the photoactive layer and an aluminum electrode was deposited to a thickness of 100 nm on the $MoO_3$ to form an upper electrode.

semiconductor materials were investigated by measuring and comparing the characteristics of the organic solar cells.

Figure 3:
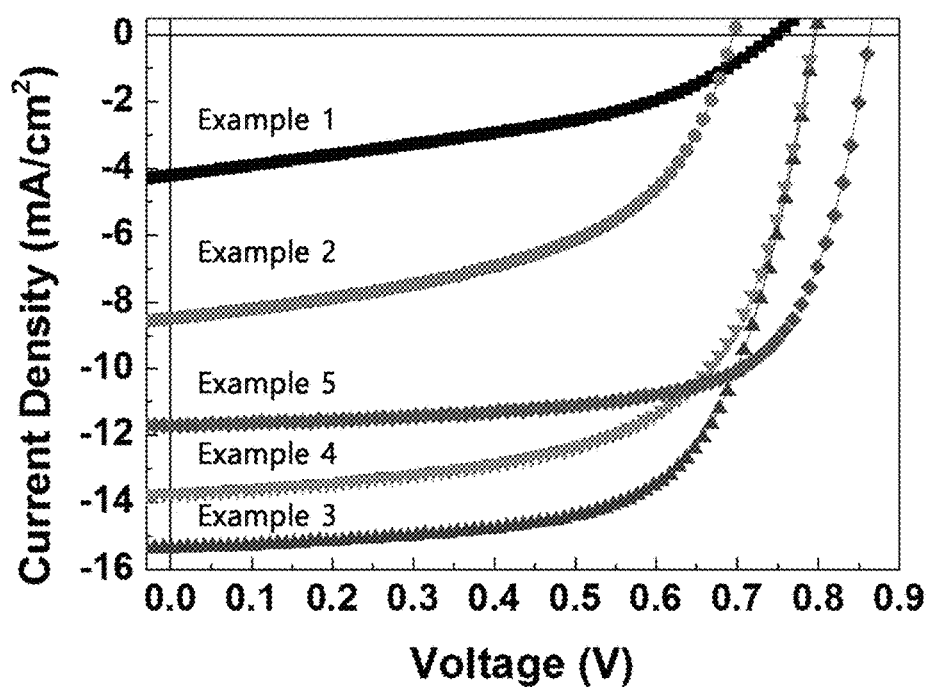
FIG. 3 shows the J-V characteristics of organic solar cells fabricated in Examples 1 to 5 when irradiated with light at an energy of 100 mW/cm$^2$.
Figure 5:
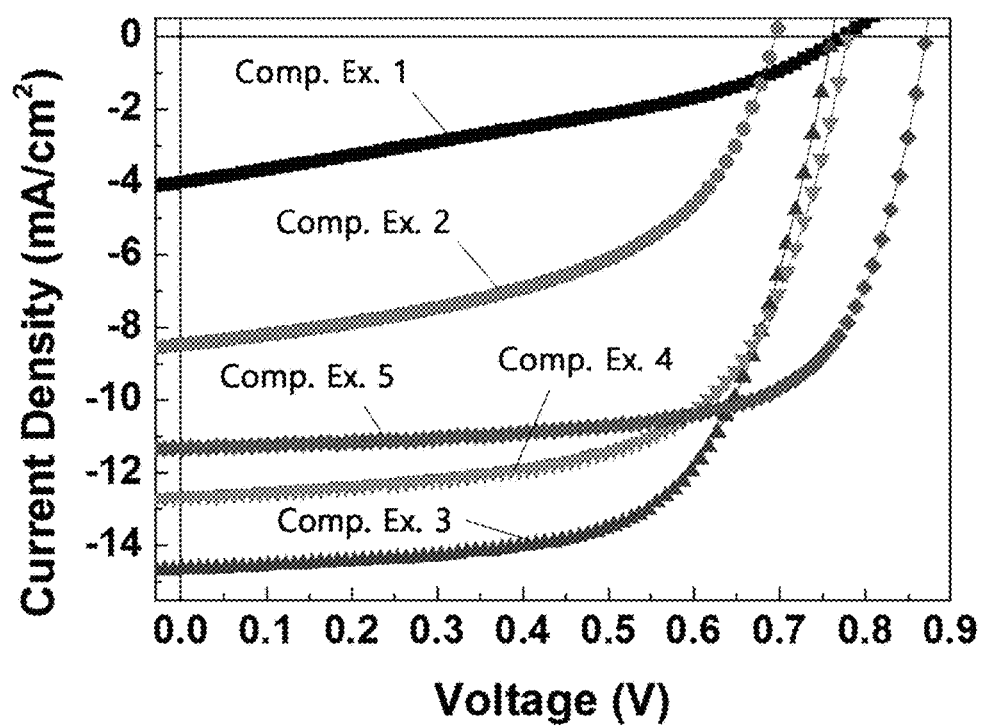
FIG. 5 shows the J-V characteristics of organic solar cells fabricated in Comparative Examples 1 to 5 when irradiated with light at an energy of 100 mW/cm$^2$.

Specifically, after the organic solar cells were irradiated with light at an energy of 100 mW/cm², their J-V characteristics were measured. FIGS. 3 and 5 show the J-V characteristics of the organic solar cells fabricated in Examples 1-5 and Comparative Example 1-5, respectively.

Figure 4:
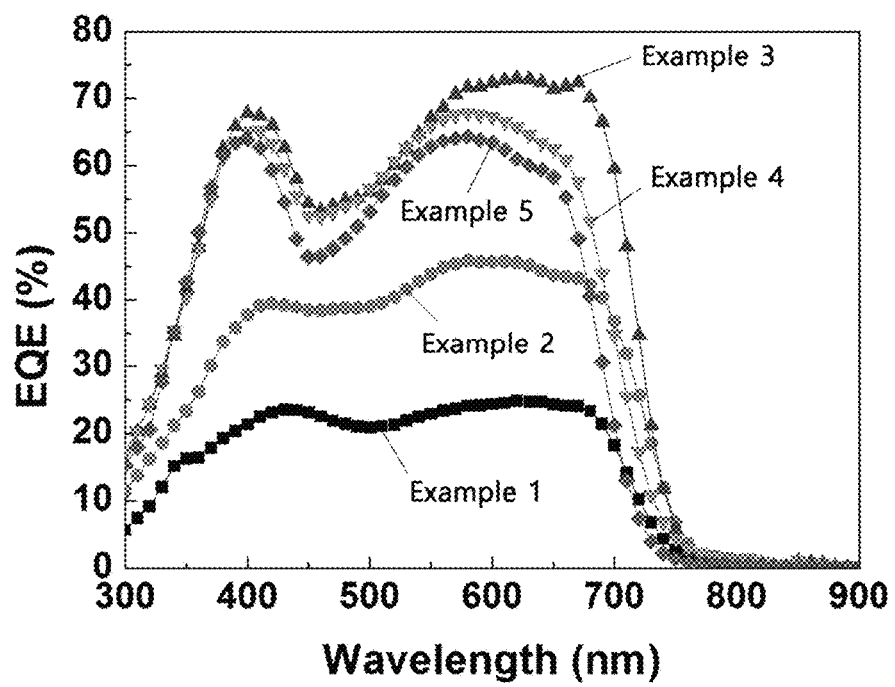
FIG. 4 shows the external quantum efficiencies (EQE, %) of organic solar cells fabricated in Examples 1 to 5.
Figure 6:
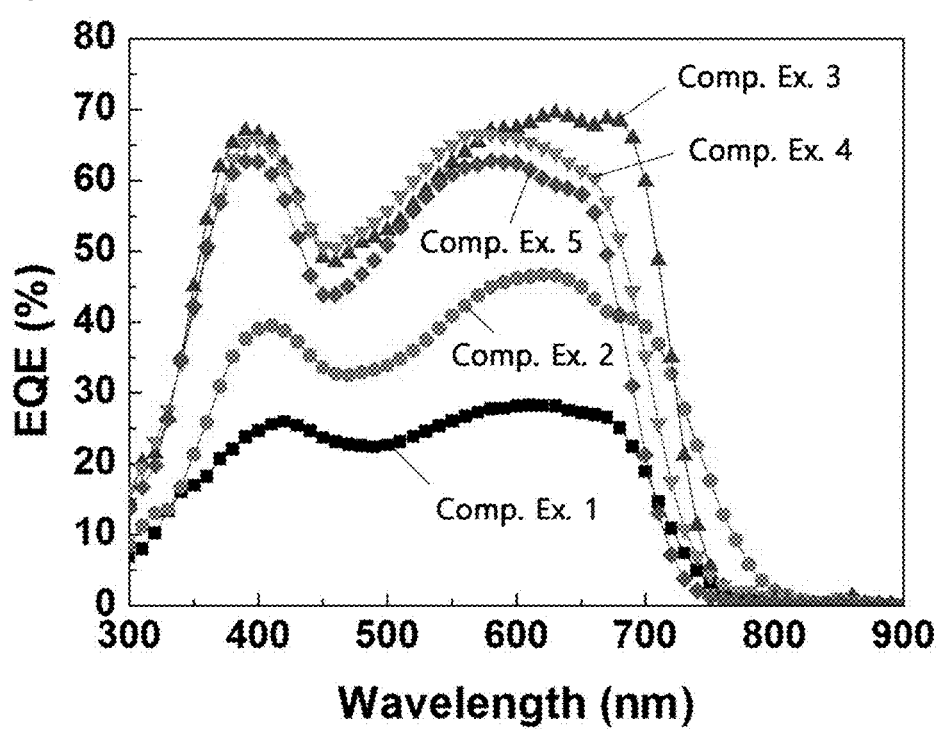
FIG. 6 shows the external quantum efficiencies (EQE, %) of organic solar cells fabricated in Comparative Examples 1 to 5.

FIGS. 4 and 6 show the external quantum efficiencies (EQE, %) of the organic solar cells fabricated in Examples 1-5 and Comparative Examples 1-5, respectively.

The measured parameters of the organic solar cells shown in FIGS. 3-6 are summarized in Table 4.

TABLE 3

|  | First organic semiconductor material (Formula 5, p-DTS(FBTTh$_2$)$_2$) | Second organic semiconductor material | Fullerene compound (PC$_{61}$BM) | Solvent |
|---|---|---|---|---|
| Comparative Example 6 | 20 mg | P3HT, 0 mg | 20 mg | Mixture of o-xylene and 1-methylnaphthalene (1:1), 1 ml |
| Comparative Example 7 | 15 mg | P3HT, 5 mg | | |
| Comparative Example 8 | 10 mg | P3HT, 10 mg | | |
| Comparative Example 9 | 5 mg | P3HT, 15 mg | | |
| Comparative Example 10 | 0 mg | P3HT, 20 mg | | |
| Comparative Example 11 | 20 mg | Formula 8 PCDTBT 0 mg | | |
| Comparative Example 12 | 15 mg | Formula 8 PCDTBT 5 mg | | |
| Comparative Example 13 | 10 mg | Formula 8 PCDTBT 10 mg | | |
| Comparative Example 14 | 5 mg | Formula 8 PCDTBT 15 mg | | |
| Comparative Example 15 | 0 mg | Formula 8 PCDTBT 20 mg | | |
| Comparative Example 16 | 20 mg | Formula 8 PCDTBT 0 mg | 20 mg | Mixture of chlorobenzene and 1,8-diiodooctane (99.6:0.4), 1 ml |
| Comparative Example 17 | 15 mg | Formula 8 PCDTBT 5 mg | | |
| Comparative Example 18 | 10 mg | Formula 8 PCDTBT 10 mg | | |
| Comparative Example 19 | 5 mg | Formula 8 PCDTBT 15 mg | | |
| Comparative Example 20 | 0 mg | Formula 8 PCDTBT 20 mg | | |

Comparative Example 21: Fabrication of Organic Solar Cell Using the Second Organic Semiconductor Material of Formula 19 without BT Unit An organic solar cell was fabricated in the same manner as in Example 1, except that the blending solution prepared in Preparative Example 10 was used to form a photoactive layer instead of the blending solution prepared in Preparative Example 1.

Experimental Example 1: Comparison of Performance of the Organic Solar Cells Depending on the Weights of the First and Second Organic Semiconductor Materials (1)

Changes in the performance of the organic solar cells fabricated in Examples 1-5 and Comparative Examples 1-5 depending on the kinds of the first and second organic

TABLE 4

|  | $V_{oc}$ (V) | $J_{sc}$ (mA/cm²) | $J_{sc, EQE}$ (mA/cm²) | FF (%) | PCE (%) |
|---|---|---|---|---|---|
| Example 1 | 0.75 | 4.21 | 5.01 | 40.68 | 1.28 |
| Example 2 | 0.70 | 80.28 | 9.83 | 54.53 | 3.17 |
| Example 3 | 0.80 | 15.37 | 14.37 | 66.36 | 8.13 |
| Example 4 | 0.79 | 13.73 | 12.84 | 62.75 | 6.84 |
| Example 5 | 0.86 | 11.71 | 11.51 | 69.82 | 7.06 |
| Comparative Example 1 | 0.78 | 4.00 | 5.56 | 34.32 | 1.06 |
| Comparative Example 2 | 0.70 | 8.47 | 9.30 | 52.20 | 3.07 |
| Comparative Example 3 | 0.79 | 14.63 | 13.69 | 59.64 | 6.68 |
| Comparative Example 4 | 0.78 | 12.83 | 12.67 | 64.10 | 6.37 |
| Comparative Example 5 | 0.87 | 11.33 | 11.25 | 68.75 | 6.78 |

Referring to FIG. 3-6 and Table 4, the organic solar cells of Examples 1-5 showed, on average, open circuit voltages ($V_{OC}$) of 0.7-0.86 V, $J_{SC}$ values of 4.21-15.37 mA/cm², fill factors of 5.01-66.36, and photoelectric conversion efficiencies (PCE) of 1.28-8.13%. The most optimized organic solar cell of Example 3 showed a $J_{SC}$ of 15.37 mA/cm², an open circuit voltage ($V_{OC}$) of 0.80 V, a fill factor of 66.36, and a PCE of 8.13%.

In contrast, the organic solar cell of Comparative Examples 1-5, whose photoactive layer was formed without PCDTBT (Formula 8), showed, on average, an open circuit voltage ($V_{OC}$) of 0.70-0.87 V, a $J_{SC}$ of 4.0-14.63 mA/cm², a fill factor of 34.32-68.75, and a PCE of 1.06-6.68%.

The organic solar cell of Comparative Example 3 as a counterpart of the organic solar cell of Example 3 was found to have an open circuit voltage ($V_{OC}$) of 0.79 V, a $J_{SC}$ of 14.63 mA/cm², a fill factor of 59.64, and a PCE of 6.68%.

That is, when the organic solar cells of Examples 1-5 were compared with those of Comparative Examples 1-5, the presence of the high molecular weight compound (PCDTBT) of Formula 8 was found to increase the PCE (%) by a minimum of 0.1% to 1.0%. The most optimized organic solar cell was already designed such that the efficiency reached as high as 7%. The formation of the photoactive layer using the mixture of the first organic semiconductor material, the second organic semiconductor material, and the fullerene compound was found to achieve a 1% increase in efficiency, which is regarded as significant in the art.

Experimental Example 2: Comparison of Characteristics of the Organic Solar Cells (2)

Changes in the performance of the organic solar cells of Examples 6-8 and Comparative Example 3 depending on the mixing ratio of the first and second organic semiconductor materials were investigated by measuring and comparing the characteristics of the organic solar cells.

TABLE 5

|  | $V_{oc}$ (V) | $J_{sc}$ (mA/cm²) | FF (%) | $PCE_{max}$ (%) |
|---|---|---|---|---|
| Comparative Example 3 | 0.79 | 14.63 | 59.64 | 6.68 |
| Example 6 | 0.81 | 14.23 | 61.41 | 7.10 |
| Example 7 | 0.80 | 15.37 | 66.36 | 8.13 |
| Example 8 | 0.70 | 10.08 | 46.38 | 3.29 |

Figure 7:
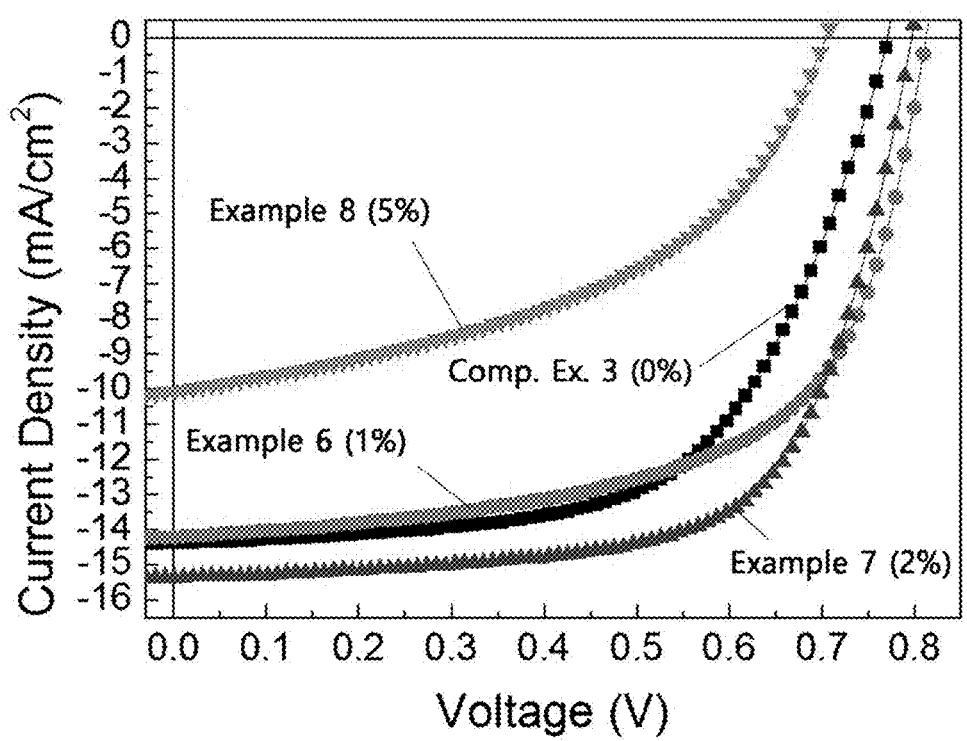
FIG. 7 shows the J-V characteristics of organic solar cells fabricated in Examples 6 to 8 and Comparative Example 3 when irradiated with light at an energy of 100 mW/cm$^2$.

Referring to Table 5 and FIG. 7, the organic solar cell of Example 7, whose photoactive layer was formed using the mixture of the first and second organic semiconductor materials in a weight ratio of 1:0.02, showed a $J_{SC}$ of 15.37 mA/cm², an open circuit voltage ($V_{OC}$) of 0.80 V, a fill factor of 66.36, and a PCE of 8.13%.

In contrast, the organic solar cell of Comparative Example 3, whose photoactive layer was formed without the high molecular weight compound of Formula 8 (PCDTBT), showed a $J_{SC}$ of 14.63 mA/cm², an open circuit voltage ($V_{OC}$) of 0.79 V, a fill factor of 59.64, and a PCE of 6.68%.

The organic solar cell of Example 8, whose photoactive layer was formed using the mixture of the first organic semiconductor material and the second organic semiconductor material of Formula 8 (PCDTBT) in a weight ratio of 1:≥0.05, in which the high molecular weight compound of Formula 8 as the second organic semiconductor material was present in a relatively large amount, showed a $J_{SC}$ of 10.08 mA/cm², an open circuit voltage ($V_{OC}$) of 0.70 V, a fill factor of 46.38, and a PCE of 3.29%.

Taken together, the JSC, FF, and PCE values of the inventive organic solar cells increased with gradually increasing mixing weight ratio of the first organic semiconductor material to the second organic semiconductor material in the photoactive layers from 1:0.01 to 1:0.02. However, for the organic solar cell of Example 8, the efficiency was considerably lowered to ~3% in the higher mixing ratio (1:≥0.05).

These results demonstrate that the highest efficiencies can be achieved when the first organic semiconductor material and the second organic semiconductor material are mixed in a weight ratio of 1:0.01-0.04, and particularly, efficiencies of ≥7%, with a maximum of 8.13%, can be achieved when the low molecular weight compound represented by Formula 5 (p-DTS(FBTTh₂)₂) is used as the first organic semiconductor material.

In contrast, the efficiency of the organic solar cell of Example 8 whose photoactive layer was formed using the mixture of the first organic semiconductor material and the second organic semiconductor material in a weight ratio of 1:≥0.05 was significantly lowered by at least about 2.5 times. These results lead to the conclusion that it is preferred to mix the first organic semiconductor material with the second organic semiconductor material in a weight ratio of 1:0.01-0.04.

Experimental Example 3: Comparison of Characteristics of the Organic Solar Cell (3)—Morphology Images of the photoactive layers of the organic solar cells of Example 3 and Comparative Example 3 were taken by transmission electron microscopy (TEM) and energy-filtering transmission electron microscopy (EFTEM) to compare the morphologies of the photoactive layers depending on the presence or absence of the second organic semiconductor material.

Figure 8A:
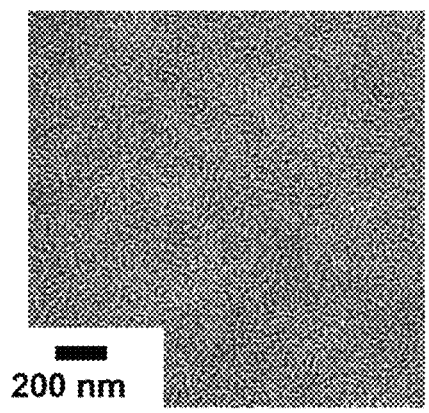
FIGS. 8A and 8B show transmission electron microscopy (TEM) images of photoactive layers formed in Example 3 (a) and Comparative Example 3 (b), respectively.
Figure 8B:
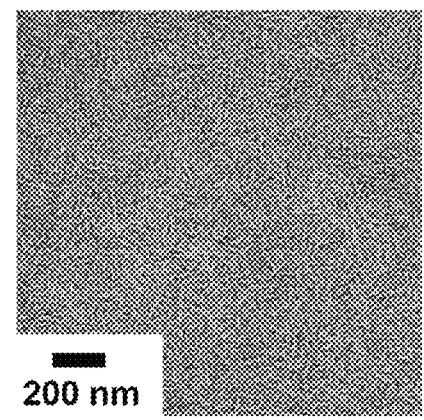
Figure 9A:
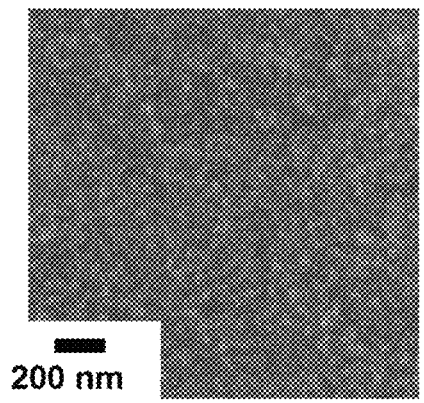
FIGS. 9A and 9B show energy-filtering transmission electron microscopy (EF-TEM) images of photoactive layers formed in Example 3 (a) and Comparative Example 3 (b), respectively.
Figure 9B:
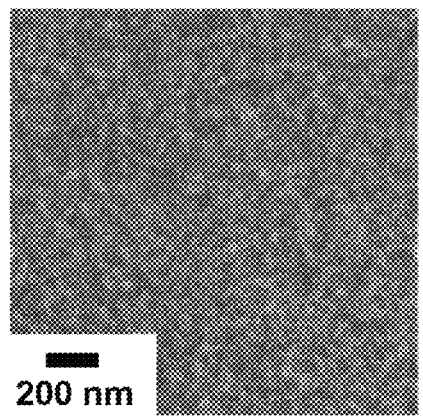
Figure 10A:
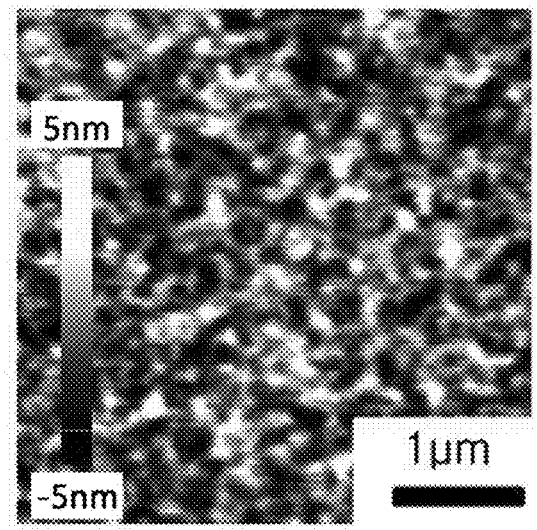
FIGS. 10A to 10D show atomic force microscopy (AFM) images of the surface morphology of a photoactive layer formed in Example 3 ($R_q$=0.75 nm)
Figure 10B:
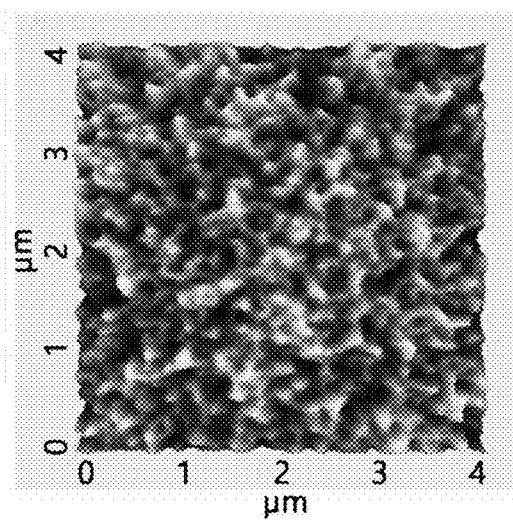
Figure 10C:
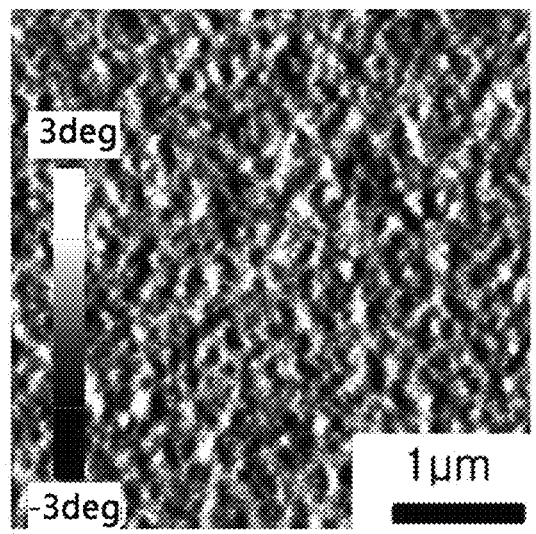
Figure 10D:
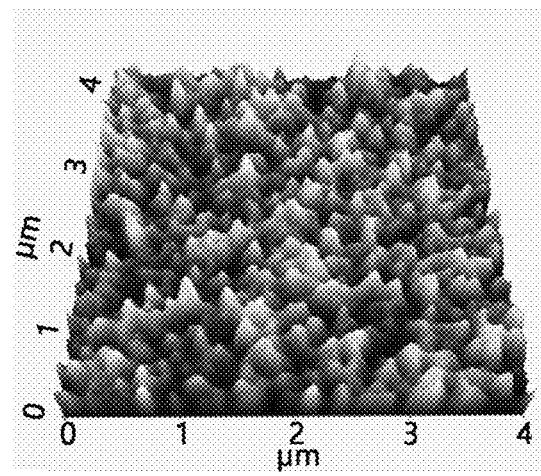
Figure 11A:
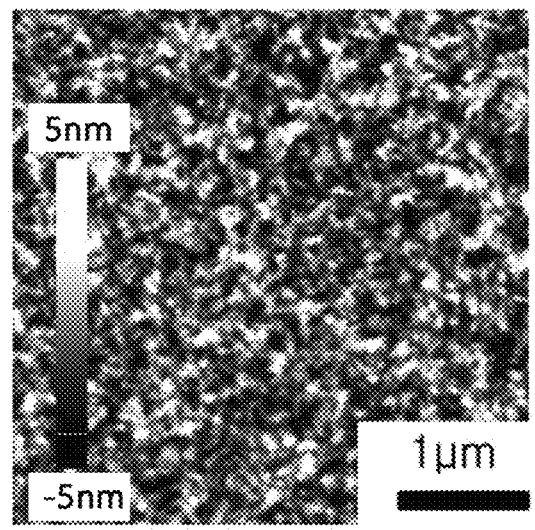
FIGS. 11A to 11D show atomic force microscopy (AFM) images of the surface morphology of a photoactive layer formed in Comparative Example 3 ($R_q$=1.36 nm)
Figure 11B:
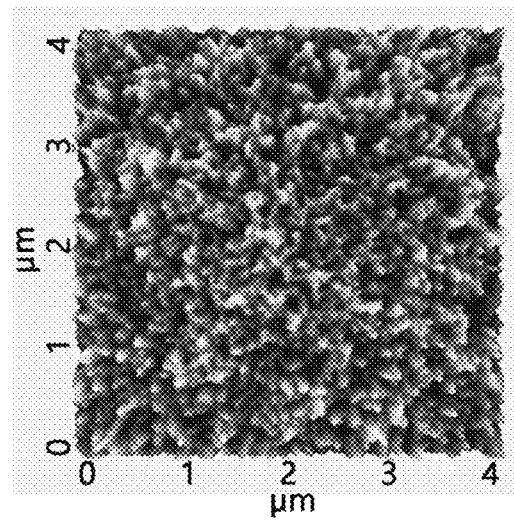
Figure 11C:
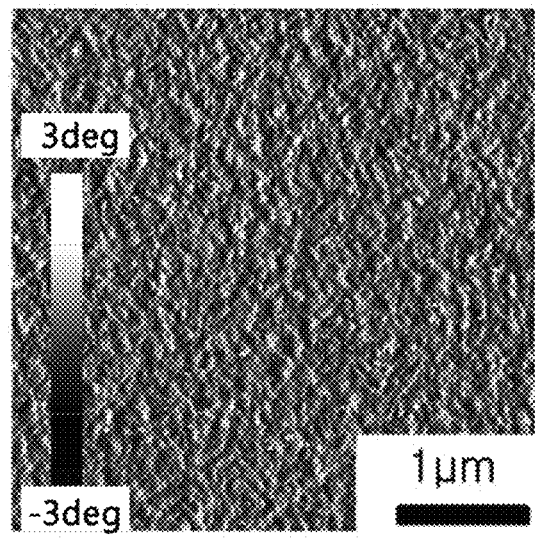
Figure 11D:
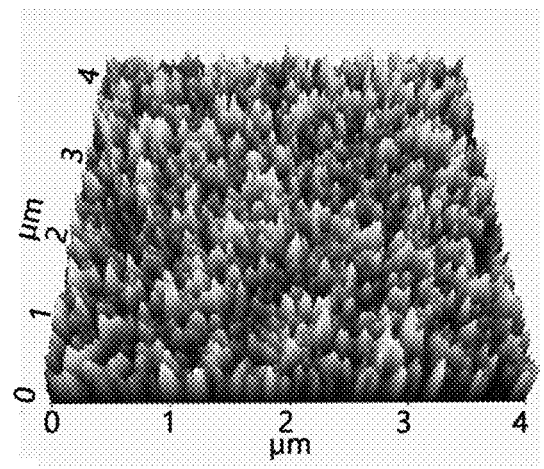

FIG. 8 shows transmission electron microscopy (TEM) images of the photoactive layers formed in Example 3 (a) and Comparative Example 3 (b) and FIG. 9 shows energy-filtering transmission electron microscopy (EF-TEM) images of the photoactive layers formed in Example 3 (a) and Comparative Example 3 (b).

Referring to FIG. 8, the photoactive layer formed in Example 3 was more uniform than that formed in Comparative Example 3.

In FIG. 8, Si and C atoms are colored green and red, respectively. The Si atoms are estimated to be derived from the low molecular weight compound p(-DTS(FBTTh₂)₂) as the first organic semiconductor material. The C atoms are those included in the first organic semiconductor material, the second organic semiconductor material, and the fullerene compound constituting the photoactive layer and are not considered to represent one of the constituent materials. In light of the above, the presence of the high molecular weight compound as the second organic semiconductor material in the photoactive layer formed in Example 3 caused the low molecular weight compound to deaggregate, and as a result, the green portions were more uniformly distributed in the photoactive layer formed in Example 3 than in the photoactive layer formed in Comparative Example 3.

Experimental Example 4: Comparison of Characteristics of the Organic Solar Cells (4)—Morphology Images of the photoactive layers of the organic solar cells of Example 3 and Comparative Example 3 were taken by atomic force microscopy (AFM) to compare the morphologies of the photoactive layers depending on the presence or absence of the second organic semiconductor material.

FIG. 10 shows AFM images showing the surface morphologies of the photoactive layer formed in Example 3 ($R_q$=0.75 nm) and FIG. 11 shows AFM images of the photoactive layer formed in Comparative Example 3 ($R_q$=1.36 nm).

Referring to FIGS. 10 and 11, the surface morphology of the photoactive layer of the photoactive layer formed in Example 3 was sharper than that that of the photoactive layer of the photoactive layer formed in Comparative Example 3. The improved morphology of the photoactive layer formed in Example 3 is thought to be because the presence of the high molecular weight compound (PCDTBT) of Formula 8 as the second organic semiconductor material in the photoactive layer formed in Example 3 caused the first organic semiconductor material (p-DTS(FBTTh$_2$)$_2$) to deaggregate or suppressed and prevented aggregation of the first organic semiconductor material.

Experimental Example 5: Comparison of Characteristics of the Organic Solar Cells (5)

Changes in the performance of the organic solar cells of Comparative Examples 6-20 depending on the kind of the solvent were investigate by measuring and comparing the characteristics of the organic solar cells.

Figure 12:
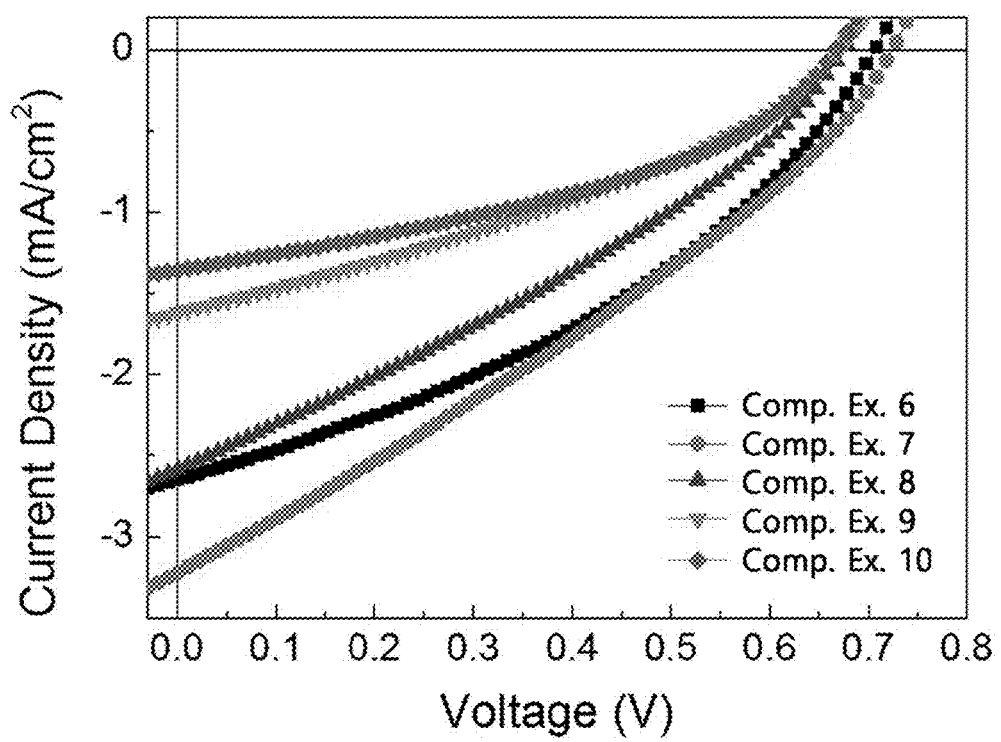
FIG. 12 shows the J-V characteristics of organic solar cells fabricated in Comparative Examples 6 to 10 when irradiated with light at an energy of 100 mW/cm$^2$.
Figure 13:
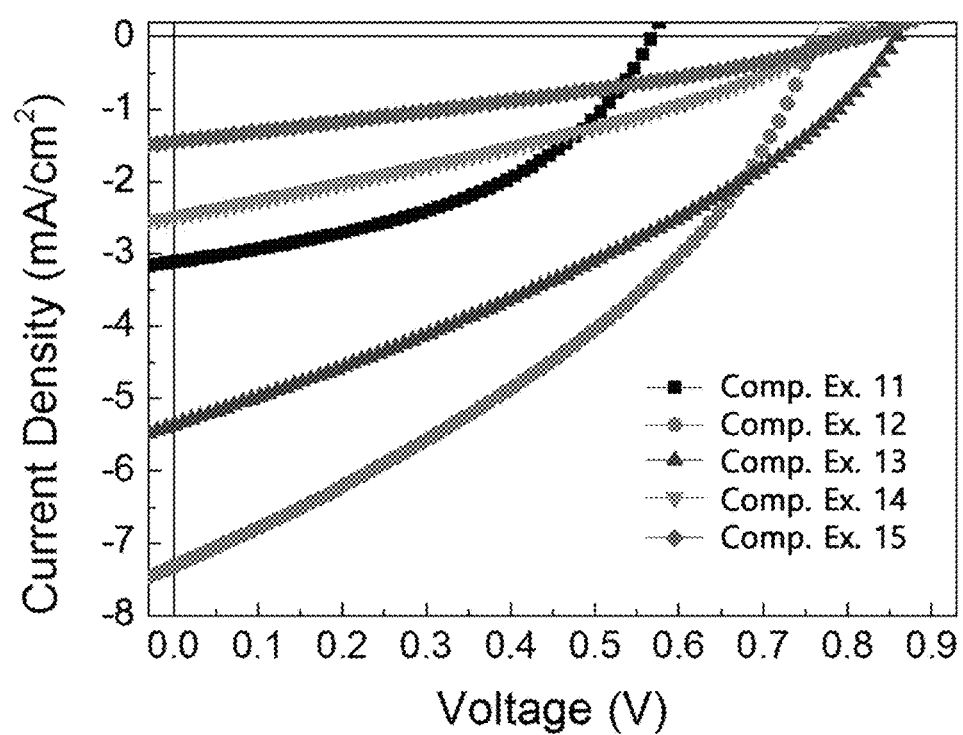
FIG. 13 shows the J-V characteristics of organic solar cells fabricated in Comparative Examples 11 to 15 when irradiated with light at an energy of 100 mW/cm$^2$.
Figure 14:
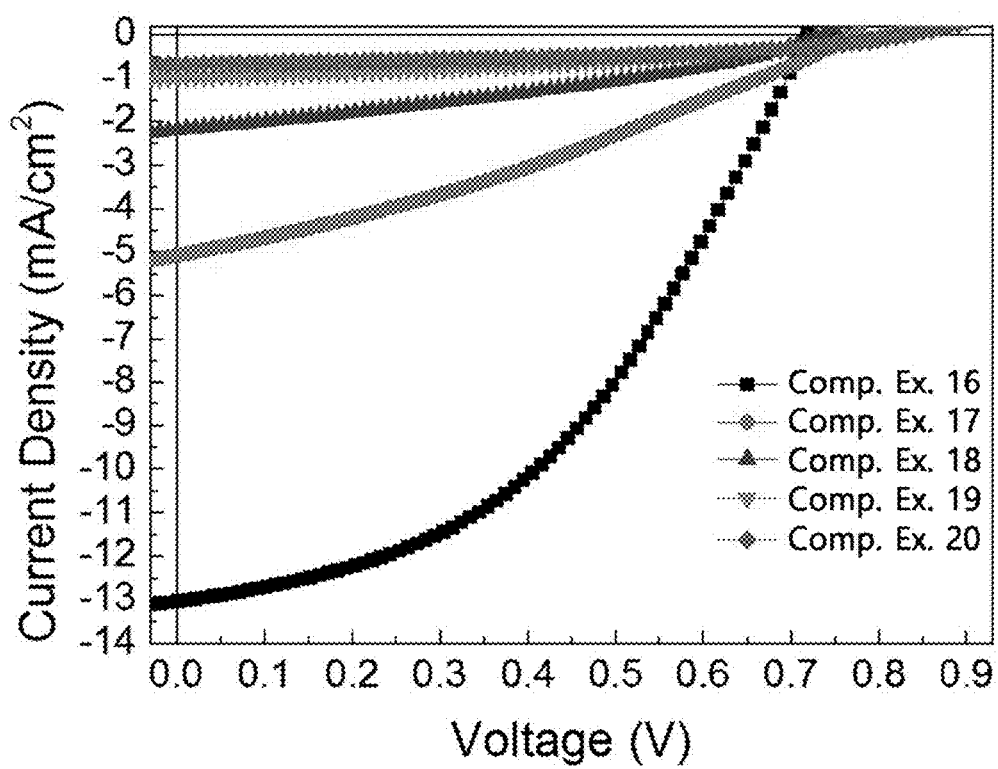
FIG. 14 shows the J-V characteristics of organic solar cells fabricated in Comparative Examples 16 to 20 when irradiated with light at an energy of 100 mW/cm$^2$.

FIGS. 12, 13, and 14 show the J-V characteristics of the organic solar cells fabricated in Comparative Examples 6-10, Comparative Examples 11-15, and Comparative Examples 16-20 when irradiated with light at an energy of 100 mW/cm$^2$, respectively.

TABLE 6

| | $V_{oc}$ (V) | $J_{sc}$ (mA/cm$^2$) | FF (%) | PCE$_{max}$ (%) |
|---|---|---|---|---|
| Comparative Example 6 | 0.71 | 2.65 | 37.01 | 0.69 |
| Comparative Example 7 | 0.72 | 3.22 | 30.38 | 0.71 |
| Comparative Example 8 | 0.67 | 2.59 | 31.33 | 0.55 |
| Comparative Example 9 | 0.67 | 1.62 | 34.06 | 0.37 |
| Comparative Example 10 | 0.67 | 1.36 | 39.97 | 0.36 |
| Comparative Example 11 | 0.57 | 3.11 | 44.13 | 0.78 |
| Comparative Example 12 | 0.76 | 7.32 | 36.36 | 1.62 |
| Comparative Example 13 | 0.86 | 5.37 | 33.59 | 1.55 |
| Comparative Example 14 | 0.88 | 2.50 | 32.05 | 0.71 |
| Comparative Example 15 | 0.91 | 1.46 | 30.88 | 0.41 |
| Comparative Example 16 | 0.72 | 13.04 | 44.37 | 4.14 |
| Comparative Example 17 | 0.76 | 5.07 | 31.53 | 1.22 |
| Comparative Example 18 | 0.73 | 2.19 | 33.29 | 0.53 |
| Comparative Example 19 | 0.80 | 0.98 | 37.87 | 0.30 |
| Comparative Example 20 | 0.83 | 0.67 | 44.15 | 0.25 |

Referring to FIGS. 12-14 and Table 6, the organic solar cells fabricated in Comparative Examples 6-10 were different from the inventive organic solar cells, typified by the organic solar cell of Example 3, in the mixing weight ratio of the second organic semiconductor material and the first organic semiconductor material constituting the photoactive layers.

In the organic solar cells fabricated in Comparative Examples 6-10, the first organic semiconductor material was mixed with the second organic semiconductor material in a weight ratio of 1:0.3-3.

Due to this difference, the organic solar cells fabricated in Comparative Examples 6-10 showed $J_{SC}$ values of 1.62-3.22 mA/cm$^2$, open circuit voltages ($V_{OC}$) of 0.67-0.72 V, fill factors of 30.38-37.01, and PCE values of 1% or less, which were significantly low compared to those of the organic solar cell of Example 3. Specifically, the $J_{SC}$, FF, and PCE values of the organic solar cells fabricated in Comparative Examples 6-10 were at least 5 times, 2 times, and 11 times lower than those of the organic solar cell of Example 3, respectively.

The organic solar cells fabricated in Comparative Examples 11-15 were different from the organic solar cell fabricated in Example 3 in the mixing weight ratio (1:0.3-3) of the first and second organic semiconductor materials constituting the photoactive layers and the kind of the solvent.

Due to these differences, the organic solar cells fabricated in Comparative Examples 11-15 showed $J_{SC}$ values of 1.46-7.32 mA/cm$^2$, open circuit voltages ($V_{OC}$) of 0.57-0.91 V, fill factors of 30-44, and PCE values of 0.78-2%.

The performance of the organic solar cells fabricated in Comparative Examples 11-15 was slightly improved compared to that of the organic solar cells fabricated in Comparative Examples 6-10 but was still significantly lower than that of the inventive organic solar cell. Particularly, the PCE values of the organic solar cells fabricated in Comparative Examples 11-15 were a minimum of at least 4 times and a maximum of at least 11 times lower than those of the inventive organic solar cell.

The organic solar cells fabricated in Comparative Examples 10-20 were different from the organic solar cell fabricated in Example 3 in the mixing weight ratio of the first and second organic semiconductor materials. The organic solar cell of Comparative Example 16, whose photoactive layer was formed without the second organic semiconductor material, was measured to have the highest PCE (~4%).

From these results, it can be concluded that the inventive organic solar cell achieves a high efficiency of ~8% when the first organic semiconductor material is mixed with the second organic semiconductor material in a weight ratio of 1:0.01-0.04 and a slight increase in the weight proportion of the high molecular weight compound as the second organic semiconductor material leads to a considerable deterioration in performance.

Furthermore, the performance of the inventive organic solar cells was influenced by the kind of the solvent as well as the mixing weight ratio of the first and second organic semiconductor materials.

Specifically, the performance of the organic solar cells of Comparative Examples 16-20, where the solvent was the same as that used in the organic solar cell of Example 3, was slightly increased to ~4% but the performance of the organic solar cell of Comparative Examples 6-15, where the solvent was different from that used in the organic solar cell of Example 3, achieved considerably low efficiencies of only <2%.

Experimental Example 6: Analysis of Thermal Stability

Changes in the performance of the organic solar cell of Example 3 at a high temperature of 110° C. were investigated by measuring and comparing the characteristics of the organic solar cells of Example 3 and Comparative Example 3.

Specifically, 20 min, 40 min, 60 min, 80 min, 100 min, and 120 min after each of the organic solar cells of Example 3 and Comparative Example 3 was heated in an oven at 110° C., the photoelectric conversion efficiency (PCE), fill factor (FF), and $J_{SC}$ values of the organic solar cell were measured. The measured photoelectric conversion efficiency (PCE), fill factor (FF), and $J_{SC}$ values are shown in FIGS. 15, 16, and 17, respectively.

Figure 15:
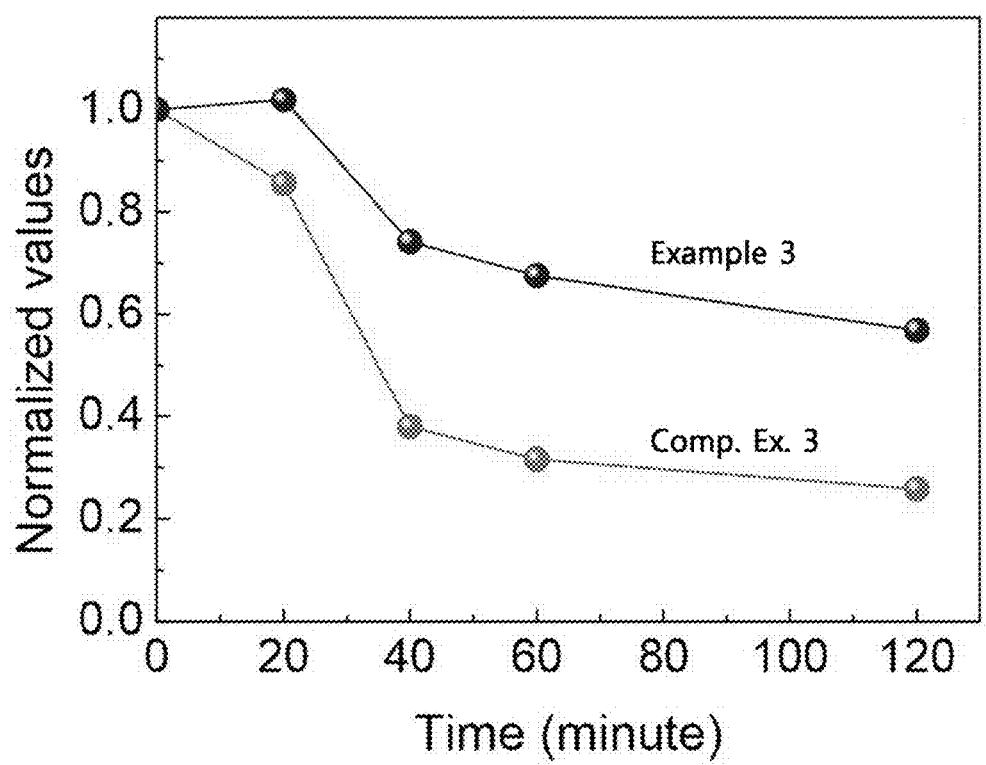
FIG. 15 shows changes in the photoelectric conversion efficiency (PCE) of organic solar cells fabricated in Example 3 and Comparative Example 3, which were measured under high temperature conditions (110° C.) at given time points.

FIG. 15 shows changes in the photoelectric conversion efficiency (PCE) of the organic solar cells fabricated in Example 3 and Comparative Example 3, which were measured at 110° C. at the given time points. FIG. 16 shows changes in the fill factor (FF) of the organic solar cells fabricated in Example 3 and Comparative Example 3, which were measured at 110° C. at the given time points. FIG. 17 shows changes in the $J_{SC}$ of the organic solar cells fabricated in Example 3 and Comparative Example 3, which were measured at 110° C. at the given time points.

Figure 16:
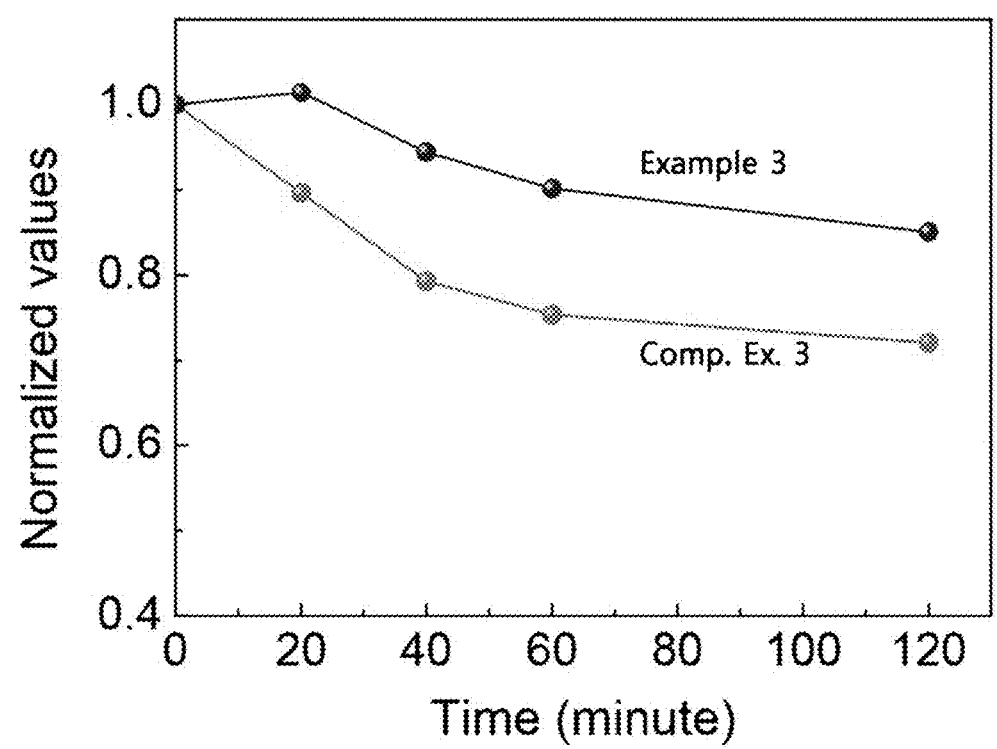
FIG. 16 shows changes in the fill factor (FF) of organic solar cells fabricated in Example 3 and Comparative Example 3, which were measured under high temperature conditions (110° C.) at given time points.
Figure 17:
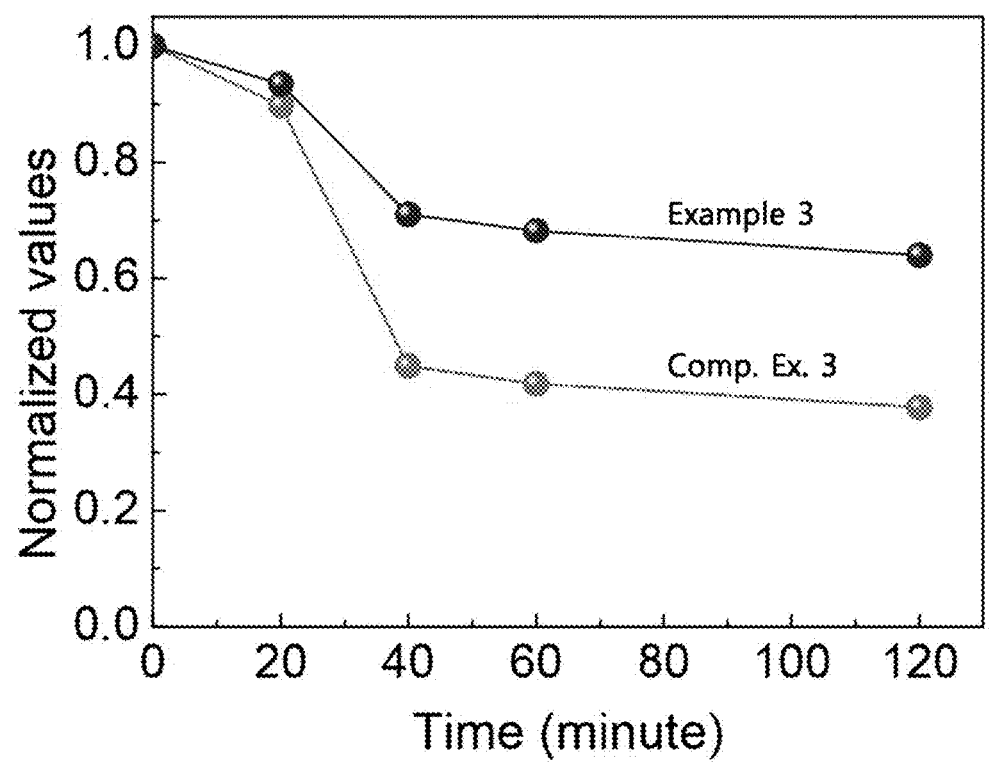
FIG. 17 shows changes in the short-circuit current density ($J_{SC}$) of organic solar cells fabricated in Example 3 and Comparative Example 3, which were measured under high temperature conditions (110° C.) at given time points.

As shown in FIGS. 15, 16, and 17, the organic solar cell of Example 3 maintained its initial PCE, fill factor (FF), and $J_{SC}$ values for up to 20 min, and thereafter, began to gradually lose its performance. The maximum PCE, fill factor (FF), and $J_{SC}$ values of the organic solar cell of Example 3 were reduced by 40%, 10%, and 20-30% for 40-120 min, respectively.

Unlike the inventive organic solar cell, the organic solar cell of Comparative Example 3, whose photoactive layer was formed using the same solvent as that used in the inventive organic solar cell without the second organic semiconductor material, began to rapidly lose its performance from the beginning of exposure to high temperature. Specifically, the PCE, fill factor (FF), and $J_{SC}$ values of the organic solar cell of Comparative Example 3 were reduced by 10%, 10-20%, and 10% for the initial 20 min, respectively. Thereafter, the PCE, fill factor (FF), and $J_{SC}$ values of the organic solar cell of Comparative Example 3 fell to half their initial values for 40-120 min.

The performance of the organic solar cell of Example 3 after exposure to 110° C. for 120 min was compared with that of the organic solar cell of Comparative Example 3. As a result, the PCE of the organic solar cell of Comparative Example 3 was reduced to 0.2, which is 3 times lower than that of the organic solar cell of Example 3. The fill factor (FF) of the organic solar cell of Comparative Example 3 was reduced to 0.6, which is 1.3 times lower than that of the organic solar cell of Example 3. The $J_{SC}$ of the organic solar cell of Comparative Example 3 was reduced to 0.4, which is at least 2 times lower than that of the organic solar cell of Example 3.

These results concluded that despite the use of the same solvent, the life characteristics of the comparative organic solar cell of Comparative Example 3, whose photoactive layer was formed without the second organic semiconductor material, were deteriorated considerably when exposed to high temperature. Specifically, the PCE, FF, and $J_{SC}$ values of the inventive organic solar cell were maintained at 60-80% of their initial values when exposed to a high temperature of 100-200° C. for 40-150 min.

In contrast, the PCE, FF, and $J_{SC}$ values of the organic solar cell fabricated without using the second organic semiconductor material were reduced to 60% or less (a maximum of 20%) of their initial values when exposed to the same temperature for 1 h. These values are 1.3 times (a maximum of 3 times) lower than those of the inventive organic solar cell.

Experimental Example 7: Analysis of Long-Term Stability

Time-dependent changes in the performance of the organic solar cell fabricated in Example 9 were measured in order to investigate whether the performance of the organic solar cell was maintained stable for a long time.

Specifically, changes in the photoelectric conversion efficiency (PCE), fill factor (FF), $J_{SC}$, and $V_{OC}$ of the organic solar cell of Example 9 were measured at 65° C. and 85% relative humidity (RH) for 0-1000 h.

Figure 18:
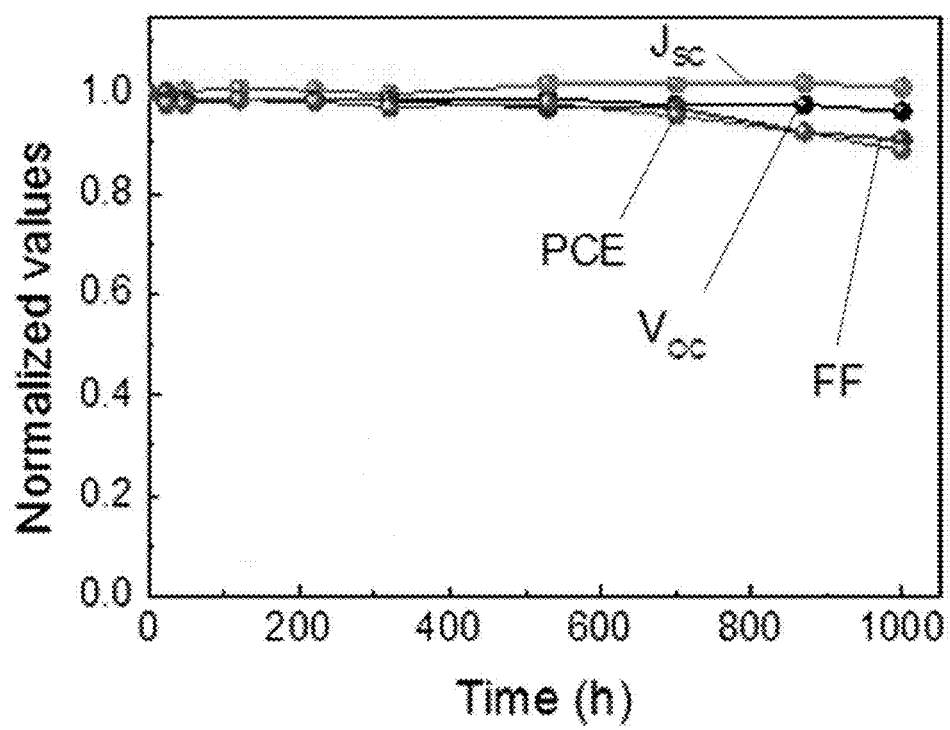
FIG. 18 shows the photoelectric conversion efficiency (PCE), fill factor (FF), $J_{SC}$, and $V_{OC}$ values of an organic solar cell fabricated in Example 9, which were measured at 65° C. and 85% relative humidity (RH) at given time points.

FIG. 18 shows the photoelectric conversion efficiency (PCE), fill factor (FF), $J_{SC}$, and $V_{OC}$ values of the organic solar cell of Example 9, which were measured at 65° C. and 85% relative humidity (RH) at given time points.

As shown in FIG. 18, the organic solar cell of Example 9 maintained its initial PCE, fill factor (FF), and $J_{SC}$ values for up to 700 h, and thereafter, began to gradually lose its performance.

However, FIG. 18 shows that the PCE and FF values of the organic solar cell of Example 9 were reduced by at most 10% even after 800 h and the initial $J_{SC}$ and $V_{OC}$ values of the organic solar cell were substantially maintained for up to 1000 h. These results demonstrate high stability of the inventive organic solar cell in the ordinary environment at 85% RH for a maximum of 1000-1500 h.

Experiment Example 8: Analysis of Performance of the Organic Solar Cells Depending on the Presence or Absence of BT Unit in the Second Organic Semiconductor Materials The structure of the BT unit is represented as follows:

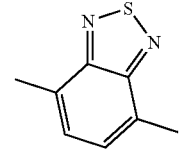

Significant changes in the performance of the organic solar cells were observed depending on the presence or absence of the BT unit in the second organic semiconductor materials although the second organic semiconductor materials are represented by the same formula. This was verified by measuring and comparing the characteristics of the organic solar cells of Example 10 and Comparative Examples 3 and 21.

Specifically, the organic solar cells fabricated in Example 10 and Comparative Examples 3 and 21 were measured for J-V characteristics when irradiated with light at an energy of 100 mW/cm². The results are shown in FIG. 19.

The organic solar cells fabricated in Example 10 and Comparative Examples 3 and 21 were measured for external quantum efficiency (EQE, %). The results are shown in FIG. 20.

Figure 19:
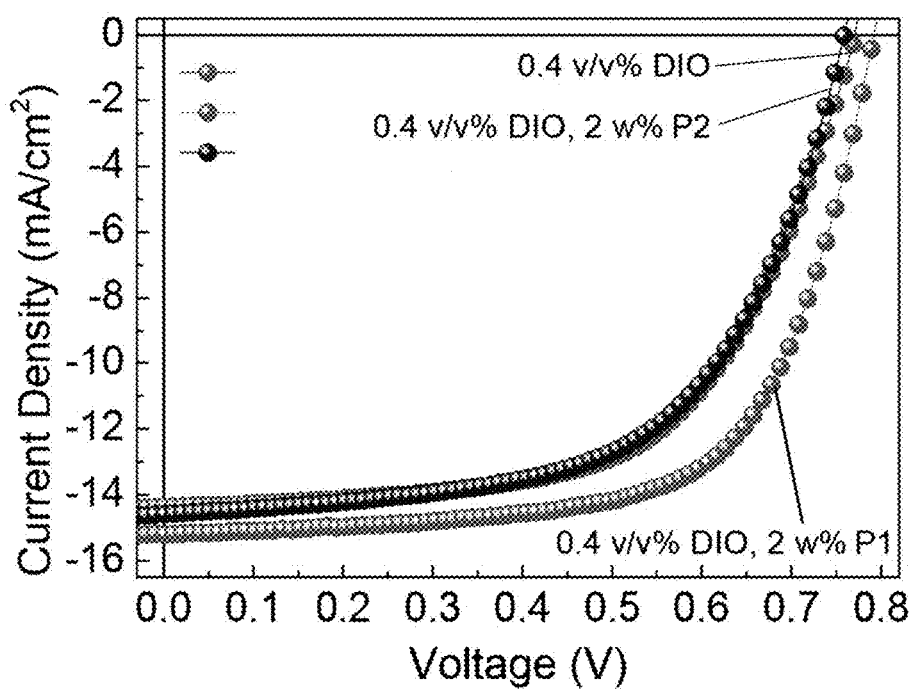
FIG. 19 shows the J-V characteristics of organic solar cells fabricated in Example 10 and Comparative Examples 3 and 21 when irradiated with light at an energy of 100 mW/cm$^2$.
Figure 20:
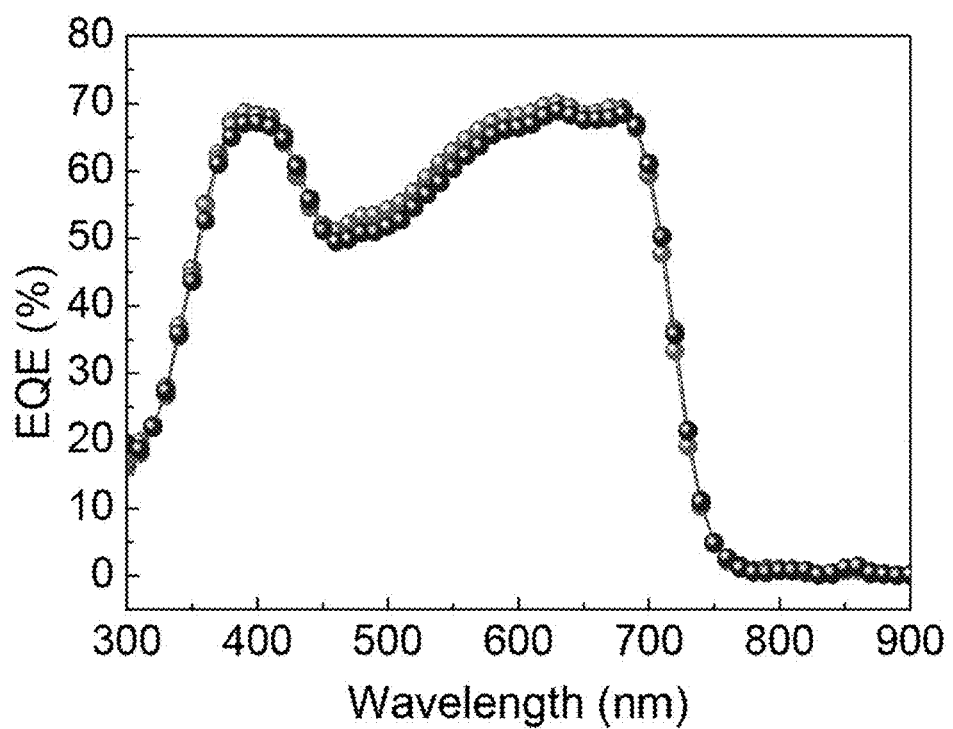
FIG. 20 shows the external quantum efficiencies (EQE, %) of organic solar cells fabricated in Example 10 and Comparative Examples 3 and 21.

The measured parameters of the organic solar cells of Example 10 and Comparative Examples 3 and 21 shown in FIGS. 19 and 20 are summarized in Table 7.

TABLE 7

| | $V_{oc}$ (V) | $J_{sc}$ (mA/cm²) | FF (%) | $PCE_{max}$ (%) |
|---|---|---|---|---|
| Example 10 | 0.79 | 15.18 | 66.04 | 7.92 |
| Comparative Example 21 | 0.76 | 14.57 | 59.10 | 6.54 |
| Comparative Example 3 | 0.77 | 14.46 | 60.0 | 6.68 |

As shown in FIGS. 19 and 20 and Table 7, the organic solar cell of Comparative Example 21 showed the same performance as the organic solar cell of Comparative Example 3 fabricated without using any second organic semiconductor material. Specifically, the organic solar cell of Comparative Example 21 showed a $J_{SC}$ of 14.57 mA/cm$^2$, an open circuit voltage ($V_{OC}$) of 0.76 V, a fill factor of 59.10, and a PCE of 6.54%.

In contrast, the organic solar cell of Example 10 showed a $J_{SC}$ of 15.18 mA/cm$^2$, an open circuit voltage ($V_{OC}$) of 0.79 V, a fill factor of 66.04, and a PCE of 7.92%, which are comparable to those of the organic solar cells using the polymer compound of Formula 8 as a second organic semiconductor material.

These results conclude that the organic solar cell using the second organic semiconductor material of Formula 9 including the BT unit can achieve a high efficiency of at least 7% with a maximum of 7.92%, which is significantly higher by ≥1% than the PCEs of the organic solar cell of Comparative Example 3 fabricated without using any second organic semiconductor material and the organic solar cell of Comparative Example 21 fabricated using the second organic semiconductor material without the BT unit.

What is claimed is:

1. An organic solar cell comprising: a lower electrode formed on a substrate; a photoactive layer formed on the lower electrode and comprising (a) a p-type organic semiconductor material, (b) an n-type organic semiconductor material, and (c) a solvent; and an upper electrode formed on the photoactive layer wherein the p-type organic semiconductor material (a) comprises (a-1) a first organic semiconductor material represented by Formula 1:

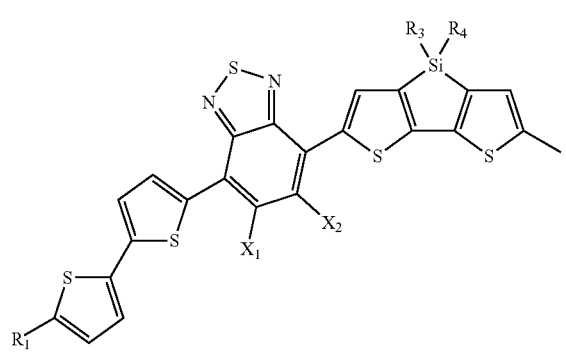

(1)

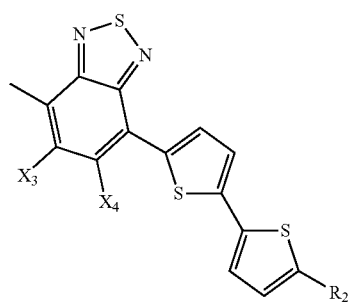

wherein $X_1$, $X_2$, $X_3$, and $X_4$ are the same or different and are each independently hydrogen or a halogen and $R_1$, $R_2$, $R_3$, and $R_4$ are the same or different and are each independently a $C_1$-$C_{22}$ linear or branched alkyl group, and (a-2) a second organic semiconductor material represented by Formula 2:

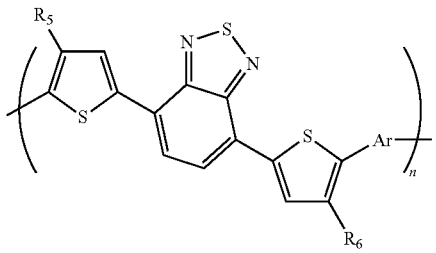

(2)

wherein $R_5$ and $R_6$ are the same or different and are each independently H or a $C_1$-$C_{22}$ linear or branched alkyl group, n is an integer from 1 to 10,000,000, and Ar is selected from aromatic groups having the following structures 2a:

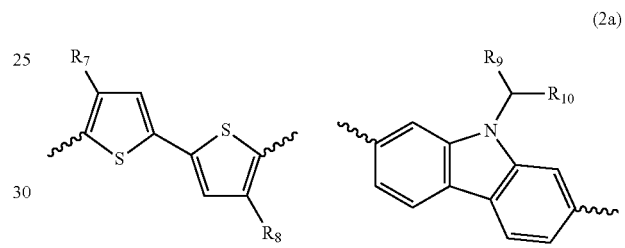

(2a)

wherein $R_7$, $R_8$, $R_9$, and $R_{10}$ are the same or different and are each independently H or a $C_1$-$C_{22}$ linear or branched alkyl group.

2. The organic solar cell according to claim 1, wherein $R_1$ and $R_2$ in Formula 1 are the same or different and are each independently a $C_1$-$C_7$ linear alkyl group, $R_3$ and $R_4$ in Formula 1 are the same or different and are each independently a $C_8$-$C_{22}$ branched alkyl group, and $R_5$ and $R_6$ in Formula 2 are the same or different and are each independently H or a $C_8$-$C_{22}$ branched alkyl group.

3. The organic solar cell according to claim 2, wherein when $R_1$ and $R_2$ in Formula 1 are symmetric and have the same structure, $R_3$ and $R_4$ in Formula 1 are symmetric and have the same structure and $R_5$ and $R_6$ in Formula 2 are symmetric and have the same structure.

4. The organic solar cell according to claim 1, wherein $X_1$, $X_2$, $X_3$, and $X_4$ in Formula 1 are the same or different and are each independently hydrogen or F.

5. The organic solar cell according to claim 1, wherein the first organic semiconductor material (a-1) is a low molecular weight compound having a molecular weight of 1000 to 2000 g/mol and the second organic semiconductor material (a-2) is a high molecular weight compound having a molecular weight of 50,000 to 100,000 g/mol.

6. The organic solar cell according to claim 1, wherein the first organic semiconductor material (a-1) is selected from the low molecular weight compounds represented by Formulae 3 to 7:

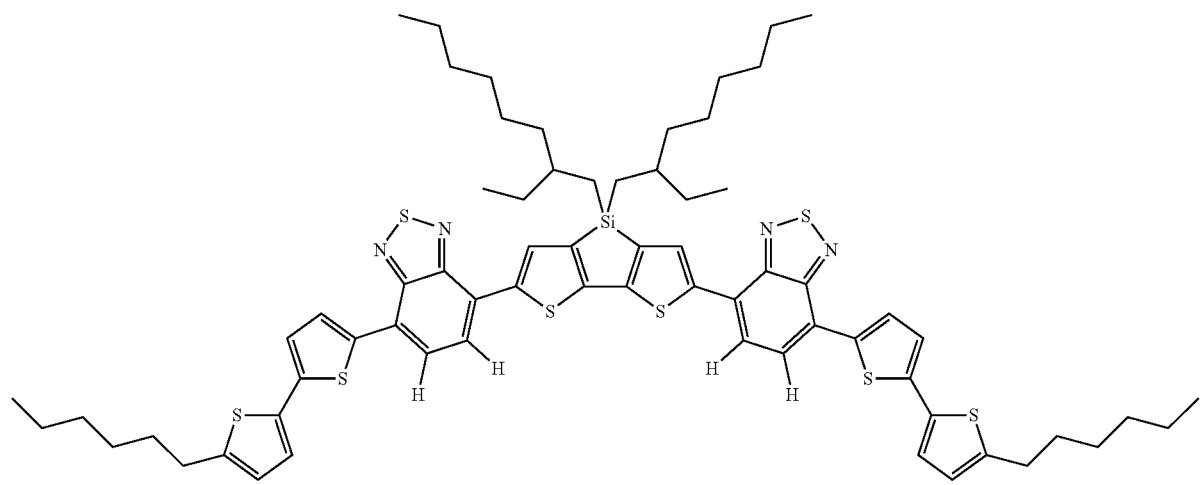
(3)
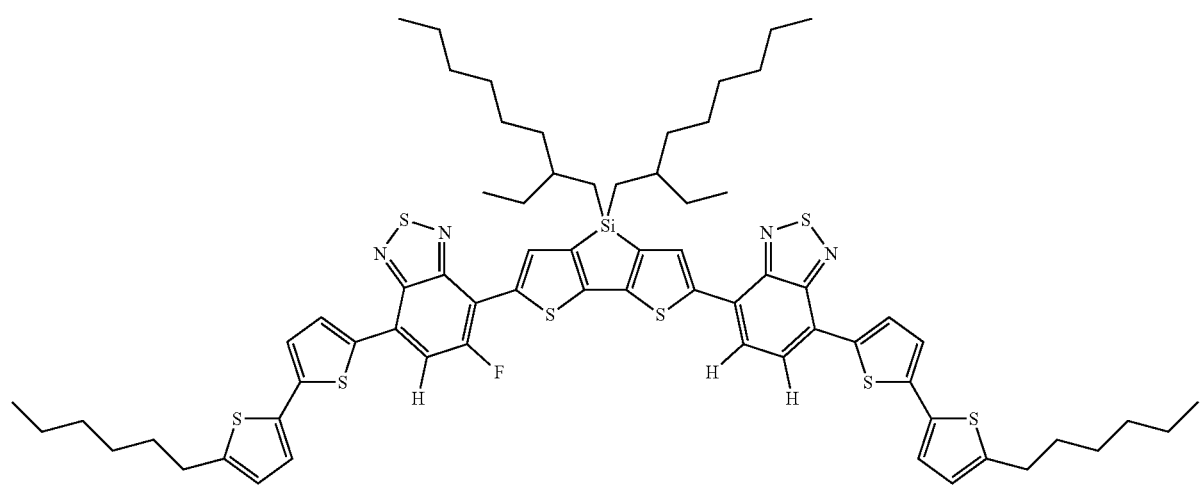
(4)
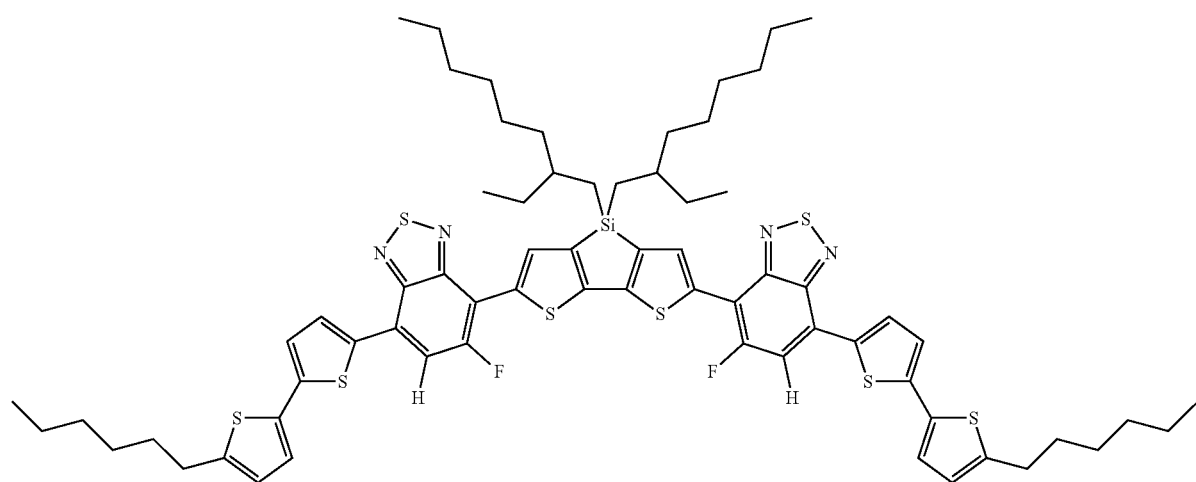
(5)

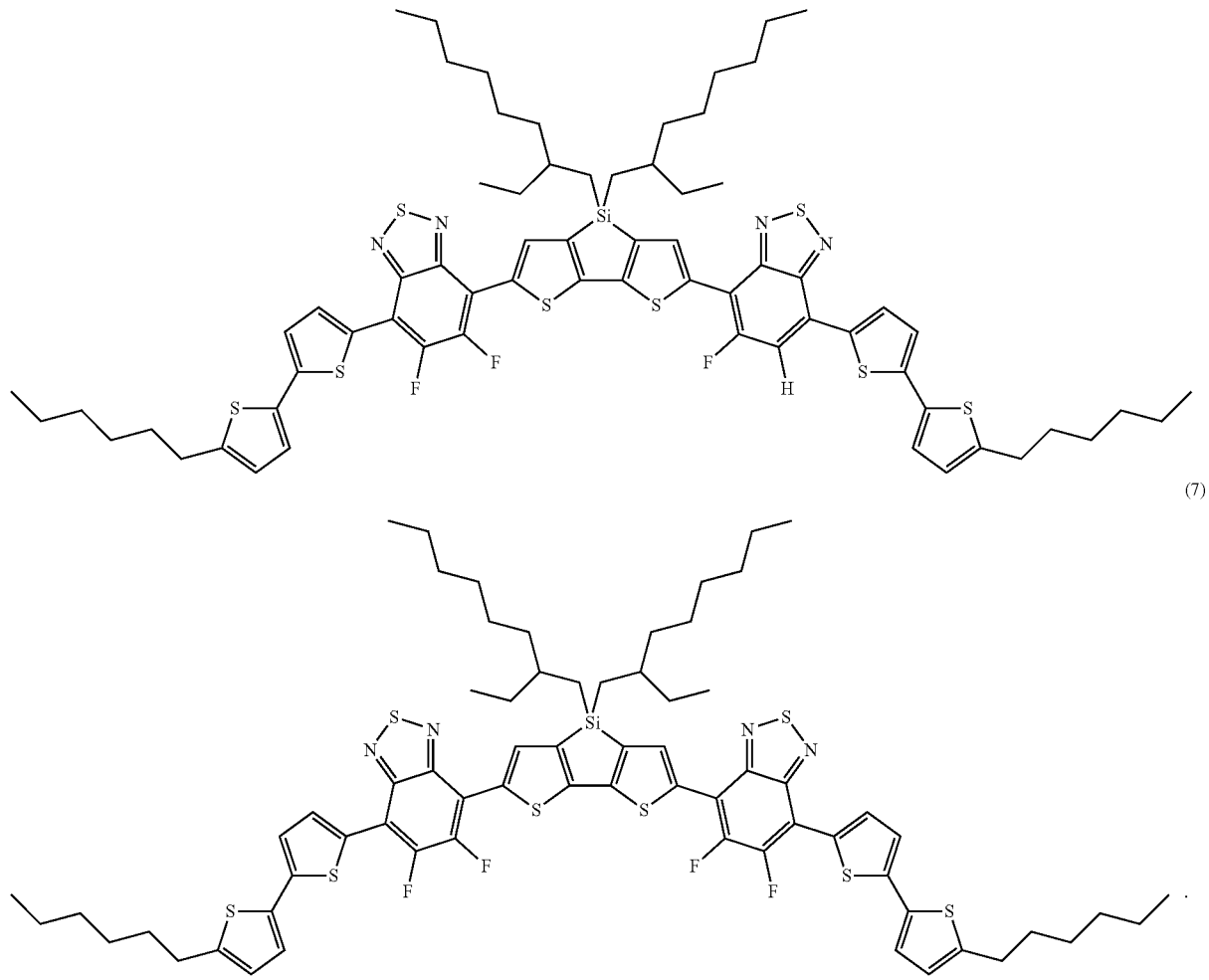

7. The organic solar cell according to claim 1, wherein the n-type organic semiconductor material (b) is selected from the group consisting of methyl (6,6)-phenyl-C61-butyrate (PC$_{60}$BM), (6,6)-phenyl-C61-butyric acid methyl ester (C$_{60}$-PCBM), (6,6)-phenyl-C71-butyric acid methyl ester (C$_{70}$-PCBM), (6,6)-phenyl-C77-butyric acid methyl ester (C$_{76}$-PCBM), (6,6)-phenyl-C79-butyric acid methyl ester (C$_{78}$-PCBM), (6,6)-phenyl-C81-butyric acid methyl ester (C$_{80}$-PCBM), (6,6)-phenyl-C83-butyric acid methyl ester (C$_{82}$-PCBM), (6,6)-phenyl-C85-butyric acid methyl ester (C$_{84}$-PCBM), bis(1-[3-(methoxycarbonyl)propyl]-1-phenyl) (Bis-C$_{60}$-PCBM), 3'-phenyl-3'H-cyclopropa(8,25)(5,6) fullerene-C70-bis-D5h(6)-3'-butyric acid methyl ester (Bis-C$_{70}$-PCBM), indene-C60-bisadduct (ICBA), monoindenyl C60 (ICMA), and combinations thereof.

8. The organic solar cell according to claim 1, wherein the first organic semiconductor material (a-1) is mixed with the second organic semiconductor material (a-2) in a weight ratio of 1:0.01-0.04.

9. The organic solar cell according to claim 1, wherein the solvent (c) is a mixture of chlorobenzene and 1,8-diiodooctane in a volume ratio of 1:0.002-5.

* * * * *